(12) United States Patent
Hauptmann et al.

(10) Patent No.: US 11,414,660 B2
(45) Date of Patent: Aug. 16, 2022

(54) PRODUCTS AND COMPOSITIONS

(71) Applicant: Silence Therapeutics GmbH, Berlin (DE)

(72) Inventors: Judith Hauptmann, Berlin (DE); Dmitry Samarsky, Berlin (DE); Adrien Weingärtner, Berlin (DE); Lucas Bethge, Berlin (DE); Christian Frauendorf, Berlin (DE); Alison Gallafent, Berlin (DE)

(73) Assignee: SILENCE THERAPEUTICS GMBH, Berlin (DE)

( * ) Notice: Subject to any disclaimer, the term of this patent is extended or adjusted under 35 U.S.C. 154(b) by 0 days.

(21) Appl. No.: 16/500,770

(22) PCT Filed: Apr. 5, 2018

(86) PCT No.: PCT/EP2018/058762
§ 371 (c)(1),
(2) Date: Oct. 3, 2019

(87) PCT Pub. No.: WO2018/185239
PCT Pub. Date: Oct. 11, 2018

(65) Prior Publication Data
US 2020/0063133 A1 Feb. 27, 2020

(30) Foreign Application Priority Data

Apr. 5, 2017 (EP) .................... 17165058
Nov. 13, 2017 (EP) .................... 17201353
Nov. 13, 2017 (EP) .................... 17201447

(51) Int. Cl.
*C12N 15/11* (2006.01)
*C12N 15/113* (2010.01)

(52) U.S. Cl.
CPC ........ *C12N 15/113* (2013.01); *C12N 2310/14* (2013.01); *C12N 2310/315* (2013.01); *C12N 2310/317* (2013.01); *C12N 2310/321* (2013.01); *C12N 2310/322* (2013.01); *C12N 2310/344* (2013.01); *C12N 2320/51* (2013.01)

(58) Field of Classification Search
CPC .............. C12N 15/113; C12N 2310/14; C12N 2310/315; C12N 2310/317; C12N 2310/321; C12N 2310/322; C12N 2310/344; C12N 2320/51
See application file for complete search history.

(56) References Cited

U.S. PATENT DOCUMENTS

| 11,015,198 | B2 | 5/2021 | Hauptmann et al. |
| 2009/0137500 | A1 | 5/2009 | McSwiggen et al. |
| 2012/0016005 | A1 | 1/2012 | Samarsky et al. |
| 2012/0040459 | A1 | 2/2012 | Khvorova et al. |
| 2014/0113950 | A1 | 4/2014 | Khvorova et al. |
| 2014/0364482 | A1 | 12/2014 | Khvorova et al. |
| 2016/0272970 | A1* | 9/2016 | Rozema ............... C12N 15/111 |
| 2019/0119676 | A1 | 4/2019 | Frauendorf et al. |
| 2020/0095580 | A1 | 3/2020 | Hauptmann et al. |
| 2020/0392494 | A1 | 12/2020 | Kordasiewicz et al. |

FOREIGN PATENT DOCUMENTS

| WO | WO-2016/149020 A1 | 9/2016 |
| WO | WO-2018/185239 A1 | 10/2018 |

OTHER PUBLICATIONS

Takei, Y. et al. (2002). "5'-,3'—Inverted Thymidine-Modified Antisense Oligodeoxynucleotide Targeting Midkine," The Journal of Biological Chemistry 277(26):23800-23806.
Watts, J.K. et al. (2012, e-pub. Nov. 9, 2011). "Silencing Disease Genes in the Laboratory and the Clinic," Journal of Pathology 226:365-379.
International Preliminary Report on Patentability dated Oct. 17, 2019, for PCT Patent Application No. PCT/EP2018/058762, filed Apr. 5, 2018, 7 pages.
International Search Report dated Jul. 3, 2018, for PCT Patent Application No. PCT/EP2018/058762, filed Apr. 5, 2018, 4 pages.
Kubo, T. et al. (Dec. 5, 2011, e-pub. Oct. 24, 2011). "Palmitic Acid-Conjugated 21—Nucleotide siRNA Enhances Gene-Silencing Activity," Molecular Pharmaceutics 8(6):2193-2203. (Abstract Only).
Written Opinion of the International Searching Authority dated Jul. 3, 2018, for PCT Patent Application No. PCT/EP2018/058762, filed Apr. 5, 2018, 5 pages.

* cited by examiner

*Primary Examiner* — Ekaterina Poliakova-Georgantas
(74) *Attorney, Agent, or Firm* — Morrison & Foerster LLP

(57) ABSTRACT

The present invention relates to products and compositions and their uses. In particular the invention relates to nucleic acid products that interfere with target gene expression or inhibit target gene expression and therapeutic uses of such products.

20 Claims, 17 Drawing Sheets
Specification includes a Sequence Listing.

Figure 1
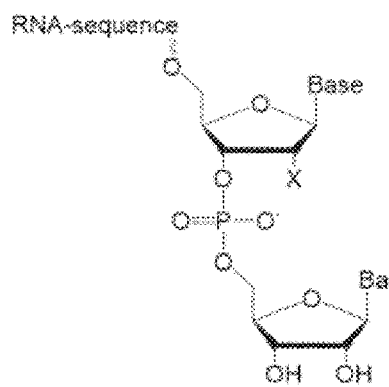
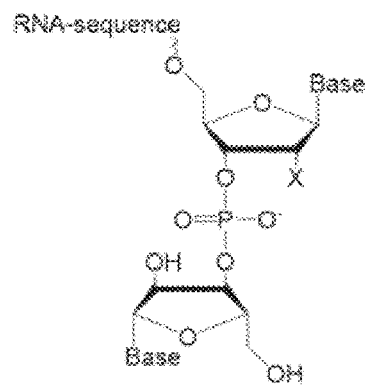
5'-3' Phosphodiester linkage
3'-3' Phosphodiester linkage
X = OMe, F, ...
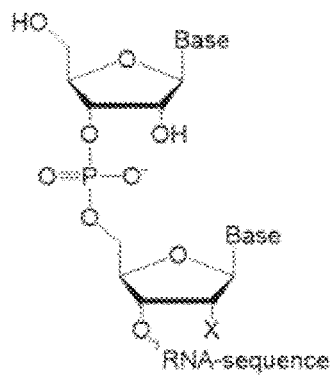
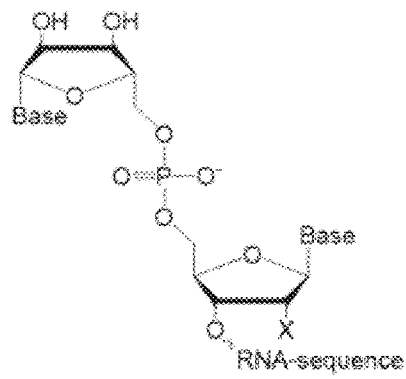
5'-3' Phosphodiester linkage
5'-5' Phosphodiester linkage
X = OMe, F, ...

Figure 2

| Duplex ID | sequence and chemistry top: first strand, bottom: second strand, both 5'-3' |
|---|---|
| TMP01 | mAfAmCfCmAfGmAfAmGfAmAfGmCfAmGfGmUfGmA |
|  | fUmCfAmCfCmUfGmCfUmUfCmUfUmCfUmGfGmUfU |
| TMP70 | mA(ps)fA(ps)mCfCmAfGmAfAmGfAmAfGmCfAmGfGmU(ps)fG(ps)mA |
|  | fU(ps)mC(ps)fAmCfCmUfGmCfUmUfCmUfUmCfUmGfG(ps)mU(ps)fU |
| TMP71 | mA(ps)fA(ps)mCfCmAfGmAfAmGfAmAfGmCfAmGfGmU(ps)fG(ps)mA ivA |
|  | fU(ps)mC(ps)fAmCfCmUfGmCfUmUfCmUfUmCfUmGfG(ps)mU(ps)fU ivA |
| TMP72 | mA(ps)fA(ps)mCfCmAfGmAfAmGfAmAfGmCfAmGfGmU(ps)fG(ps)mA ivU |
|  | fU(ps)mC(ps)fAmCfCmUfGmCfUmUfCmUfUmCfUmGfG(ps)mU(ps)fU ivU |
| TMP73 | mA(ps)fA(ps)mCfCmAfGmAfAmGfAmAfGmCfAmGfGmU(ps)fG(ps)mA ivC |
|  | fU(ps)mC(ps)fAmCfCmUfGmCfUmUfCmUfUmCfUmGfG(ps)mU(ps)fU ivC |
| TMP74 | mA(ps)fA(ps)mCfCmAfGmAfAmGfAmAfGmCfAmGfGmU(ps)fG(ps)mA ivG |
|  | fU(ps)mC(ps)fAmCfCmUfGmCfUmUfCmUfUmCfUmGfG(ps)mU(ps)fU ivG |
| TMP75 | mA(ps)fA(ps)mCfCmAfGmAfAmGfAmAfGmCfAmGfGmUfGmA ivA |
|  | fU(ps)mC(ps)fAmCfCmUfGmCfUmUfCmUfUmCfUmGfGmUfU ivA |
| TMP76 | mA(ps)fA(ps)mCfCmAfGmAfAmGfAmAfGmCfAmGfGmUfGmA ivU |
|  | fU(ps)mC(ps)fAmCfCmUfGmCfUmUfCmUfUmCfUmGfGmUfU ivU |
| TMP77 | mA(ps)fA(ps)mCfCmAfGmAfAmGfAmAfGmCfAmGfGmUfGmA ivC |
|  | fU(ps)mC(ps)fAmCfCmUfGmCfUmUfCmUfUmCfUmGfGmUfU ivC |
| TMP78 | mA(ps)fA(ps)mCfCmAfGmAfAmGfAmAfGmCfAmGfGmUfGmA ivG |
|  | fU(ps)mC(ps)fAmCfCmUfGmCfUmUfCmUfUmCfUmGfGmUfU ivG | mA, mU, mC, mG – 2'-OMe RNA
fA, fU, fC, fG – 2'-F RNA
ivA, ivU, ivC, ivG - inverted RNA (3'-3')
(ps) – phosphorothioate

Figure 7

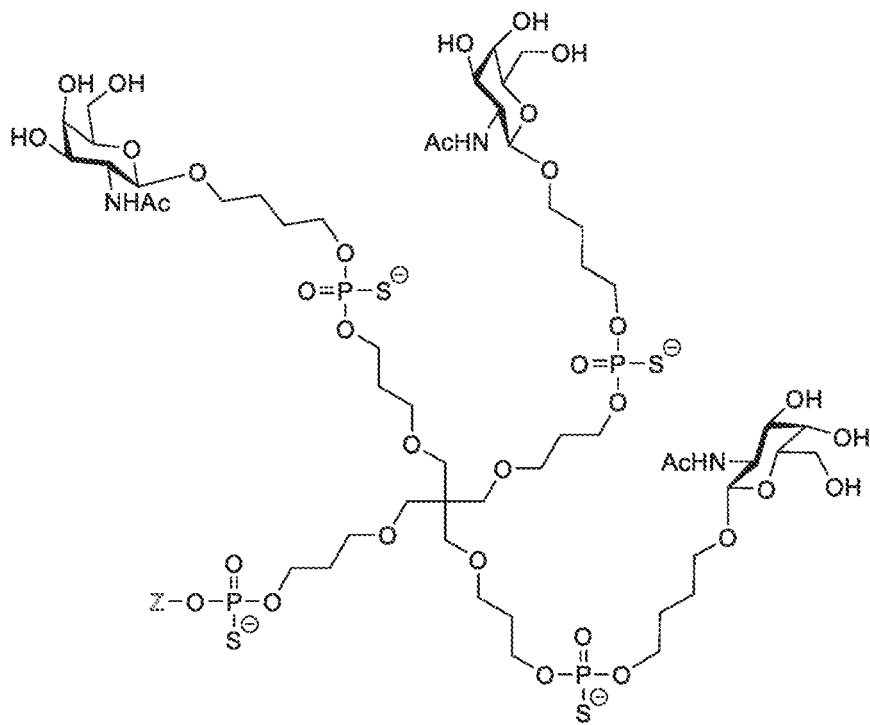

Figure 8

| Duplex ID | sequence and chemistry top: first strand, bottom: second strand, both 5'-3' |
|---|---|
| TMP70 | mA(ps)fA(ps)mCfCmAfGmAfAmGfAmAfGmCfAmGfGmU(ps)fG(ps)mA |
|  | fU(ps)mC(ps)fAmCfCmUfGmCfUmUfCmUfUmCfUmGfG(ps)mU(ps)fU |
| TMP82 | mA(ps)fA(ps)mCfCmAfGmAfAmGfAmAfGmCfAmGfGmUfGmA(ps)ivA |
|  | fU(ps)mC(ps)fAmCfCmUfGmCfUmUfCmUfUmCfUmGfGmUfU(ps)ivA |
| TMP83 | mA(ps)fA(ps)mCfCmAfGmAfAmGfAmAfGmCfAmGfGmUfGmA(ps)ivG |
|  | fU(ps)mC(ps)fAmCfCmUfGmCfUmUfCmUfUmCfUmGfGmUfU(ps)ivG | mA, mU, mC, mG – 2'-OMe RNA
fA, fU, fC, fG – 2'-F RNA
ivA, ivG - inverted RNA (3'-3')
(ps) – phosphorothioate

Figure 19

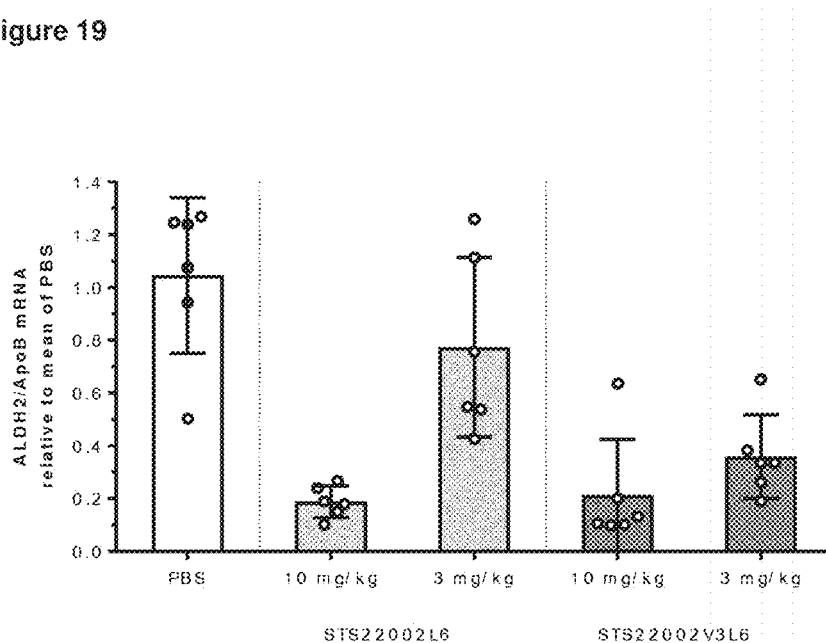

Figure 20

| Duplex ID | sequence and chemistry top: first strand, bottom: second strand, both 5'-3' |
|---|---|
| STS22006L6 | mU(ps)fC(ps)mUfUmCfUmUfAmAfAmCfUmGfAmGfUmU(ps)fU(ps)mC |
|  | [ST23(ps)]3 ST43(ps)fGmAfAmAfCmUfCmAfGmUfUmUfAmAfGmAfA(ps)mG(ps)fA |
| STS22006V7L6 | mU(ps)fC(ps)mUfUmCfUmUfAmAfAmCfUmGfAmGfUmU(ps)fU(ps)mC |
|  | [ST23(ps)]3 ST43(ps)fGmAfAmAfCmUfCmAfGmUfUmUfAmAfGmAfAivA |
| STS22006V8L6 | mU(ps)fC(ps)mUfUmCfUmUfAmAfAmCfUmGfAmGfUmUfUmCivA |
|  | [ST23(ps)]3 ST43(ps)fGmAfAmAfCmUfCmAfGmUfUmUfAmAfGmAfA(ps)mG(ps)fA |
| STS22006V9L6 | mU(ps)fC(ps)mUfUmCfUmUfAmAfAmCfUmGfAmGfUmUfUmCivA |
|  | [ST23(ps)]3 ST43(ps)fGmAfAmAfCmUfCmAfGmUfUmUfAmAfGmAfAivA |
| STS22006V10L35 | mU(ps)fC(ps)mUfUmCfUmUfAmAfAmCfUmGfAmGfUmU(ps)fU(ps)mC[(ps)Ser(GN)]3 |
|  | ivAfGmAfAmAfCmUfCmAfGmUfUmUfAmAfGmAfAivA | mA, mU, mC, mG – 2'-OMe RNA
fA, fU, fC, fG – 2'-F RNA
ivA - inverted RNA (3'-3' or 5'-5')
(ps) – phosphorothioate

Figure 21

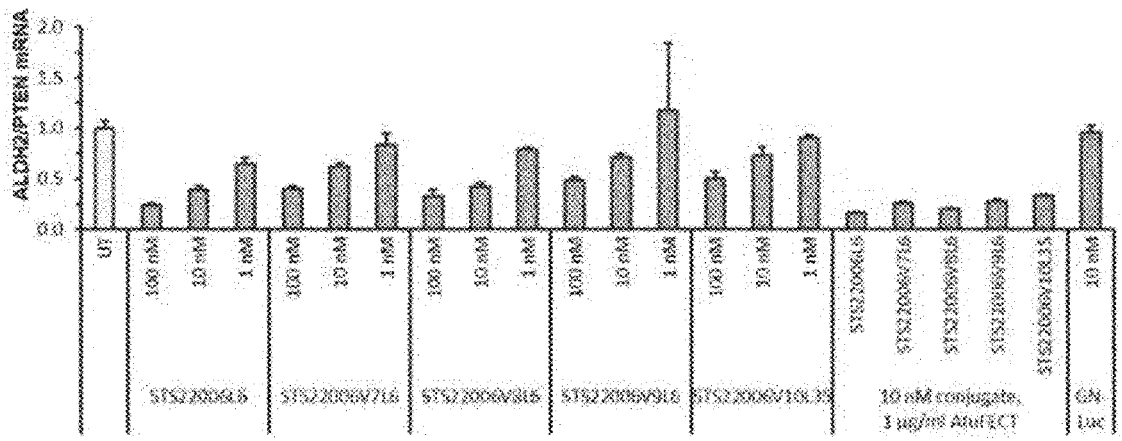

Figure 22

| Duplex ID | sequence and chemistry<br>top: first strand, bottom: second strand, both 5'-3' |
|---|---|
| STS22009L6 | mA(ps)fU(ps)mGfUmAfGmCfCmGfAmGfGmAfUmCfUmU(ps)fC(ps)mU<br>[ST23(ps)]3 ST43(ps)fAmGfAmAfGmAfUmCfCmUfCmGfGmCfUmAfC(ps)mA(ps)fU |
| STS22009V3L6 | mA(ps)fU(ps)mGfUmAfGmCfCmGfAmGfGmAfUmCfUmU(ps)fC(ps)mU<br>[ST23(ps)]3 ST43(ps)fAmGfAmAfGmAfUmCfCmUfCmGfGmCfUmAfCmAfUivA |
| STS22009V4L6 | mA(ps)fU(ps)mGfUmAfGmCfCmGfAmGfGmAfUmCfUmUfCmUivA<br>[ST23(ps)]3 ST43(ps)fAmGfAmAfGmAfUmCfCmUfCmGfGmCfUmAfC(ps)mA(ps)fU |
| STS22009V5L6 | mA(ps)fU(ps)mGfUmAfGmCfCmGfAmGfGmAfUmCfUmUfCmUivA<br>[ST23(ps)]3 ST43(ps)fAmGfAmAfGmAfUmCfCmUfCmGfGmCfUmAfUivA |
| STS22009V6L35 | mA(ps)fU(ps)mGfUmAfGmCfCmGfAmGfGmAfUmCfUmU(ps)fC(ps)mU[(ps)Ser(GN)]3<br>ivAfAmGfAmAfGmAfUmCfCmUfCmGfGmCfUmAfCmAfUivA | mA, mU, mC, mG – 2'-OMe RNA
fA, fU, fC, fG – 2'-F RNA
ivA – inverted RNA (3'-3' or 5'-5')
(ps) – phosphorothioate

Figure 23

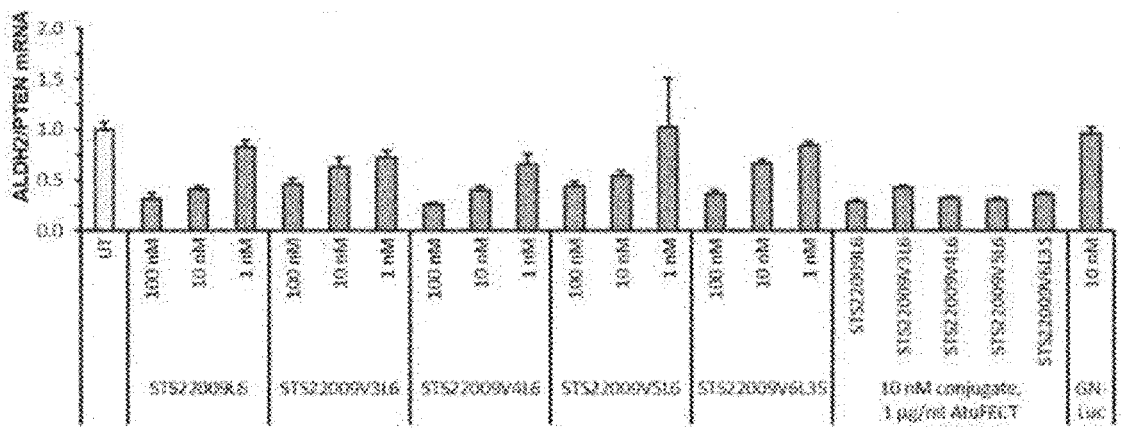

Figure 24

| Duplex ID | sequence and chemistry top: first strand, bottom: second strand, both 5'-3' |
|---|---|
| STS16001L1 | mU(ps)fU(ps)mAfUmAfGmAfGmCfAmAfGmAfAmCfAmCfUmG(ps)fU(ps)mU |
|  | [ST23(ps)]3 ltrb(ps)fAmAfCmAfGmUfGmUfUmCfUmGfGmCfUmCfUmAfU(ps)mA(ps)fA |
| STS16001V11L1 | mU(ps)fU(ps)mAfUmAfGmAfGmCfAmAfGmAfAmCfAmCfUmG(ps)fU(ps)mU |
|  | [ST23(ps)]3 ltrb(ps)fAmAfCmAfGmUfGmUfUmCfUmGfGmCfUmCfUmAfUmAfAivA |
| STS16001V12L1 | mU(ps)fU(ps)mAfUmAfGmAfGmCfAmAfGmAfAmCfAmCfUmGfUmUivA |
|  | [ST23(ps)]3 ltrb(ps)fAmAfCmAfGmUfGmUfUmCfUmGfGmCfUmCfUmAfU(ps)mA(ps)fA |
| STS16001V13L1 | mU(ps)fU(ps)mAfUmAfGmAfGmCfAmAfGmAfAmCfAmCfUmGfUmUivA |
|  | [ST23(ps)]3 ltrb(ps)fAmAfCmAfGmUfGmUfUmCfUmGfGmCfUmCfUmAfUmAfAivA |
| STS16001V14L35 | mU(ps)fU(ps)mAfUmAfGmAfGmCfAmAfGmAfAmCfAmCfUmG(ps)fU(ps)mU[(ps)Ser(GN)]3 |
|  | ivAfAmAfCmAfGmUfGmUfUmCfUmGfGmCfUmCfUmAfUmAfAivA | mA, mU, mC, mG – 2'-OMe RNA
fA, fU, fC, fG – 2'-F RNA
ivA - inverted RNA (3'-3' or 5'-5')
(ps) – phosphorothioate

Figure 25

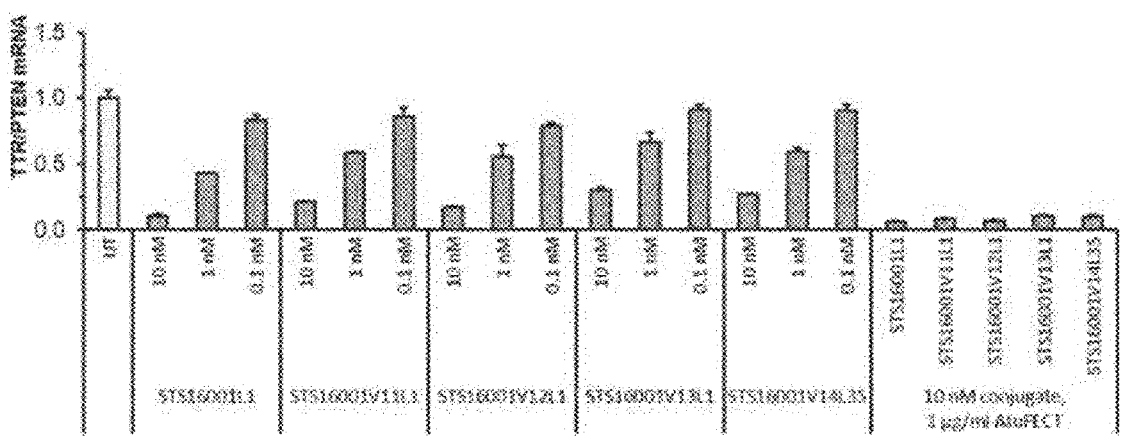

Figure 26

| Duplex ID | sequence and chemistry<br>top: first strand, bottom: second strand, both 5'-3' |
|---|---|
| STS22002L6 | mA(ps)fA(ps)mUfGmUfUmUfUmCfCmUfGmCfUmGfAmC(ps)fG(ps)mG |
| | [ST23(ps)]3 ST43(ps)fCmCfGmUfCmAfGmCfAmGfGmAfAmAfAmCfA(ps)mU(ps)fU |
| STS22002V8L6 | mA(ps)fA(ps)mUfGmUfUmUfUmCfCmUfGmCfUmGfAmCfGivA |
| | [ST23(ps)]3 ST43(ps)fCmCfGmUfCmAfGmCfAmGfGmAfAmAfAmCfA(ps)mU(ps)fU |
| STS22002V9L6 | mA(ps)fA(ps)mUfGmUfUmUfUmCfCmUfGmCfUmGfAmCfGivA |
| | [ST23(ps)]3 ST43(ps)fCmCfGmUfCmAfGmCfAmGfGmAfAmAfAmCfAmUivA |
| STS22002V10L6 | mA(ps)fA(ps)mUfGmUfUmUfUmCfCmUfGmCfUmGfAmCfGmGivA |
| | [ST23]3 ST43 fCmCfGmUfCmAfGmCfAmGfGmAfAmAfAmCfAmUivA | mA, mU, mC, mG – 2'-OMe RNA
fA, fU, fC, fG – 2'-F RNA
ivA - inverted RNA (3'-3' or 5'-5')
(ps) – phosphorothioate

Figure 27

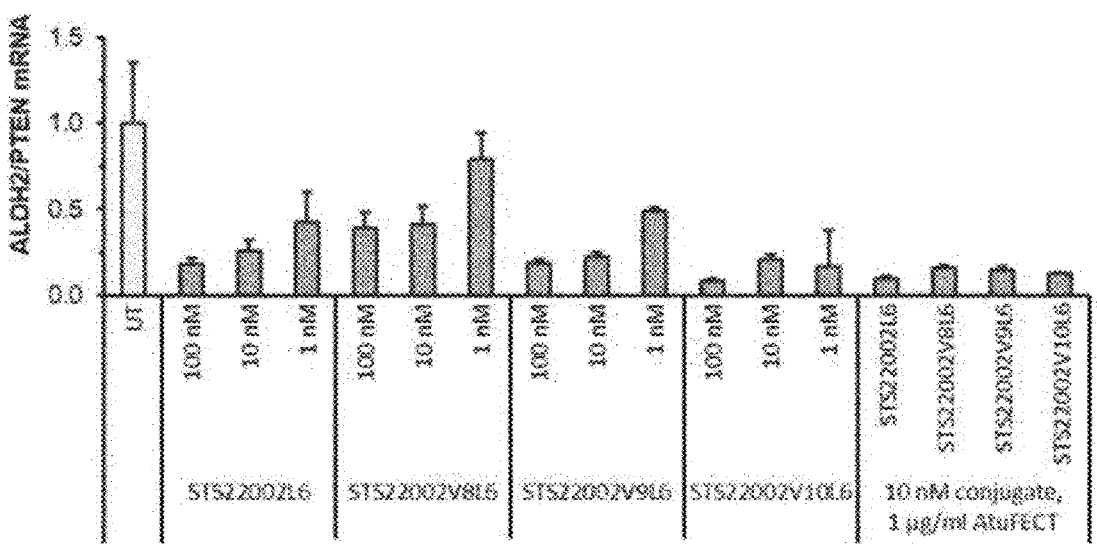

Figure 28

| Duplex ID | sequence and chemistry top: first strand, bottom: second strand, both 5'-3' |
|---|---|
| STS22006L6 | mU(ps)fC(ps)mUfUmCfUmUfAmAfAmCfUmGfAmGfUmU(ps)fU(ps)mC<br>GalNAc-fGmAfAmAfCmUfCmAfGmUfUmUfAmAfGmAfAmGfA |
| STS22006V1L6 | mU(ps)fC(ps)mUfUmCfUmUfAmAfAmCfUmGfAmGfUmU(ps)fU(ps)mC<br>GalNAc-mGmAmAmAmCmUfCfAfGmUmUmUmAmAmGmAmAmG ivA |
| STS22009L6 | mA(ps)fU(ps)mGfUmAfGmCfCmGfAmGfGmAfUmCfUmU(ps)fC(ps)mU<br>GalNAc-fAmGfAmAfGmAfUmCfCmUfCmGfGmCfUmAfCmAfU |
| STS22009V1L6 | mA(ps)fU(ps)mGfUmAfGmCfCmGfAmGfGmAfUmCfUmU(ps)fC(ps)mU<br>GalNAc-mAmGmAmAmGmAfUfCfCmUmCmGmGmCmUmAmCmA ivA |
| STS22009V2L6 | mA(ps)fU(ps)mGmUmAmGmCmCmGmAmGmGmAfUmCmUmU(ps)mC(ps)mU<br>GalNAc-mAmGmAmAmGmAfUfCfCmUmCmGmGmCmUmAmCmA ivA | mA, mU, mC, mG – 2'-OMe RNA
fA, fU, fC, fG – 2'-F RNA
ivA - inverted RNA (3'-3')
(ps) – phosphorothioate
GalNAc - [ST23 (ps)]3 ST43 (ps)

Figure 29

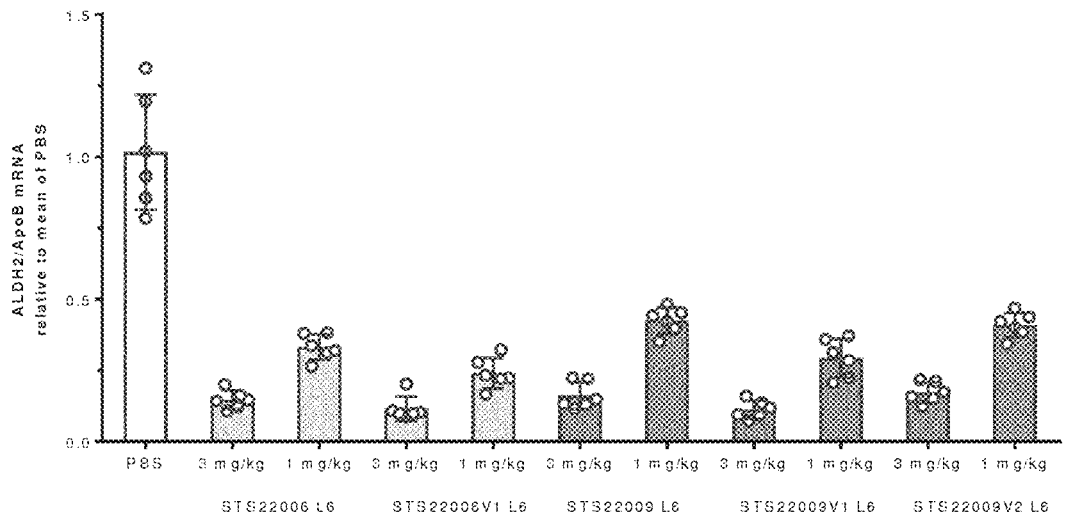

Figure 30

| siRNA | sequence and chemistry<br>top: first strand, bottom: second strand, both 5'-3' |
|---|---|
| STS1830OL4 | mU(ps)fC(ps)mGfAmAfGmUfAmUfCmGfCmGfUmA(ps)fC(ps)mG |
| Luc (X0028) | [ST23(ps)]3 ST4i(ps)fCmGfUmAfCmGfCmGfCmAfAmCfUmUfC(ps)mG(ps)fA |
| STS16001V4L11<br>X0107 | mU(ps)fU(ps)mAfUmAfGmAfGmCfAmAfGmAfAmCfAmCfUmG(ps)fU(ps)mU(ps)GlyC3Am(GalNAc)<br>fA(ps)mA(ps)fCmAfGmUfGmUfGmCfUmCfUmCfUmAfU(ps)mA(ps)fA |
| STS16001L22<br>X0139 | mU(ps)f0(ps)mAfUmAfGmAfGmCfAmAfGmAfAmCfAmCfUmG(ps)fU(ps)mU<br>Ser(GN)(ps)Ser(GN)(ps)fAmAfCmAfGmUfGmUfGmCfUmCfUmCfUmAfU(ps)mA(ps)fA |
| STS16001V7L22<br>X0258 | (po)ivAfUmAfGmAfGmCfAmAfGmAfAmCfAmCfUmG(ps)fU(ps)mU<br>Ser(GN)(ps)Ser(GN)(ps)fAmAfCmAfGmUfGmUfGmCfUmCfUmCfUmAfU(ps)mA(ps)fA |
| STS16001V8L22<br>X0259 | (po)ivGfUmAfGmAfGmCfAmAfGmAfAmCfAmCfUmG(ps)fU(ps)mU<br>Ser(GN)(ps)Ser(GN)(ps)fAmAfCmAfGmUfGmUfGmCfUmCfUmCfUmAfU(ps)mA(ps)fA |
| STS16001V9L22<br>X0260 | (po)ivUfUmAfGmAfGmCfAmAfGmAfAmCfAmCfUmG(ps)fU(ps)mU<br>Ser(GN)(ps)Ser(GN)(ps)fAmAfCmAfGmUfGmUfGmCfUmCfUmCfUmAfU(ps)mA(ps)fA |
| STS16001V10L22<br>X0261 | (po)ivCfUmAfGmAfGmCfAmAfGmAfAmCfAmCfUmG(ps)fU(ps)mU<br>Ser(GN)(ps)Ser(GN)(ps)fAmAfCmAfGmUfGmUfGmCfUmCfUmCfUmAfU(ps)mA(ps)fA |
| STS16001V6L11<br>X0264 | mU(ps)fU(ps)mAfUmAfGmAfGmCfAmAfGmAfAmCfAmCfUmG(ps)fU(ps)mU(ps)GlyC3Am(GalNAc)<br>ivAfAmAfCmAfGmUfGmUfGmCfUmCfUmCfUmAfU(ps)mA(ps)fA |
| STS16001V7L11<br>X0265 | m0(ps)f0(ps)mAfUmAfGmAfGmCfAmAfGmAfAmCfAmCfUmG(ps)fU(ps)mU(ps)GlyC3Am(GalNAc)<br>ivGfAmAfCmAfGmUfGmUfGmCfUmCfUmCfUmAfU(ps)mA(ps)fA |
| STS16001V8L11<br>X0266 | mU(ps)fU(ps)mAfUmAfGmAfGmCfAmAfGmAfAmCfAmCfUmG(ps)fU(ps)mU(ps)GlyC3Am(GalNAc)<br>ivUfAmAfCmAfGmUfGmUfGmCfUmCfUmCfUmAfU(ps)mA(ps)fA |
| STS16001V9L11<br>X0267 | mU(ps)f0(ps)mAfUmAfGmAfGmCfAmAfGmAfAmCfAmCfUmG(ps)fU(ps)mU(ps)GlyC3Am(GalNAc)<br>ivCfAmAfCmAfGmUfGmUfGmCfUmCfUmCfUmAfU(ps)mA(ps)fA | mA, mU, mC, mG – 2'-OMe RNA
fA, fU, fC, fG – 2'-F RNA
(ps) – phosphorothioate
ivA, ivU, ivC, ivG: inverted ribonucleotide with 5'-5' linkage
(po)ivA, (po)ivU, (po)ivC, (po)ivG: 3' phosphate inverted ribonucleotide

SEQUENCE LISTING

<160> NUMBER OF SEQ ID NOS: 205

<210> SEQ ID NO 1
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 1
aaccagaaga agcagguga                                                19

<210> SEQ ID NO 2
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 2
ucaccugcuu cuucugguu                                                19

<210> SEQ ID NO 3
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 3
aaccagaaga agcagguga                                                19

<210> SEQ ID NO 4
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 4
ucaccugcuu cuucugguu                                                19

<210> SEQ ID NO 5
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 5
aaccagaaga agcaggugaa                                               20

<210> SEQ ID NO 6

```
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 6
ucaccugcuu cuucugguua                                               20

<210> SEQ ID NO 7
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 7
aaccagaaga agcaggugau                                               20

<210> SEQ ID NO 8
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 8
ucaccugcuu cuucugguuu                                               20

<210> SEQ ID NO 9
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 9
aaccagaaga agcaggugac                                               20

<210> SEQ ID NO 10
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 10
ucaccugcuu cuucugguuc                                               20

<210> SEQ ID NO 11
<211> LENGTH: 20
<212> TYPE: RNA
<213> ORGANISM: Artificial Sequence
<220> FEATURE:
```

```
<223> OTHER INFORMATION: siRNA
<220> FEATURE:
<223> OTHER INFORMATION: modified_base, modified as per summary sequence
      table at the end of the description

<400> SEQUENCE: 11
aaccagaaga agcaggugag                                                     20

<210> SEQ ID NO 12
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 12
ucaccugcuu cuucugguug                                                     20

<210> SEQ ID NO 13
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 13
aaccagaaga agcaggugaa                                                     20

<210> SEQ ID NO 14
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 14
ucaccugcuu cuucugguua                                                     20

<210> SEQ ID NO 15
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 15
aaccagaaga agcaggugau                                                     20

<210> SEQ ID NO 16
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description
```

<400> SEQUENCE: 16
ucaccugcuu cuucugguuu                                              20

<210> SEQ ID NO 17
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 17
aaccagaaga agcaggugac                                              20

<210> SEQ ID NO 18
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 18
ucaccugcuu cuucugguuc                                              20

<210> SEQ ID NO 19
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 19
aaccagaaga agcaggugag                                              20

<210> SEQ ID NO 20
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 20
ucaccugcuu cuucugguug                                              20

<210> SEQ ID NO 21
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 21
aaccagaaga agcaggugaa                                              20

<210> SEQ ID NO 22
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
     table at the end of the description

<400> SEQUENCE: 22
ucaccugcuu cuucugguua                                               20

<210> SEQ ID NO 23
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
     table at the end of the description

<400> SEQUENCE: 23
aaccagaaga agcaggugag                                               20

<210> SEQ ID NO 24
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
     table at the end of the description

<400> SEQUENCE: 24
ucaccugcuu cuucugguug                                               20

<210> SEQ ID NO 25
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
     table at the end of the description

<400> SEQUENCE: 25
aaccagaaga agcagguga                                                19

<210> SEQ ID NO 26
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
     table at the end of the description

<400> SEQUENCE: 26
ucaccugcuu cuucugguug                                               20

<210> SEQ ID NO 27
<211> LENGTH: 19

```
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 27
aaccagaaga agcaggugu                                                    19

<210> SEQ ID NO 28
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 28
ucaccugcuu cuucugguug                                                   20

<210> SEQ ID NO 29
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 29
aaccagaaga agcaggugc                                                    19

<210> SEQ ID NO 30
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 30
ucaccugcuu cuucugguug                                                   20

<210> SEQ ID NO 31
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 31
aaccagaaga agcaggugg                                                    19

<210> SEQ ID NO 32
<211> LENGTH: 20
<212> TYPE: RNA
<213> ORGANISM: Artificial Sequence
<220> FEATURE:
<223> OTHER INFORMATION: siRNA
```

```
<220> FEATURE:
<223> OTHER INFORMATION: modified_base, modified as per summary sequence
      table at the end of the description

<400> SEQUENCE: 32
ucaccugcuu cuucgguug                                                    20

<210> SEQ ID NO 33
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 33
aaccagaaga agcaggugag                                                   20

<210> SEQ ID NO 34
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 34
ucaccugcuu cuucggua                                                     19

<210> SEQ ID NO 35
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 35
aaccagaaga agcaggugag                                                   20

<210> SEQ ID NO 36
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 36
ucaccugcuu cuucgguu                                                     19

<210> SEQ ID NO 37
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description
```

```
<400> SEQUENCE: 37
aaccagaaga agcaggugag                                                    20

<210> SEQ ID NO 38
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 38
ucaccugcuu cuucugguc                                                     19

<210> SEQ ID NO 39
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 39
aaccagaaga agcaggugag                                                    20

<210> SEQ ID NO 40
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 40
ucaccugcuu cuucuggug                                                     19

<210> SEQ ID NO 41
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 41
aaccagaaga agcagguga                                                     19

<210> SEQ ID NO 42
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 42
ucaccugcuu cuucugguu                                                     19
```

```
<210> SEQ ID NO 43
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 43
aaccagaaga agcaggugaa                                                   20

<210> SEQ ID NO 44
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 44
ucaccugcuu cuucugguua                                                   20

<210> SEQ ID NO 45
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 45
aaccagaaga agcaggugag                                                   20

<210> SEQ ID NO 46
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 46
ucaccugcuu cuucugguug                                                   20

<210> SEQ ID NO 47
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 47
aaccagaaga agcaggugaa                                                   20

<210> SEQ ID NO 48
<211> LENGTH: 20
<212> TYPE: RNA
```

```
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 48
ucaccugcuu cuucugguua                                                   20

<210> SEQ ID NO 49
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 49
aaccagaaga agcaggugag                                                   20

<210> SEQ ID NO 50
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 50
ucaccugcuu cuucugguug                                                   20

<210> SEQ ID NO 51
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 51
aauguuuucc ugcugacgg                                                    19

<210> SEQ ID NO 52
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 52
ccgucagcag gaaaacauu                                                    19

<210> SEQ ID NO 53
<211> LENGTH: 20
<212> TYPE: RNA
<213> ORGANISM: Artificial Sequence
<220> FEATURE:
<223> OTHER INFORMATION: siRNA
<220> FEATURE:
```

<223> OTHER INFORMATION: modified_base, modified as per summary sequence
      table at the end of the description

<400> SEQUENCE: 53
aauguuuucc ugcugacgga                                                    20

<210> SEQ ID NO 54
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 54
ccgucagcag gaaaacauua                                                    20

<210> SEQ ID NO 55
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 55
aauguuuucc ugcugacggu                                                    20

<210> SEQ ID NO 56
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 56
ccgucagcag gaaaacauuu                                                    20

<210> SEQ ID NO 57
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 57
aauguuuucc ugcugacggc                                                    20

<210> SEQ ID NO 58
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 58
ccgucagcag gaaaacauuc                                               20

<210> SEQ ID NO 59
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 59
aauguuuucc ugcugacggg                                               20

<210> SEQ ID NO 60
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 60
ccgucagcag gaaaacauug                                               20

<210> SEQ ID NO 61
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 61
aauguuuucc ugcugacga                                                19

<210> SEQ ID NO 62
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 62
ccgucagcag gaaaacaua                                                19

<210> SEQ ID NO 63
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 63
aauguuuucc ugcugacgu                                                19

```
<210> SEQ ID NO 64
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 64
ccgucagcag gaaaacauu                                                19

<210> SEQ ID NO 65
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 65
aauguuuucc ugcugacgc                                                19

<210> SEQ ID NO 66
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 66
ccgucagcag gaaaacauc                                                19

<210> SEQ ID NO 67
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 67
aauguuuucc ugcugacgg                                                19

<210> SEQ ID NO 68
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 68
ccgucagcag gaaaacaug                                                19

<210> SEQ ID NO 69
<211> LENGTH: 19
<212> TYPE: RNA
<213> ORGANISM: Artificial Sequence
```

```
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 69 aauguuucc ugcugacgg                                                    19

<210> SEQ ID NO 70
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 70
ccgucagcag gaaaacauu                                                   19

<210> SEQ ID NO 71
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 71 aauguuucc ugcugacgg                                                    19

<210> SEQ ID NO 72
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 72
ccgucagcag gaaaacaua                                                   19

<210> SEQ ID NO 73
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 73 aauguuucc ugcugacgg                                                    19

<210> SEQ ID NO 74
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
``` table at the end of the description

<400> SEQUENCE: 74
ccgucagcag gaaaacaug                                              19

<210> SEQ ID NO 75
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 75
aauguuuucc ugcugacgga                                             20

<210> SEQ ID NO 76
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 76
ccgucagcag gaaaacauu                                              19

<210> SEQ ID NO 77
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 77
aauguuuucc ugcugacggg                                             20

<210> SEQ ID NO 78
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 78
ccgucagcag gaaaacauu                                              19

<210> SEQ ID NO 79
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 79

```
ucuucuuaaa cugaguuuc                                              19

<210> SEQ ID NO 80
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 80
gaaacucagu uuaagaaga                                              19

<210> SEQ ID NO 81
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 81
ucuucuuaaa cugaguuuc                                              19

<210> SEQ ID NO 82
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 82
gaaacucagu uuaagaagaa                                             20

<210> SEQ ID NO 83
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 83
ucuucuuaaa cugaguuuca                                             20

<210> SEQ ID NO 84
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 84
gaaacucagu uuaagaaga                                              19

<210> SEQ ID NO 85
```

```
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 85
ucuucuuaaa cugaguuuca                                                     20

<210> SEQ ID NO 86
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 86
gaaacucagu uuaagaagaa                                                     20

<210> SEQ ID NO 87
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 87
ucuucuuaaa cugaguuuc                                                      19

<210> SEQ ID NO 88
<211> LENGTH: 21
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 88
agaaacucag uuuaagaaga a                                                   21

<210> SEQ ID NO 89
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 89
auguagccga ggaucuucu                                                      19

<210> SEQ ID NO 90
<211> LENGTH: 19
<212> TYPE: RNA
<213> ORGANISM: Artificial Sequence
<220> FEATURE:
```

```
<223> OTHER INFORMATION: siRNA
<220> FEATURE:
<223> OTHER INFORMATION: modified_base, modified as per summary sequence
      table at the end of the description

<400> SEQUENCE: 90
agaagauccu cggcuacau                                                19

<210> SEQ ID NO 91
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 91
auguagccga ggaucuucu                                                19

<210> SEQ ID NO 92
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 92
agaagauccu cggcuacaua                                               20

<210> SEQ ID NO 93
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 93
auguagccga ggaucuucua                                               20

<210> SEQ ID NO 94
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 94
agaagauccu cggcuacau                                                19

<210> SEQ ID NO 95
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description
```

<400> SEQUENCE: 95
auguagccga ggaucuucua                                                    20

<210> SEQ ID NO 96
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 96
agaagauccu cggcuacaua                                                    20

<210> SEQ ID NO 97
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 97
auguagccga ggaucuucu                                                     19

<210> SEQ ID NO 98
<211> LENGTH: 21
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 98
aagaagaucc ucggcuacau a                                                  21

<210> SEQ ID NO 99
<211> LENGTH: 21
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 99
uuauagagca agaacacugu u                                                  21

<210> SEQ ID NO 100
<211> LENGTH: 21
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 100
aacaguguuc uugcucuaua a                                                  21

-continued

```
<210> SEQ ID NO 101
<211> LENGTH: 21
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 101
uuauagagca agaacacugu u                                                 21

<210> SEQ ID NO 102
<211> LENGTH: 22
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 102
aacaguguuc uugcucuaua aa                                                22

<210> SEQ ID NO 103
<211> LENGTH: 22
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 103
uuauagagca agaacacugu ua                                                22

<210> SEQ ID NO 104
<211> LENGTH: 21
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 104
aacaguguuc uugcucuaua a                                                 21

<210> SEQ ID NO 105
<211> LENGTH: 22
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 105
uuauagagca agaacacugu ua                                                22

<210> SEQ ID NO 106
<211> LENGTH: 22
```

```
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 106
aacaguguuc uugcucuaua aa                                              22

<210> SEQ ID NO 107
<211> LENGTH: 21
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 107
uuauagagca agaacacugu u                                               21

<210> SEQ ID NO 108
<211> LENGTH: 23
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 108
aaacaguguu cuugcucuau aaa                                             23

<210> SEQ ID NO 109
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 109
aauguuuucc ugcugacgg                                                  19

<210> SEQ ID NO 110
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 110
ccgucagcag gaaaacauu                                                  19

<210> SEQ ID NO 111
<211> LENGTH: 19
<212> TYPE: RNA
<213> ORGANISM: Artificial Sequence
<220> FEATURE:
<223> OTHER INFORMATION: siRNA
```

```
<220> FEATURE:
<223> OTHER INFORMATION: modified_base, modified as per summary sequence
      table at the end of the description

<400> SEQUENCE: 111
aauguuuucc ugcugacga                                                    19

<210> SEQ ID NO 112
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 112
ccgucagcag gaaaacauu                                                    19

<210> SEQ ID NO 113
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 113
aauguuuucc ugcugacga                                                    19

<210> SEQ ID NO 114
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 114
ccgucagcag gaaaacaua                                                    19

<210> SEQ ID NO 115
<211> LENGTH: 20
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 115
aauguuuucc ugcugacgga                                                   20

<210> SEQ ID NO 116
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description
```

```
<400> SEQUENCE: 116
ccgucagcag gaaaacaua                                                    19

<210> SEQ ID NO 117
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 117
ucuucuuaaa cugaguuuc                                                    19

<210> SEQ ID NO 118
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 118
gaaacucagu uuaagaaga                                                    19

<210> SEQ ID NO 119
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 119
auguagccga ggaucuucu                                                    19

<210> SEQ ID NO 120
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 120
agaagauccu cggcuacaa                                                    19

<210> SEQ ID NO 121
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 121
auguagccga ggaucuucu                                                    19
```

```
<210> SEQ ID NO 122
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 122
agaagauccu cggcuacaa                                                19

<210> SEQ ID NO 123
<211> LENGTH: 19
<212> TYPE: RNA
<213> ORGANISM: Artificial Sequence
<220> FEATURE:
<223> OTHER INFORMATION: siRNA

<400> SEQUENCE: 123
aaccagaaga agcagguga                                                19

<210> SEQ ID NO 124
<211> LENGTH: 19
<212> TYPE: RNA
<213> ORGANISM: Artificial Sequence
<220> FEATURE:
<223> OTHER INFORMATION: siRNA

<400> SEQUENCE: 124
ucaccugcuu cuucugguu                                                19

<210> SEQ ID NO 125
<211> LENGTH: 20
<212> TYPE: RNA
<213> ORGANISM: Artificial Sequence
<220> FEATURE:
<223> OTHER INFORMATION: siRNA

<400> SEQUENCE: 125
aaccagaaga agcaggugaa                                               20

<210> SEQ ID NO 126
<211> LENGTH: 20
<212> TYPE: RNA
<213> ORGANISM: Artificial Sequence
<220> FEATURE:
<223> OTHER INFORMATION: siRNA

<400> SEQUENCE: 126
ucaccugcuu cuucugguua                                               20

<210> SEQ ID NO 127
<211> LENGTH: 20
<212> TYPE: RNA
<213> ORGANISM: Artificial Sequence
<220> FEATURE:
<223> OTHER INFORMATION: siRNA

<400> SEQUENCE: 127
aaccagaaga agcaggugau                                               20

<210> SEQ ID NO 128
<211> LENGTH: 20
<212> TYPE: RNA
```

```
<213> ORGANISM: Artificial Sequence
<220> FEATURE:
<223> OTHER INFORMATION: siRNA

<400> SEQUENCE: 128
ucaccugcuu cuucugguuu                                                    20

<210> SEQ ID NO 129
<211> LENGTH: 20
<212> TYPE: RNA
<213> ORGANISM: Artificial Sequence
<220> FEATURE:
<223> OTHER INFORMATION: siRNA

<400> SEQUENCE: 129
aaccagaaga agcaggugac                                                    20

<210> SEQ ID NO 130
<211> LENGTH: 20
<212> TYPE: RNA
<213> ORGANISM: Artificial Sequence
<220> FEATURE:
<223> OTHER INFORMATION: siRNA

<400> SEQUENCE: 130
ucaccugcuu cuucugguuc                                                    20

<210> SEQ ID NO 131
<211> LENGTH: 20
<212> TYPE: RNA
<213> ORGANISM: Artificial Sequence
<220> FEATURE:
<223> OTHER INFORMATION: siRNA

<400> SEQUENCE: 131
aaccagaaga agcaggugag                                                    20

<210> SEQ ID NO 132
<211> LENGTH: 20
<212> TYPE: RNA
<213> ORGANISM: Artificial Sequence
<220> FEATURE:
<223> OTHER INFORMATION: siRNA

<400> SEQUENCE: 132
ucaccugcuu cuucugguug                                                    20

<210> SEQ ID NO 133
<211> LENGTH: 19
<212> TYPE: RNA
<213> ORGANISM: Artificial Sequence
<220> FEATURE:
<223> OTHER INFORMATION: siRNA

<400> SEQUENCE: 133
aaccagaaga agcaggugu                                                     19

<210> SEQ ID NO 134
<211> LENGTH: 19
<212> TYPE: RNA
<213> ORGANISM: Artificial Sequence
<220> FEATURE:
<223> OTHER INFORMATION: siRNA

<400> SEQUENCE: 134
aaccagaaga agcaggugc                                                     19
```

<210> SEQ ID NO 135
<211> LENGTH: 19
<212> TYPE: RNA
<213> ORGANISM: Artificial Sequence
<220> FEATURE:
<223> OTHER INFORMATION: siRNA

<400> SEQUENCE: 135
aaccagaaga agcaggugg                                                19

<210> SEQ ID NO 136
<211> LENGTH: 19
<212> TYPE: RNA
<213> ORGANISM: Artificial Sequence
<220> FEATURE:
<223> OTHER INFORMATION: siRNA

<400> SEQUENCE: 136
ucaccugcuu cuucuggua                                                19

<210> SEQ ID NO 137
<211> LENGTH: 19
<212> TYPE: RNA
<213> ORGANISM: Artificial Sequence
<220> FEATURE:
<223> OTHER INFORMATION: siRNA

<400> SEQUENCE: 137
ucaccugcuu cuucugguc                                                19

<210> SEQ ID NO 138
<211> LENGTH: 19
<212> TYPE: RNA
<213> ORGANISM: Artificial Sequence
<220> FEATURE:
<223> OTHER INFORMATION: siRNA

<400> SEQUENCE: 138
ucaccugcuu cuucuggug                                                19

<210> SEQ ID NO 139
<211> LENGTH: 19
<212> TYPE: RNA
<213> ORGANISM: Artificial Sequence
<220> FEATURE:
<223> OTHER INFORMATION: siRNA

<400> SEQUENCE: 139
aauguuuccc ugcugacgg                                                19

<210> SEQ ID NO 140
<211> LENGTH: 19
<212> TYPE: RNA
<213> ORGANISM: Artificial Sequence
<220> FEATURE:
<223> OTHER INFORMATION: siRNA

<400> SEQUENCE: 140
ccgucagcag gaaaacauu                                                19

<210> SEQ ID NO 141
<211> LENGTH: 20
<212> TYPE: RNA
<213> ORGANISM: Artificial Sequence
<220> FEATURE:

<223> OTHER INFORMATION: siRNA

<400> SEQUENCE: 141
aauguuuucc ugcugacgga                                              20

<210> SEQ ID NO 142
<211> LENGTH: 20
<212> TYPE: RNA
<213> ORGANISM: Artificial Sequence
<220> FEATURE:
<223> OTHER INFORMATION: siRNA

<400> SEQUENCE: 142
ccgucagcag gaaaacauua                                              20

<210> SEQ ID NO 143
<211> LENGTH: 20
<212> TYPE: RNA
<213> ORGANISM: Artificial Sequence
<220> FEATURE:
<223> OTHER INFORMATION: siRNA

<400> SEQUENCE: 143
aauguuuucc ugcugacggu                                              20

<210> SEQ ID NO 144
<211> LENGTH: 20
<212> TYPE: RNA
<213> ORGANISM: Artificial Sequence
<220> FEATURE:
<223> OTHER INFORMATION: siRNA

<400> SEQUENCE: 144
ccgucagcag gaaaacauuu                                              20

<210> SEQ ID NO 145
<211> LENGTH: 20
<212> TYPE: RNA
<213> ORGANISM: Artificial Sequence
<220> FEATURE:
<223> OTHER INFORMATION: siRNA

<400> SEQUENCE: 145
aauguuuucc ugcugacggc                                              20

<210> SEQ ID NO 146
<211> LENGTH: 20
<212> TYPE: RNA
<213> ORGANISM: Artificial Sequence
<220> FEATURE:
<223> OTHER INFORMATION: siRNA

<400> SEQUENCE: 146
ccgucagcag gaaaacauuc                                              20

<210> SEQ ID NO 147
<211> LENGTH: 20
<212> TYPE: RNA
<213> ORGANISM: Artificial Sequence
<220> FEATURE:
<223> OTHER INFORMATION: siRNA

<400> SEQUENCE: 147
aauguuuucc ugcugacggg                                              20

```
<210> SEQ ID NO 148
<211> LENGTH: 20
<212> TYPE: RNA
<213> ORGANISM: Artificial Sequence
<220> FEATURE:
<223> OTHER INFORMATION: siRNA

<400> SEQUENCE: 148
ccgucagcag gaaaacauug                                                     20

<210> SEQ ID NO 149
<211> LENGTH: 19
<212> TYPE: RNA
<213> ORGANISM: Artificial Sequence
<220> FEATURE:
<223> OTHER INFORMATION: siRNA

<400> SEQUENCE: 149
aauguuuccc ugcugacga                                                      19

<210> SEQ ID NO 150
<211> LENGTH: 19
<212> TYPE: RNA
<213> ORGANISM: Artificial Sequence
<220> FEATURE:
<223> OTHER INFORMATION: siRNA

<400> SEQUENCE: 150
ccgucagcag gaaaacaua                                                      19

<210> SEQ ID NO 151
<211> LENGTH: 19
<212> TYPE: RNA
<213> ORGANISM: Artificial Sequence
<220> FEATURE:
<223> OTHER INFORMATION: siRNA

<400> SEQUENCE: 151
aauguuuccc ugcugacgu                                                      19

<210> SEQ ID NO 152
<211> LENGTH: 19
<212> TYPE: RNA
<213> ORGANISM: Artificial Sequence
<220> FEATURE:
<223> OTHER INFORMATION: siRNA

<400> SEQUENCE: 152
aauguuuccc ugcugacgc                                                      19

<210> SEQ ID NO 153
<211> LENGTH: 19
<212> TYPE: RNA
<213> ORGANISM: Artificial Sequence
<220> FEATURE:
<223> OTHER INFORMATION: siRNA

<400> SEQUENCE: 153
ccgucagcag gaaaacauc                                                      19

<210> SEQ ID NO 154
<211> LENGTH: 19
<212> TYPE: RNA
<213> ORGANISM: Artificial Sequence
<220> FEATURE:
<223> OTHER INFORMATION: siRNA
```

-continued

<400> SEQUENCE: 154
ccgucagcag gaaaacaug                                                 19

<210> SEQ ID NO 155
<211> LENGTH: 19
<212> TYPE: RNA
<213> ORGANISM: Artificial Sequence
<220> FEATURE:
<223> OTHER INFORMATION: siRNA

<400> SEQUENCE: 155
ucuucuuaaa cugaguuuc                                                 19

<210> SEQ ID NO 156
<211> LENGTH: 19
<212> TYPE: RNA
<213> ORGANISM: Artificial Sequence
<220> FEATURE:
<223> OTHER INFORMATION: siRNA

<400> SEQUENCE: 156
gaaacucagu uuaagaaga                                                 19

<210> SEQ ID NO 157
<211> LENGTH: 19
<212> TYPE: RNA
<213> ORGANISM: Artificial Sequence
<220> FEATURE:
<223> OTHER INFORMATION: siRNA

<400> SEQUENCE: 157
auguagccga ggaucuucu                                                 19

<210> SEQ ID NO 158
<211> LENGTH: 19
<212> TYPE: RNA
<213> ORGANISM: Artificial Sequence
<220> FEATURE:
<223> OTHER INFORMATION: siRNA

<400> SEQUENCE: 158
agaagauccu cggcuacau                                                 19

<210> SEQ ID NO 159
<211> LENGTH: 21
<212> TYPE: RNA
<213> ORGANISM: Artificial Sequence
<220> FEATURE:
<223> OTHER INFORMATION: siRNA

<400> SEQUENCE: 159
uuauagagca agaacacugu u                                              21

<210> SEQ ID NO 160
<211> LENGTH: 21
<212> TYPE: RNA
<213> ORGANISM: Artificial Sequence
<220> FEATURE:
<223> OTHER INFORMATION: siRNA

<400> SEQUENCE: 160
aacaguguuc uugcucuaua a                                              21

<210> SEQ ID NO 161
<211> LENGTH: 19

```
<212> TYPE: RNA
<213> ORGANISM: Artificial Sequence
<220> FEATURE:
<223> OTHER INFORMATION: siRNA

<400> SEQUENCE: 161
aauguuuucc ugcugacgg                                                  19

<210> SEQ ID NO 162
<211> LENGTH: 19
<212> TYPE: RNA
<213> ORGANISM: Artificial Sequence
<220> FEATURE:
<223> OTHER INFORMATION: siRNA

<400> SEQUENCE: 162
ccgucagcag gaaaacauu                                                  19

<210> SEQ ID NO 163
<211> LENGTH: 19
<212> TYPE: RNA
<213> ORGANISM: Artificial Sequence
<220> FEATURE:
<223> OTHER INFORMATION: siRNA

<400> SEQUENCE: 163
aauguuuucc ugcugacga                                                  19

<210> SEQ ID NO 164
<211> LENGTH: 19
<212> TYPE: RNA
<213> ORGANISM: Artificial Sequence
<220> FEATURE:
<223> OTHER INFORMATION: siRNA

<400> SEQUENCE: 164
ccgucagcag gaaaacaua                                                  19

<210> SEQ ID NO 165
<211> LENGTH: 19
<212> TYPE: RNA
<213> ORGANISM: Artificial Sequence
<220> FEATURE:
<223> OTHER INFORMATION: siRNA

<400> SEQUENCE: 165
agaagauccu cggcuacaa                                                  19

<210> SEQ ID NO 166
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 166
ucgaaguauu ccgcguacg                                                  19

<210> SEQ ID NO 167
<211> LENGTH: 19
<212> TYPE: RNA
<213> ORGANISM: Artificial Sequence
<220> FEATURE:
<223> OTHER INFORMATION: siRNA
```

```
-continued

<220> FEATURE:
<223> OTHER INFORMATION: modified_base, modified as per summary sequence
      table at the end of the description

<400> SEQUENCE: 167
cguacgcgga auacuucga                                                  19

<210> SEQ ID NO 168
<211> LENGTH: 21
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 168
uuauagagca agaacacugu u                                               21

<210> SEQ ID NO 169
<211> LENGTH: 21
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 169
aacaguguuc uugcucuaua a                                               21

<210> SEQ ID NO 170
<211> LENGTH: 21
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 170
uuauagagca agaacacugu u                                               21

<210> SEQ ID NO 171
<211> LENGTH: 21
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 171
aacaguguuc uugcucuaua a                                               21

<210> SEQ ID NO 172
<211> LENGTH: 21
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description
```

```
<400> SEQUENCE: 172
auauagagca agaacacugu u                                              21

<210> SEQ ID NO 173
<211> LENGTH: 21
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 173
aacaguguuc uugcucuaua a                                              21

<210> SEQ ID NO 174
<211> LENGTH: 21
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 174
guauagagca agaacacugu u                                              21

<210> SEQ ID NO 175
<211> LENGTH: 21
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 175
aacaguguuc uugcucuaua a                                              21

<210> SEQ ID NO 176
<211> LENGTH: 21
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 176
uuauagagca agaacacugu u                                              21

<210> SEQ ID NO 177
<211> LENGTH: 21
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 177
aacaguguuc uugcucuaua a                                              21
```

<210> SEQ ID NO 178
<211> LENGTH: 21
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 178
cuauagagca agaacacugu u                                             21

<210> SEQ ID NO 179
<211> LENGTH: 21
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 179
aacaguguuc uugcucuaua a                                             21

<210> SEQ ID NO 180
<211> LENGTH: 21
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 180
uuauagagca agaacacugu u                                             21

<210> SEQ ID NO 181
<211> LENGTH: 22
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 181
aaacaguguu cuugcucuau aa                                            22

<210> SEQ ID NO 182
<211> LENGTH: 21
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 182
uuauagagca agaacacugu u                                             21

<210> SEQ ID NO 183
<211> LENGTH: 22
<212> TYPE: RNA

```
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 183
gaacaguguu cuugcucuau aa                                              22

<210> SEQ ID NO 184
<211> LENGTH: 21
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 184
uuauagagca agaacacugu u                                               21

<210> SEQ ID NO 185
<211> LENGTH: 22
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 185
uaacaguguu cuugcucuau aa                                              22

<210> SEQ ID NO 186
<211> LENGTH: 21
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 186
uuauagagca agaacacugu u                                               21

<210> SEQ ID NO 187
<211> LENGTH: 22
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per summary sequence
      table at the end of the description

<400> SEQUENCE: 187
caacaguguu cuugcucuau aa                                              22

<210> SEQ ID NO 188
<211> LENGTH: 19
<212> TYPE: RNA
<213> ORGANISM: Artificial Sequence
<220> FEATURE:
<223> OTHER INFORMATION: siRNA
```

```
<400> SEQUENCE: 188
ucgaaguauu ccgcguacg                                                19

<210> SEQ ID NO 189
<211> LENGTH: 19
<212> TYPE: RNA
<213> ORGANISM: Artificial Sequence
<220> FEATURE:
<223> OTHER INFORMATION: siRNA

<400> SEQUENCE: 189
cguacgcgga auacuucga                                                19

<210> SEQ ID NO 190
<211> LENGTH: 21
<212> TYPE: RNA
<213> ORGANISM: Artificial Sequence
<220> FEATURE:
<223> OTHER INFORMATION: siRNA

<400> SEQUENCE: 190
uuauagagca agaacacugu u                                             21

<210> SEQ ID NO 191
<211> LENGTH: 21
<212> TYPE: RNA
<213> ORGANISM: Artificial Sequence
<220> FEATURE:
<223> OTHER INFORMATION: siRNA

<400> SEQUENCE: 191
auauagagca agaacacugu u                                             21

<210> SEQ ID NO 192
<211> LENGTH: 21
<212> TYPE: RNA
<213> ORGANISM: Artificial Sequence
<220> FEATURE:
<223> OTHER INFORMATION: siRNA

<400> SEQUENCE: 192
guauagagca agaacacugu u                                             21

<210> SEQ ID NO 193
<211> LENGTH: 21
<212> TYPE: RNA
<213> ORGANISM: Artificial Sequence
<220> FEATURE:
<223> OTHER INFORMATION: siRNA

<400> SEQUENCE: 193
cuauagagca agaacacugu u                                             21

<210> SEQ ID NO 194
<211> LENGTH: 21
<212> TYPE: RNA
<213> ORGANISM: Artificial Sequence
<220> FEATURE:
<223> OTHER INFORMATION: siRNA

<400> SEQUENCE: 194
aacaguguuc uugcucuaua a                                             21

<210> SEQ ID NO 195
<211> LENGTH: 22
```

```
<212> TYPE: RNA
<213> ORGANISM: Artificial Sequence
<220> FEATURE:
<223> OTHER INFORMATION: siRNA

<400> SEQUENCE: 195
aaacaguguu cuugcucuau aa                                              22

<210> SEQ ID NO 196
<211> LENGTH: 22
<212> TYPE: RNA
<213> ORGANISM: Artificial Sequence
<220> FEATURE:
<223> OTHER INFORMATION: siRNA

<400> SEQUENCE: 196
gaacaguguu cuugcucuau aa                                              22

<210> SEQ ID NO 197
<211> LENGTH: 22
<212> TYPE: RNA
<213> ORGANISM: Artificial Sequence
<220> FEATURE:
<223> OTHER INFORMATION: siRNA

<400> SEQUENCE: 197
uaacaguguu cuugcucuau aa                                              22

<210> SEQ ID NO 198
<211> LENGTH: 22
<212> TYPE: RNA
<213> ORGANISM: Artificial Sequence
<220> FEATURE:
<223> OTHER INFORMATION: siRNA

<400> SEQUENCE: 198
caacaguguu cuugcucuau aa                                              22

<210> SEQ ID NO 199
<211> LENGTH: 18
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per Table 4

<400> SEQUENCE: 199
aauguuuccu gcugacgg                                                   18

<210> SEQ ID NO 200
<211> LENGTH: 18
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per Table 4

<400> SEQUENCE: 200
aauguuuccu gcugacgg                                                   18

<210> SEQ ID NO 201
<211> LENGTH: 18
<212> TYPE: RNA
<213> ORGANISM: Artificial Sequence
<220> FEATURE:
```

```
<223> OTHER INFORMATION: siRNA
<220> FEATURE:
<223> OTHER INFORMATION: modified_base, modified as per Table 4

<400> SEQUENCE: 201 aauguuccu gcugacgg                                                      18

<210> SEQ ID NO 202
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per Table 4

<400> SEQUENCE: 202 aauguuccu gcugacgga                                                     19

<210> SEQ ID NO 203
<211> LENGTH: 19
<212> TYPE: RNA
<213> ORGANISM: Artificial Sequence
<220> FEATURE:
<223> OTHER INFORMATION: siRNA
<220> FEATURE:
<223> OTHER INFORMATION: modified_base, modified as per Table 4

<400> SEQUENCE: 203 aauguuccu gcugacggg                                                     19

<210> SEQ ID NO 204
<211> LENGTH: 13
<212> TYPE: PRT
<213> ORGANISM: Artificial Sequence
<220> FEATURE:
<223> OTHER INFORMATION: HIV Tat protein

<400> SEQUENCE: 204

Gly Arg Lys Lys Arg Arg Gln Arg Arg Arg Pro Pro Gln
1               5                   10

<210> SEQ ID NO 205
<211> LENGTH: 16
<212> TYPE: PRT
<213> ORGANISM: Artificial Sequence
<220> FEATURE:
<223> OTHER INFORMATION: Drosophila antennapedia

<400> SEQUENCE: 205

Arg Gln Ile Lys Ile Trp Phe Gln Asn Arg Arg Met Lys Trp Lys Lys
1               5                   10                  15
```

PRODUCTS AND COMPOSITIONS

CROSS REFERENCE TO RELATED APPLICATIONS

This application is a national stage application under 35 U.S.C. § 371 of International Application No. PCT/EP2018/058762, filed internationally Apr. 5, 2018, which claims the benefit of priority to European Patent Application No. 17165058.3, filed Apr. 5, 2017, European Patent Application No. 17201353.4, filed Nov. 13, 2017 and 17201447.4, filed Nov. 13, 2017 the disclosures of which are incorporated herein by reference in their entirety.

PRODUCTS AND COMPOSTIONS

The present invention relates to products and compositions and their uses. In particular the invention relates to nucleic acid products that interfere with target gene expression or inhibit target gene expression and therapeutic uses of such products.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 680132000600SUBSEQLIST.TXT, date recorded: Nov. 19, 2020, size: 50 KB).

BACKGROUND

Double-stranded RNA (dsRNA) able to complementarily bind expressed mRNA has been shown to be able to block gene expression (Fire et al, 1998 and Elbashir et al, 2001) by a mechanism that has been termed RNA interference (RNAi). Short dsRNAs direct gene-specific, post-transcriptional silencing in many organisms, including vertebrates, and have become a useful tool for studying gene function. RNAi is mediated by the RNA-induced silencing complex (RISC), a sequence-specific, multi-component nuclease that destroys messenger RNAs homologous to the silencing trigger loaded into the RISC complex. Interfering RNA (iRNA) such as siRNAs, antisense RNA, and micro-RNA are oligonucleotides that prevent the formation of proteins by gene-silencing i.e. inhibiting gene translation of the protein through degradation of mRNA molecules. Gene-silencing agents are becoming increasingly important for therapeutic applications in medicine.

According to Watts and Corey in the Journal of Pathology (2012; Vol 226, p 365-379) there are algorithms that can be used to design nucleic acids but none is perfect. It may take various experimental methods to identify potent siRNAs, as algorithms do not take into account factors such as tertiary structure or the involvement of RNA binding proteins. Therefore the discovery of a potent nucleic acid with minimal off-target effects is a complex process. For the pharmaceutical development of these highly charged molecules it is necessary that they can be synthesised economically, distributed to target tissues, enter cells and function within acceptable limits of toxicity.

However, delivery of nucleic acids, such as RNA, to cells avoiding degradation by cellular nucleases, whilst maintaining efficacy and target specificity has proved challenging to those in the field of developing nucleic acid molecules for therapeutic use.

Thus, means for efficient delivery of oligonucleotides, in particular double stranded siRNAs, to cells in vivo is becoming increasingly important and requires specific targeting and substantial protection from the extracellular environment, particularly serum proteins. One method of achieving specific targeting is to conjugate a targeting moiety to the iRNA duplex agent. The targeting moiety helps in targeting the iRNA duplex agent to the required target site and there is a need to design appropriate targeting moieties for the desired receptor sites for the conjugated molecules to be taken up by the cells such as by endocytosis.

However, targeting ligands developed so far do not always translate to in vivo settings and there is a clear need for more efficacious receptor specific ligand conjugated iRNA duplex agents and methods for their preparation for the in vivo delivery of oligonucleotide therapeutics, nucleic acids and double stranded siRNAs.

Rather than a lipid delivery system alone, the present invention addresses the structure of the nucleic acid itself. It has been unexpectedly found that a nucleic acid in accordance with the present invention has increased stability, which prevents degradation of the nucleic acid before entry into a cell.

SUMMARY OF INVENTION

A first aspect of the invention relates to a nucleic acid for inhibiting expression of a target gene in a cell, comprising at least one duplex region that comprises at least a portion of a first strand and at least a portion of a second strand that is at least partially complementary to the first strand, wherein said first strand is at least partially complementary to at least a portion of RNA transcribed from said target gene to be inhibited and wherein the terminal nucleotide at the 3' end of at least one of the first strand and the second strand is an inverted nucleotide and is attached to the adjacent nucleotide via the 3' carbon of the terminal nucleotide and the 3' carbon of the adjacent nucleotide and/or the terminal nucleotide at the 5' end of at least one of the first strand and the second strand is an inverted nucleotide and is attached to the adjacent nucleotide via the 5' carbon of the terminal nucleotide and the 5' carbon of the adjacent nucleotide.

The 3' and/or 5' inverted nucleotide of the first and/or second strand may be attached to the adjacent nucleotide via a phosphate group by way of a phosphodiester linkage.

The 3' and/or 5' inverted nucleotide of the first and/or second strand may be attached to the adjacent nucleotide via a phosphorothioate group. The 3' and/or 5' inverted nucleotide of the first and/or second strand may be attached to the adjacent nucleotide via a phosphorodithioate group.

The 3' and/or 5' inverted nucleotide of the first and/or second strand may be an A or a G.

The 3' and/or 5' inverted nucleotide of the first and/or second strand may form an overhang.

The 3' and/or 5' inverted nucleotide of the first and/or second strand may form a blunt end.

The first strand and second strand of the nucleic acid may be separate strands. The nucleic acid may comprise a single strand that comprises the first strand and the second strand.

The first strand and/or said second strand may be each from 17-35 nucleotides in length and the at least one duplex region may consist of 19-25 nucleotide base pairs.

The nucleic acid may: a) be blunt ended at both ends; b) have an overhang at one end and a blunt end at the other; or c) have an overhang at both ends.

One or more nucleotides on the first and/or second strand may be modified, to form modified nucleotides. One or more of the odd numbered nucleotides of the first strand may be modified. One or more of the even numbered nucleotides of the first strand may be modified by at least a second modification, wherein the at least second modification is different from the modification on the one or more odd numbered nucleotides. At least one of the one or more modified even numbered nucleotides may be adjacent to at least one of the one or more modified odd numbered nucleotides.

A plurality of odd numbered nucleotides may be modified in the nucleic acid of the invention. A plurality of even numbered nucleotides may be modified by a second modification. The first strand may comprise adjacent nucleotides that are modified by a common modification. The first strand may also comprise adjacent nucleotides that are modified by a second different modification.

One or more of the odd numbered nucleotides of the second strand may be modified by a modification that is different to the modification on the odd nucleotides of the first strand and/or one or more of the even numbered nucleotides of the second strand may be modified by the same modification on the odd nucleotides of the first strand. At least one of the one or more modified even numbered nucleotides of the second strand may be adjacent to the one or more modified odd numbered nucleotides. A plurality of odd numbered nucleotides of the second strand may be modified by a common modification and/or a plurality of even numbered nucleotides may be modified by the same modification that is present on the first strand odd numbered nucleotides. A plurality of odd numbered nucleotides may be modified by a second modification, wherein the second modification is different to the modification on the first strand odd numbered nucleotides.

The second strand may comprise adjacent nucleotides that are modified by a common modification, which may be a second modification that is different from the modification on the odd numbered nucleotides of the first strand.

In the nucleic acid of the invention, each of the odd numbered nucleotides in the first strand and each of the even numbered nucleotides in the second strand may be modified with a common modification, and each of the even numbered nucleotides may be modified in the first strand with a second modification and each of the odd numbered nucleotides may be modified in the second strand with a second modification.

The nucleic acid of the invention may have the modified nucleotides of the first strand shifted by at least one nucleotide relative to the unmodified or differently modified nucleotides of the second strand.

The first strand may comprise a sequence selected form the group consisting of SEQ ID NO:s 1, 3, 5 and 7 and/or the second strand may comprise a sequence selected from the group consisting of SEQ ID NO:s 2, 4, 6 and 8.

The modification and/or modifications may each and individually be selected from the group consisting of 3-terminal deoxy-thymine, 2'-O-methyl, a 2'-deoxy-modification, a 2'-amino-modification, a 2'-alkyl-modification, a morpholino modification, a phosphoramidate modification, 5'-phosphorothioate group modification, a 5' phosphate or 5' phosphate mimic modification and a cholesteryl derivative or a dodecanoic acid bisdecylamide group modification and/or the modified nucleotide may be any one of a locked nucleotide, an abasic nucleotide or a non-natural base comprising nucleotide. At least one modification may be 2'-O-methyl and/or at least one modification may be 2'-F.

In the nucleic acid of the invention, the inverted nucleotide that is the terminal nucleotide at the 3' end of at least one of the first strand and the second strand that is attached to the adjacent nucleotide via the 3' carbon of the terminal nucleotide and the 3' carbon of the adjacent nucleotide and/or the inverted nucleotide that is the terminal nucleotide at the 5' end of at least one of the first strand and the second strand that is attached to the adjacent nucleotide via the 5' carbon of the terminal nucleotide and the 5' carbon of the adjacent nucleotide may be a purine.

The nucleic acid of the invention may be conjugated with a ligand.

A nucleic acid of the invention may comprise a phosphorothioate linkage between the terminal one, two or three 3' nucleotides and/or 5' nucleotides of the first and/or the second strand. It may comprise two phosphorothioate linkages between each of the three terminal 3' and between each of the three terminal 5' nucleotides on the first strand, and two phosphorothioate linkages between the three terminal nucleotides of the 3' end of the second strand.

The invention further provides, as a second aspect, a nucleic acid for inhibiting expression of a target gene in a cell, comprising at least one duplex region that comprises at least a portion of a first strand and at least a portion of a second strand that is at least partially complementary to the first strand, wherein said first strand is at least partially complementary to at least a portion of a RNA transcribed from said target gene to be inhibited and wherein the terminal nucleotide at the 3' end of at least one of the first strand and the second strand is an inverted nucleotide and is attached to the adjacent nucleotide via the 3' carbon of the terminal nucleotide and the 3' carbon of the adjacent nucleotide and/or the terminal nucleotide at the 5' end of at least one of the first strand and the second strand is an inverted nucleotide and is attached to the adjacent nucleotide via the 5' carbon of the terminal nucleotide and the 5' carbon of the adjacent nucleotide, and wherein the nucleic acid molecule is conjugated to a ligand.

A ligand for use in the present invention may therefore comprise (i) one or more N-acetyl galactosamine (GalNac) moieties and derivatives thereof, and (ii) a linker, wherein the linker conjugates the GalNac moieties to a sequence as defined in any preceding aspects. The linker may be a bivalent or trivalent or tetravalent branched structure. The nucleotides may be modified as defined herein.

The ligand may comprise the formula I:

wherein:
S represents a saccharide, wherein the saccharide is N-acetyl galactosamine;
$X^1$ represents $C_3$-$C_6$ alkylene or (—$CH_2$—$CH_2$—O$)_m$(—$CH_2$$)_2$— wherein m is 1, 2, or 3;
P is a phosphate or modified phosphate (preferably a thiophosphate);
$X^2$ is alkylene or an alkylene ether of the formula (—$CH_2$$)_n$—O—$CH_2$— where n=1-6;
A is a branching unit;
$X^3$ represents a bridging unit;
wherein a nucleic acid according to the present invention is conjugated to $X^3$ via a phosphate or modified phosphate (preferably a thiophosphate).

The present invention therefore additionally provides a conjugated nucleic acid having one of the following structures:

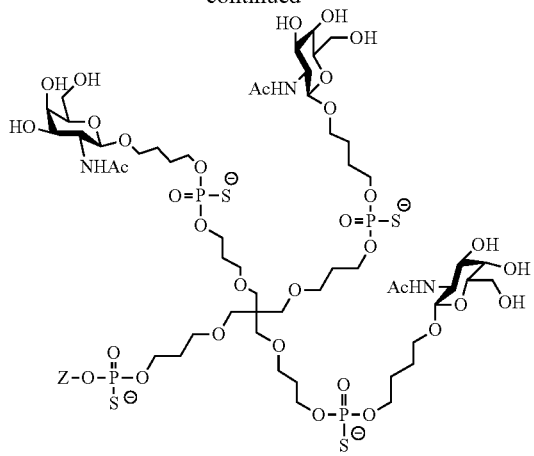

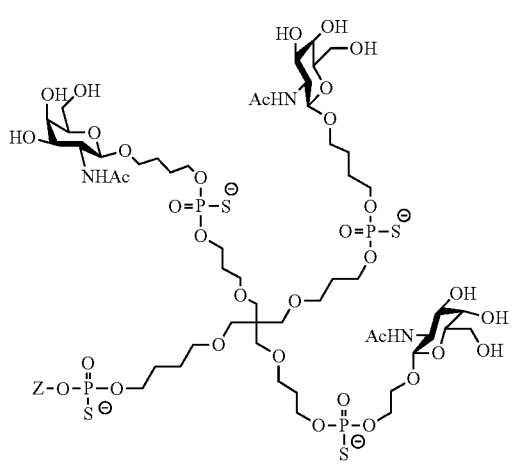

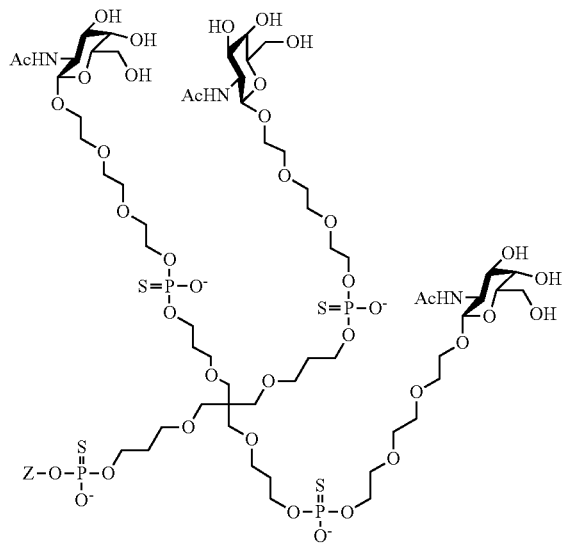

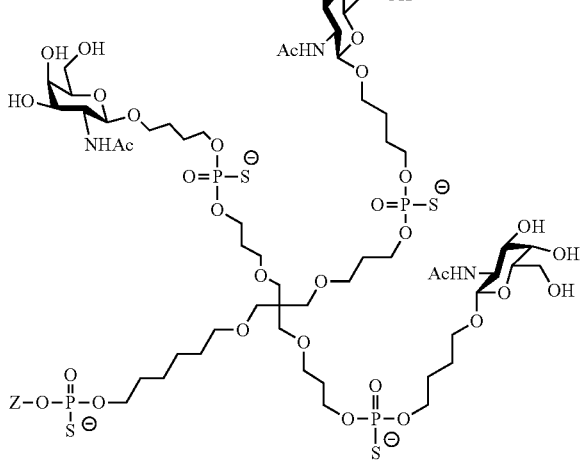

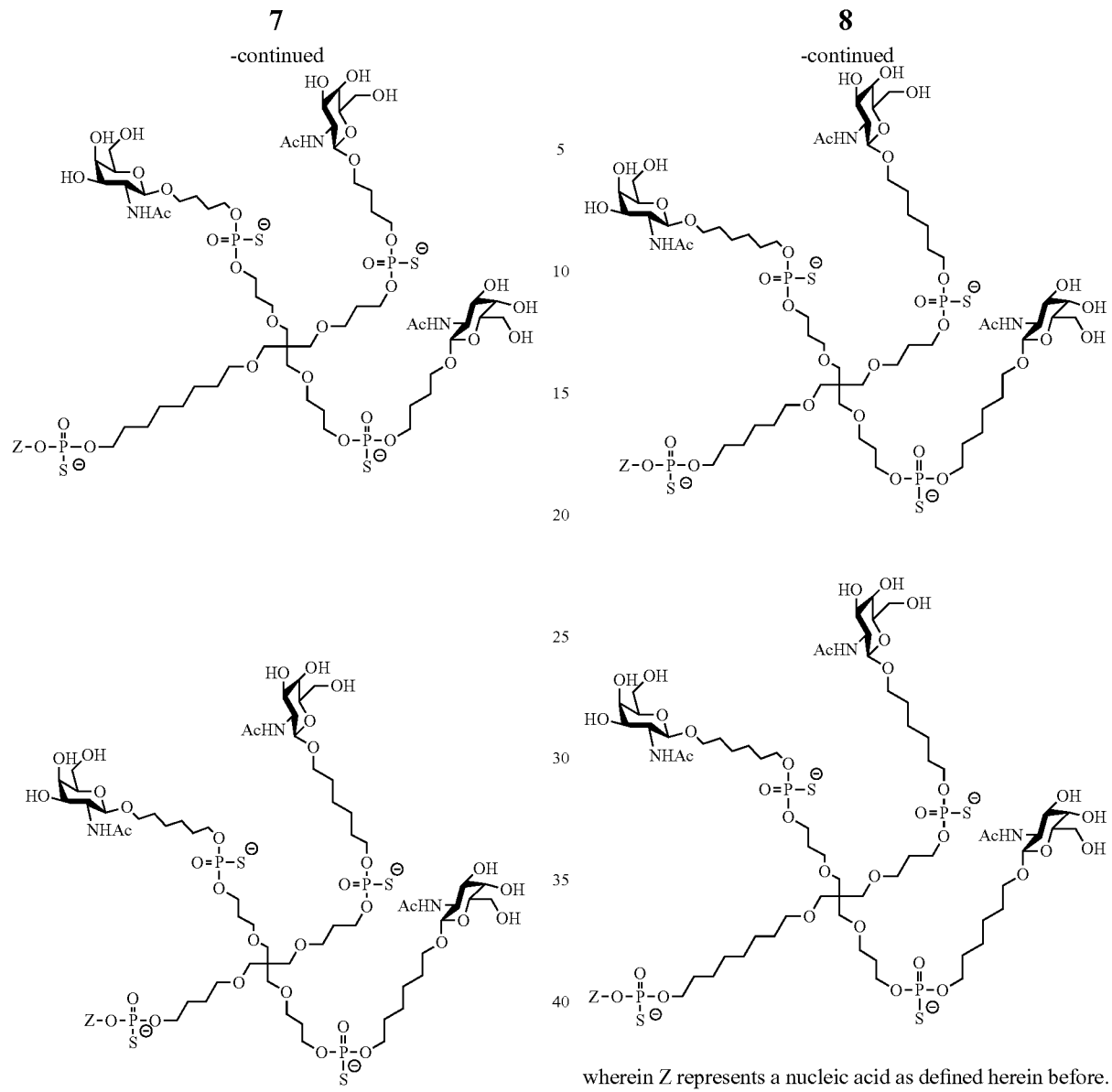
wherein Z represents a nucleic acid as defined herein before. The ligand may comprise:
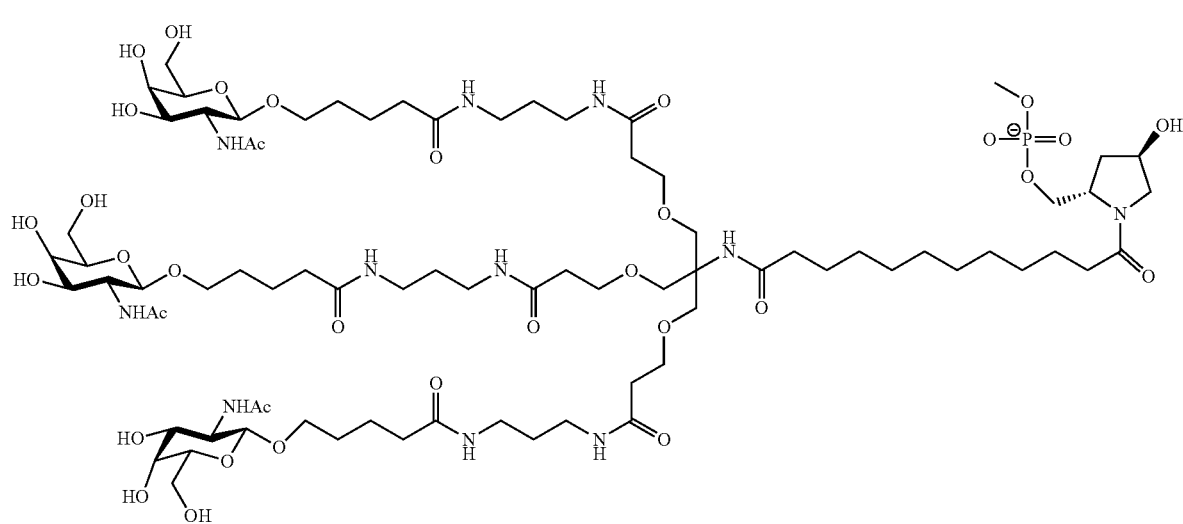

The invention also provides a composition comprising a nucleic acid or conjugated nucleic acid as defined herein and a physiologically acceptable excipient. The composition may include the following excipients:

i) a cationic lipid, or a pharmaceutically acceptable salt thereof;
ii) a steroid;
iii) a phosphatidylethanolamine phospholipid;
iv) a PEGylated lipid.

The content of the cationic lipid component in the composition may be from about 55 mol % to about 65 mol % of the overall lipid content of the lipid formulation, preferably about 59 mol % of the overall lipid content of the lipid composition.

The composition may comprise;
a cationic lipid having the structure;

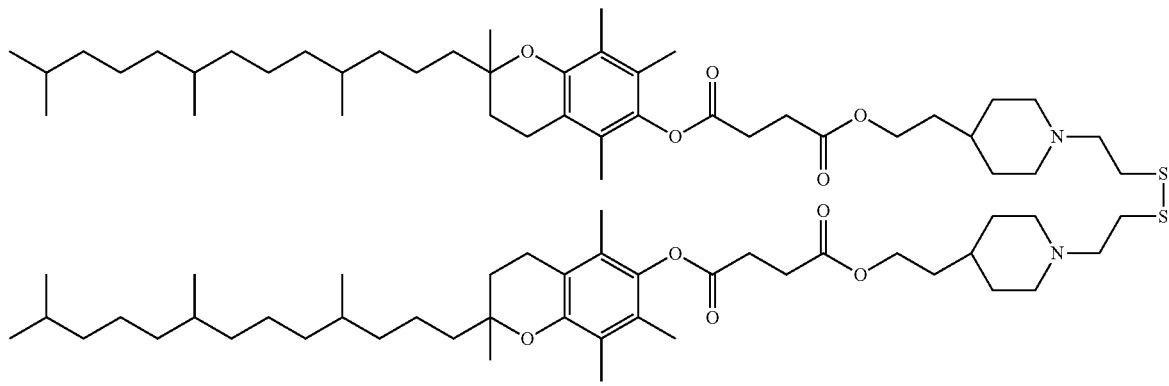 [SMILES: Cc1c(C)c2c(c(C)c1OC(=O)CCC(=O)OCCC1CCN(CCSSCCN3CCC(CCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2]

a steroid having the structure;

Cholesterol a phosphatidylethanolamine phospholipid having the structure;

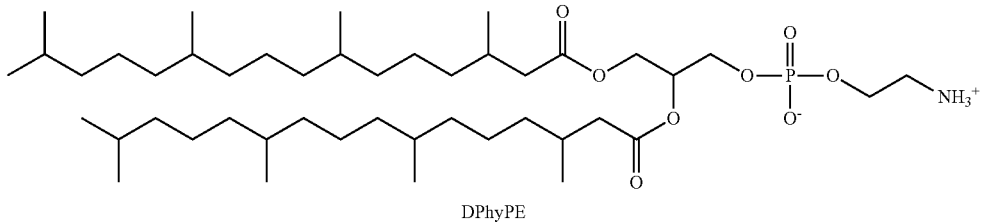 [SMILES: CC(C)CCCC(C)CCCC(C)CCCC(C)CC(=O)OCC(COP(=O)([O-])OCC[NH3+])OC(=O)CC(C)CCCC(C)CCCC(C)CCCC(C)C]

DPhyPE and a PEGylated lipid having the structure;

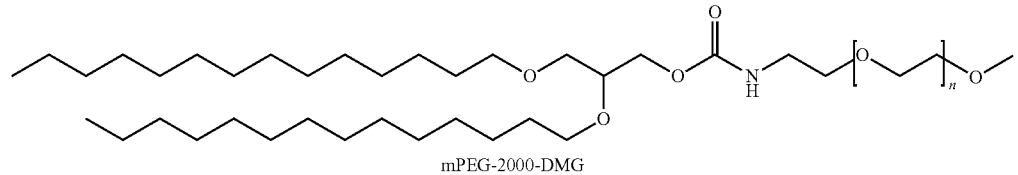

mPEG-2000-DMG

Also provided is a nucleic acid or conjugated nucleic acid according to any aspect of the invention for use in the treatment or prevention of a disease or disorder and/or in the manufacture of a medicament for treating or preventing a disease or disorder.

The invention provides a method of treating or preventing a disease or disorder comprising administration of a composition comprising a nucleic acid or conjugated nucleic acid according to any aspect of the invention to an individual in need of treatment. The nucleic acid may be administered to the subject subcutaneously or intravenously.

A method of making the nucleic acid according to the invention is also included.

DETAILED DESCRIPTION OF INVENTION

The present invention relates to a nucleic acid which is double stranded and directed to an expressed RNA transcript of a target gene and compositions thereof. These nucleic acids can be used in the treatment of a variety of diseases and disorders where reduced expression of target gene products is desirable.

A first aspect of the invention relates to a nucleic acid for inhibiting expression of a target gene in a cell, comprising at least one duplex region that comprises at least a portion of a first strand and at least a portion of a second strand that is at least partially complementary to the first strand, wherein said first strand is at least partially complementary to at least a portion of a RNA transcribed from said target gene to be inhibited and wherein the terminal nucleotide at the 3' end of at least one of the first strand and the second strand is an inverted nucleotide and is attached to the adjacent nucleotide via the 3' carbon of the terminal nucleotide and the 3' carbon of the adjacent nucleotide and/or the terminal nucleotide at the 5' end of at least one of the first strand and the second strand is an inverted nucleotide and is attached to the adjacent nucleotide via the 5' carbon of the terminal nucleotide and the 5' carbon of the adjacent nucleotide.

By nucleic acid it is meant a nucleic acid comprising two strands comprising nucleotides, that is able to interfere with gene expression. Inhibition may be complete or partial and results in down regulation of gene expression in a targeted manner. The nucleic acid comprises two separate polynucleotide strands; the first strand, which may also be a guide strand; and a second strand, which may also be a passenger strand. The first strand and the second strand may be part of the same polynucleotide molecule that is self complementary which 'folds' to form a double stranded molecule. The nucleic acid may be an siRNA molecule.

The nucleic acid may comprise ribonucleotides, modified ribonucleotides, deoxynucleotides, deoxyribonucleotides, or nucleotide analogues. The nucleic acid may further comprise a double-stranded nucleic acid portion or duplex region formed by all or a portion of the first strand (also known in the art as a guide strand) and all or a portion of the second strand (also known in the art as a passenger strand). The duplex region is defined as beginning with the first base pair formed between the first strand and the second strand and ending with the last base pair formed between the first strand and the second strand, inclusive.

By duplex region it is meant the region in two complementary or substantially complementary oligonucleotides that form base pairs with one another, either by Watson-Crick base pairing or any other manner that allows for the formation of a duplex between oligonucleotide strands that are complementary or substantially complementary. For example, an oligonucleotide strand having 21 nucleotide units can base pair with another oligonucleotide of 21 nucleotide units, yet only 19 nucleotides on each strand are complementary or substantially complementary, such that the "duplex region" consists of 19 base pairs. The remaining base pairs may exist as 5' and 3' overhangs, or as single stranded regions. Further, within the duplex region, 100% complementarity is not required; substantial complementarity is allowable within a duplex region. Substantial complementarity refers to complementarity between the strands such that they are capable of annealing under biological conditions. Techniques to empirically determine if two strands are capable of annealing under biological conditions are well known in the art. Alternatively, two strands can be synthesised and added together under biological conditions to determine if they anneal to one another.

The portion of the first strand and second strand that form at least one duplex region may be fully complementary and are at least partially complementary to each other.

Depending on the length of an nucleic acid, a perfect match in terms of base complementarity between the first strand and second strand is not necessarily required. However, the first and second strands must be able to hybridise under physiological conditions.

The complementarity between the first strand and second strand in the at least one duplex region may be perfect in that there are no nucleotide mismatches or additional/deleted nucleotides in either strand. Alternatively, the complementarity may not be perfect. The complementarity may be at least 70%, 75%, 80%, 85%, 90% or 95%.

The first strand and the second strand may each comprise a region of complementarity which comprises at least 15 contiguous nucleotides.

The nucleic acid involves the formation of a duplex region between all or a portion of the first strand and a portion of the target nucleic acid. The portion of the target nucleic acid that forms a duplex region with the first strand, defined as beginning with the first base pair formed between the first strand and the target sequence and ending with the last base pair formed between the first strand and the target sequence, inclusive, is the target nucleic acid sequence or simply, target sequence. The duplex region formed between the first strand and the second strand need not be the same as the duplex region formed between the first strand and the target sequence. That is, the second strand may have a sequence different from the target sequence however, the first strand must be able to form a duplex structure with both the second strand and the target sequence.

The complementarity between the first strand and the target sequence may be perfect (no nucleotide mismatches or additional/deleted nucleotides in either nucleic acid).

The complementarity between the first strand and the target sequence may not be perfect. The complementarity may be from about 70% to about 100%. More specifically, the complementarity may be at least 70%, 80%, 85%, 90% or 95%, or an intermediate value.

The identity between the first strand and the complementary sequence of the target sequence may be from about 75% to about 100%. More specifically, the complementarity may be at least 75%, 80%, 85%, 90% or 95%, or an intermediate value, provided a nucleic acid is capable of reducing or inhibiting the expression of a target gene.

A nucleic acid with less than 100% complementarity between the first strand and the target sequence may be able to reduce the expression of a target gene to the same level as a nucleic acid with perfect complementarity between the first strand and the target sequence. Alternatively, it may be able to reduce expression of a target gene to a level that is 20%, 30%, 40%, 50%, 60%, 70%, 80%, 90% or 100% of the level of expression achieved by the nucleic acid with perfect complementarity.

In a further aspect the nucleic acid as described herein may reduce the expression of a target gene in a cell by at least 10% compared to the level observed in the absence of an inhibitor, which may be the nucleic acid. All preferred features of any of the previous aspects also apply to this aspect. In particular, the expression of a target gene in a cell may be reduced to 90%, 80%, 70%, 60%, 50%, 40%, 30%, 20%, 15%, and intermediate values, than that observed in the absence of an inhibitor (which may be the nucleic acid).

The nucleic acid may comprise a first strand and a second strand that are each from 19-25 nucleotides in length. The first strand and the second strand may be of different lengths.

The nucleic acid may be 15-25 nucleotide pairs in length. The nucleic acid may be 17-23 nucleotide pairs in length. The nucleic acid may be 17-25 nucleotide pairs in length. The nucleic acid may be 23-24 nucleotide pairs in length. The nucleic acid may be 19-21 nucleotide pairs in length. The nucleic acid may be 21-23 nucleotide pairs in length.

The nucleic acid may comprise a duplex region that consists of 19-25 nucleotide base pairs. The duplex region may consist of 17, 18, 19, 20, 21, 22, 23, 24 or 25 base pairs which may be contiguous.

The 3' and/or 5' inverted nucleotide of the first and/or second strand may be attached to the adjacent nucleotide via a phosphate group and be attached via a phosphodiester linkage.

The 3' and/or 5' inverted nucleotide of the first and/or second strand may be attached to the adjacent nucleotide via a phosphorothioate group. The 3' and/or 5' inverted nucleotide of the first and/or second strand may be attached to the adjacent nucleotide via a phosphorodithioate group. A sulphur of the phosphorothioate or phosphorodithioate group may be in place of one or both of the non-linking O of a phosphate group. An S may be in place of a linking O of the phosphate group.

The 3' and/or 5' inverted nucleotide of the first and/or second strand may be any nucleotide (i.e. A, G, C or U. Preferably, it may be an A or a G.

The nucleic acid may be blunt ended at both ends; have an overhang at one end and a blunt end at the other end; or have an overhang at both ends.

An "overhang" as used herein has its normal and customary meaning in the art, i.e. a single stranded portion of a nucleic acid that extends beyond the terminal nucleotide of a complementary strand in a double strand nucleic acid. The term "blunt end" includes double stranded nucleic acid whereby both strands terminate at the same position, regardless of whether the terminal nucleotide(s) are base paired. The terminal nucleotide of a first strand and a second strand at a blunt end may be base paired. The terminal nucleotide of a first strand and a second strand at a blunt end may not be paired. The terminal two nucleotides of an first strand and a second strand at a blunt end may be base paired. The terminal two nucleotides of an first strand and a second strand at a blunt end may not be paired.

The nucleic acid may have an overhang at one end and a blunt end at the other. The nucleic acid may have an overhang at both ends. The nucleic acid may be blunt ended at both ends. The nucleic acid may be blunt ended at the end with the 5'-end of the first strand and the 3-end of the second strand or at the 3'-end of the first strand and the 5'-end of the second strand.

The nucleic acid may comprise an overhang at a 3'- or 5'-end. The nucleic acid may have a 3-overhang on the first strand. The nucleic acid may have a 3-overhang on the second strand. The nucleic acid may have a 5'-overhang on the first strand. The nucleic acid may have a 5'-overhang on the second strand. The nucleic acid may have an overhang at both the 5'-end and 3-end of the first strand. The nucleic acid may have an overhang at both the 5'-end and 3-end of the second strand. The nucleic acid may have a 5' overhang on the first strand and a 3' overhang on the second strand. The nucleic acid may have a 3' overhang on the first strand and a 5' overhang on the second strand. The nucleic acid may have a 3' overhang on the first strand and a 3' overhang on the second strand. The nucleic acid may have a 5' overhang on the first strand and a 5' overhang on the second strand. An inverted nucleotide may form an overhang at either or both ends of the first strand. Ann inverted nucleotide may form an overhang at either or both ends of the second strand. An inverted nucleotide may form an overhang at one and of the first strand and the other end of the second strand.

An overhang at the 3'-end or 5' end of the second strand or the first strand may be selected from consisting of 1, 2, 3, 4 and 5 nucleotides in length. Optionally, an overhang may consist of 1 or 2 nucleotides, which may or may not be modified.

The inverted nucleotide may be added as an additional nucleotide to the end of a nucleic acid, i.e. it may form an overhang. Alternatively, the inverted nucleotide may be added in place of a terminal nucleotide of the nucleic acid, i.e. it may form a blunt end.

Unmodified polynucleotides, particularly ribonucleotides, may be prone to degradation by cellular nucleases, and, as such, modifications/modified nucleotides may be included in the nucleic acid of the invention.

One or more nucleotides on the second and/or first strand of the nucleic acid of the invention may be modified.

Modifications of the nucleic acid of the present invention generally provide a powerful tool in overcoming potential limitations including, but not limited to, in vitro and in vivo stability and bioavailability inherent to native RNA molecules. The nucleic acid according to the invention may be modified by chemical modifications. Modified nucleic acid can also minimise the possibility of inducing interferon activity in humans. Modification can further enhance the functional delivery of a nucleic acid to a target cell. The modified nucleic acid of the present invention may comprise one or more chemically modified ribonucleotides of either or both of the first strand or the second strand. A ribonucleotide may comprise a chemical modification of the base, sugar or phosphate moieties. The ribonucleic acid may be modified by substitution or insertion with analogues of nucleic acids or bases.

One or more nucleotides of a nucleic acid of the present invention may be modified. The nucleic acid may comprise at least one modified nucleotide. The modified nucleotide may be on the first strand. The modified nucleotide may be in the second strand. The modified nucleotide may be in the duplex region. The modified nucleotide may be outside the duplex region, i.e., in a single stranded region. The modified nucleotide may be on the first strand and may be outside the duplex region. The modified nucleotide may be on the second strand and may be outside the duplex region. The 3'-terminal nucleotide of the first strand may be a modified nucleotide. The 3-terminal nucleotide of the second strand may be a modified nucleotide. The 5-terminal nucleotide of the first strand may be a modified nucleotide. The 5-terminal nucleotide of the second strand may be a modified nucleotide.

An nucleic acid of the invention may have 1 modified nucleotide or a nucleic acid of the invention may have about 2-4 modified nucleotides, or a nucleic acid may have about 4-6 modified nucleotides, about 6-8 modified nucleotides, about 8-10 modified nucleotides, about 10-12 modified nucleotides, about 12-14 modified nucleotides, about 14-16 modified nucleotides about 16-18 modified nucleotides, about 18-20 modified nucleotides, about 20-22 modified nucleotides, about 22-24 modified nucleotides, 24-26 modified nucleotides or about 26-28 modified nucleotides. In each case the nucleic acid comprising said modified nucleotides retains at least 50% of its activity as compared to the same nucleic acid but without said modified nucleotides. The nucleic acid may retain 55%, 60%, 65%, 70%, 75%, 80%, 85%, 90%, 95% or 100% or an intermediate value of its activity as compared to the same nucleic acid but without said modified nucleotides, or may have more than 100% of the activity of the same nucleotide without said modified nucleotides.

The modified nucleotide may be a purine or a pyrimidine. At least half of the purines may be modified. At least half of the pyrimidines may be modified. All of the purines may be modified. All of the pyrimidines may be modified. The modified nucleotides may be selected from the group consisting of a 3-terminal deoxy-thymine (dT) nucleotide, a 2'-O-methyl modified nucleotide, a 2' modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, a non-natural base comprising nucleotide, a nucleotide comprising a 5'-phosphorothioate group, a nucleotide comprising a 5' phosphate or 5' phosphate mimic and a terminal nucleotide linked to a cholesteryl derivative or a dodecanoic acid bisdecylamide group.

The nucleic acid may comprise a nucleotide comprising a modified nucleotide, wherein the base is selected from 2-aminoadenosine, 2,6-diaminopurine,inosine, pyridin-4-one, pyridin-2-one, phenyl, pseudouracil, 2, 4, 6-trimethoxy benzene, 3-methyl uracil, dihydrouridine, naphthyl, aminophenyl, 5-alkylcytidine (e.g., 5-methylcytidine), 5-alkyluridine (e.g., ribothymidine), 5-halouridine (e.g., 5-bromouridine), 6-azapyrimidine, 6-alkylpyrimidine (e.g. 6-methyluridine), propyne, quesosine, 2-thiouridine, 4-thiouridine, wybutosine, wybutoxosine, 4-acetylcytidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N6-isopentenyladenosine, beta-D-mannosylqueosine, uridine-5-oxyacetic acid and 2-thiocytidine.

Nucleic acids discussed herein include unmodified RNA as well as RNA which has been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, for example as occur naturally in the human body. Modified nucleotide as used herein refers to a nucleotide in which one or more of the components of the nucleic acid, namely sugars, bases, and phosphate moieties, are different from that which occur in nature. While they are referred to as modified nucleotides they will of course, because of the modification, include molecules which are not nucleotides, for example a polynucleotide molecules in which the ribophosphate backbone is replaced with a non-ribophosphate construct that allows hybridisation between strands i.e. the modified nucleotides mimic the ribophosphate backbone.

Many of the modifications described below that occur within a nucleic acid will be repeated within a polynucleotide molecule, such as a modification of a base, or a phosphate moiety, or the a non-linking O of a phosphate moiety. In some cases the modification will occur at all of the possible positions/nucleotides in the polynucleotide but in many cases it will not. A modification may only occur at a 3' or 5' terminal position, may only occur in a terminal regions, such as at a position on a terminal nucleotide or in the last 2, 3, 4, 5, or 10 nucleotides of a strand. A modification may occur in a double strand region, a single strand region, or in both. A modification may occur only in the double strand region of a nucleic acid of the invention or may only occur in a single strand region of an nucleic acid of the invention. A phosphorothioate modification at a non-linking O position may only occur at one or both termini, may only occur in a terminal region, e.g., at a position on a terminal nucleotide or in the last 2, 3, 4 or 5 nucleotides of a strand, or may occur in duplex and/or in single strand regions, particularly at termini. The 5' end or 3' ends may be phosphorylated.

Stability of an nucleic acid of the invention may be increased by including particular bases in overhangs, or by including modified nucleotides, in single strand overhangs, e.g., in a 5' or 3' overhang, or in both. Purine nucleotides may be included in overhangs. All or some of the bases in a 3' or 5' overhang may be modified. Modifications can include the use of modifications at the 2' OH group of the ribose sugar, the use of deoxyribonucleotides, instead of ribonucleotides, and modifications in the phosphate group, such as phosphorothioate modifications. Overhangs need not be homologous with the target sequence.

The 5'- or 3'-overhangs at the first strand, second strand or both strands of the dsRNA agent of the invention may be phosphorylated. In some embodiments, the overhang region contains two nucleotides having a phosphorothioate between the two nucleotides, where the two nucleotides can be the same or different. In one embodiment, the overhang is present at the 3'-end of the first strand, second strand or both strands. In one embodiment, this 3'-overhang is present in the first strand. In one embodiment, this 3'-overhang is present in the second strand.

Nucleases can hydrolyze nucleic acid phosphodiester bonds. However, chemical modifications to nucleic acids can confer improved properties, and, can render oligoribonucleotides more stable to nucleases.

Modified nucleic acids, as used herein, can include one or more of:

(i) alteration, e.g., replacement, of one or both of the non-linking phosphate oxygens and/or of one or more of the linking phosphate oxygens (referred to as linking even if at the 5' and 3' terminus of the nucleic acid of the invention);

(ii) alteration, e.g., replacement, of a constituent of the ribose sugar, e.g., of the 2' hydroxyl on the ribose sugar;

(iii) replacement of the phosphate moiety with "dephospho" linkers;

(iv) modification or replacement of a naturally occurring base;

(v) replacement or modification of the ribose-phosphate backbone;

(vi) modification of the 3' end or 5' end of the RNA, e.g., removal, modification or replacement of a terminal phosphate group or conjugation of a moiety, e.g., a fluorescently labeled moiety, to either the 3' or 5' end of RNA.

The terms replacement, modification, alteration, indicates a difference from a naturally occurring molecule.

Specific modifications are discussed in more detail below.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulphur. One, each or both non-linking oxygens in the phosphate group can be independently any one of S, Se, B, C, H, N, or OR (R is alkyl or aryl).

The phosphate linker can also be modified by replacement of a linking oxygen with nitrogen (bridged phosphoroamidates), sulfur (bridged phosphorothioates) and carbon (bridged methylenephosphonates). The replacement can occur at a terminal oxygen. Replacement of the non-linking oxygens with nitrogen is possible.

A modified nucleotide can include modification of the sugar groups. The 2' hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), O(CH2CH2O)nCH2CH2OR; "locked" nucleic acids (LNA) in which the 2' hydroxyl is connected, e.g., by a methylene bridge, to the 4' carbon of the same ribose sugar; O-AMINE (AMINE=NH2; alkylamino, dialkylamino, heterocyclyl, arylamino, diaryl amino, heteroaryl amino, or diheteroaryl amino, ethylene diamine, polyamino) and aminoalkoxy, O(CH2)nAMINE, (e.g., AMINE=NH2; alkylamino, dialkylamino, heterocyclyl, arylamino, diaryl amino, heteroaryl amino, or diheteroaryl amino, ethylene diamine, polyamino).

"Deoxy" modifications include hydrogen halo; amino (e.g., NH2; alkylamino, dialkylamino, heterocyclyl, arylamino, diaryl amino, heteroaryl amino, diheteroaryl amino, or amino acid); NH(CH2CH2NH)nCH2CH2-AMINE (AMINE=NH2; alkylamino, dialkylamino, heterocyclyl, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality. Other substitutents of certain embodiments include 2'-methoxyethyl, 2'-OCH3, 2'-O-allyl, 2'-C-allyl, and 2'-fluoro.

The sugar group can also contain one or more carbons that possess the opposite stereochemical configuration than that of the corresponding carbon in ribose. Thus, a modified nucleotides may contain a sugar such as arabinose.

Modified nucleotides can also include "abasic" sugars, which lack a nucleobase at C—I'. These abasic sugars can further contain modifications at one or more of the constituent sugar atoms.

The 2' modifications may be used in combination with one or more phosphate linker modifications (e.g., phosphorothioate).

The phosphate group can be replaced by non-phosphorus containing connectors.

Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. In certain embodiments, replacements may include the methylenecarbonylamino and methylenemethylimino groups.

The phosphate linker and ribose sugar may be replaced by nuclease resistant nucleotides.

Examples include the morpholino, cyclobutyl, pyrrolidine and peptide nucleic acid (PNA) nucleoside surrogates. In certain embodiments, PNA surrogates may be used.

The 3' and 5' ends of an oligonucleotide can be modified. Such modifications can be at the 3' end or the 5' end or both ends of the molecule. They can include modification or replacement of an entire terminal phosphate or of one or more of the atoms of the phosphate group. For example, the 3' and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a linker. The terminal atom of the linker can connect to or replace the linking atom of the phosphate group or the C-3' or C-5' O, N, S or C group of the sugar. Alternatively, the linker can connect to or replace the terminal atom of a nucleotide surrogate (e.g., PNAs). These spacers or linkers can include e.g., —(CH$_2$)$_n$—, —(CH$_2$)$_n$N—, —(CH$_2$)nO—, —(CH$_2$)$_n$S—, O(CH$_2$CH$_2$O)$_n$CH$_2$CH$_2$OH (e.g., n=3 or 6), abasic sugars, amide, carboxy, amine, oxyamine, oxyimine, thioether, disulfide, thiourea, sulfonamide, or morpholino, or biotin and fluorescein reagents. The 3' end can be an —OH group.

Other examples of terminal modifications include dyes, intercalating agents (e.g., acridines), cross-linkers (e.g., psoralene, mitomycin C), porphyrins (TPPC4, texaphyrin, Sapphyrin), polycyclic aromatic hydrocarbons (e.g., phenazine, dihydrophenazine), artificial endonucleases (e.g., EDTA), lipophilic carriers (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g., biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu$^{3+}$ complexes of tetraazamacrocycles).

Alternative or additional terminal modifications can be added for a number of reasons, including to modulate activity or to modulate resistance to degradation. Terminal modifications useful for modulating activity include modification of the 5' end with phosphate or phosphate analogues. Nucleic acids of the invention, on the first or second strand, may be 5' phosphorylated or include a phosphoryl analogue at the 5' prime terminus. 5'-phosphate modifications include those which are compatible with RISC mediated gene silencing. Suitable modifications include: 5'-monophosphate ((HO)$_2$(O)P—O-5'); 5'-diphosphate ((HO)$_2$(O)P—O—P(HO)(O)—O-5'); 5'-triphosphate ((HO)$_2$(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-

5'-(HO)(O)P—O—(HO)(O)P—O—P(HO)(O)—O-5');
5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)$_2$(O)P—S-5'); any additional combination of oxygen/sulfur replaced monophosphate, diphosphate and triphosphates (e.g., 5'-alpha-thiotriphosphate, 5'-gamma-thiotriphosphate, etc.), 5'-phosphoramidates ((HO)$_2$(O)P—NH-5', (HO)(NH$_2$)(O)P—O-5'), 5'-alkylphosphonates (R=alkyl=methyl, ethyl, isopropyl, propyl, etc., e.g., RP(OH)(O)—O-5'-, (OH)$_2$(O)P-5'—CH$_2$—), 5'vinylphosphonate, 5'-alkyletherphosphonates (R=alkylether=methoxymethyl (MeOCH$_2$—), ethoxymethyl, etc., e.g., RP(OH)(O)—O-5'-).

The nucleic acid of the present invention may include one or more phosphorothioate modifications on one or more of the terminal ends of the first and/or the second strand. Optionally, each or either end of the first strand may comprise one or two or three phosphorothioate modified nucleotides. Optionally, each or either end of the second strand may comprise one or two or three phosphorothioate modified nucleotides. Optionally, both ends of the first strand and the 5' end of the second strand may comprise two phosphorothioate modified nucleotides. By phosphorothioate modified nucleotide it is meant that the linkage between the nucleotide and the adjacent nucleotide comprises a phosphorothioate group instead of a standard phosphate group.

Terminal modifications can also be useful for monitoring distribution, and in such cases the groups to be added may include fluorophores, e.g., fluorescein or an Alexa dye. Terminal modifications can also be useful for enhancing uptake, useful modifications for this include cholesterol. Terminal modifications can also be useful for cross-linking an RNA agent to another moiety.

Adenine, guanine, cytosine and uracil are the most common bases found in RNA. These bases can be modified or replaced to provide RNA's having improved properties. E.g., nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogues of any of the above bases and "universal bases" can be employed. Examples include 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6,N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3-carboxypropyl)uracil, 3-methylcytosine, 5-methylcytosine, N<4>-acetyl cytosine, 2-thiocytosine, N6-methyladenine, N6-isopentyladenine, 2-methylthio-N6-isopentenyladenine, N-methylguanines, or O-alkylated bases.

As used herein, the terms "non-pairing nucleotide analogue" means a nucleotide analogue which includes a non-base pairing moiety including but not limited to: 6 des amino adenosine (Nebularine), 4-Me-indole, 3-nitropyrrole, 5-nitroindole, Ds, Pa, N3-Me ribo U, N3-Me riboT, N3-Me dC, N3-Me-dT, N1-Me-dG, N1-Me-dA, N3-ethyl-dC, N3-Me dC. In some embodiments the non-base pairing nucleotide analogue is a ribonucleotide. In other embodiments it is a deoxyribonucleotide.

As used herein, the term, "terminal functional group" includes without limitation a halogen, alcohol, amine, carboxylic, ester, amide, aldehyde, ketone, ether groups.

Certain moieties may be linked to the 5' terminus of the first strand or the second strand and includes abasic ribose moiety, abasic deoxyribose moiety, modifications abasic ribose and abasic deoxyribose moieties including 2' O alkyl modifications; inverted abasic ribose and abasic deoxyribose moieties and modifications thereof, C6-imino-Pi; a mirror nucleotide including L-DNA and L-RNA; 5'OMe nucleotide; and nucleotide analogues including 4',5'-methylene nucleotide; 1-(β-D-erythrofuranosyl)nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; alpha-nucleotide; threo-pentofuranosyl nucleotide; acyclic 3',4'-seco nucleotide; 3,4-dihydroxybutyl nucleotide; 3,5-dihydroxypentyl nucleotide, 5'-5'-inverted abasic moiety; 1,4-butanediol phosphate; 5'-amino; and bridging or non bridging methylphosphonate and 5'-mercapto moieties.

The nucleic acids of the invention may be included as one or more inverted nucleotides, for example inverted thymidine or inverted adenine (for example see Takei, et al., 2002. JBC 277 (26):23800-06).

As used herein, the term "inhibit", "down-regulate", or "reduce" with respect to gene expression means the expression of the gene, or level of RNA molecules or equivalent RNA molecules encoding one or more proteins or protein subunits (e.g., mRNA), or activity of one or more proteins or protein subunits or peptides, is reduced below that observed in the absence of a nucleic acid of the invention or in reference to an siRNA molecule with no known homology to human transcripts (herein termed non-silencing control). Such control may be conjugated and modified in an analogous manner to the molecule of the invention and delivered into the target cell by the same route; for example the expression may be reduced to 90%, 80%, 70%, 60%, 50%, 40%, 30%, 20%, 15% or less than that observed in the absence of an inhibitor (which may be the nucleic acid) or in the presence of a non-silencing control (which may be a nucleic acid that is non-complementary to the target sequence).

The nucleic acid of the present invention may comprise an abasic nucleotide. The term "abasic" as used herein, refers to moieties lacking a base or having other chemical groups in place of a base at the 1' position, for example a 3',3'-linked or 5',5'-linked deoxyabasic ribose derivative.

The nucleic acid may comprise one or more nucleotides on the second and/or first strands that are modified. Alternating nucleotides may be modified, to form modified nucleotides.

Alternating as described herein means to occur one after another in a regular way. In other words, alternating means to occur in turn repeatedly. For example if one nucleotide is modified, the next contiguous nucleotide is not modified and the following contiguous nucleotide is modified and so on.

One nucleotide may be modified with a first modification, the next contiguous nucleotide may be modified with a second modification and the following contiguous nucleotide is modified with the first modification and so on, where the first and second modifications are different.

One or more of the odd numbered nucleotides of the first strand of the nucleic acid of the invention may be modified wherein the first strand is numbered 5' to 3'. The term "odd numbered" as described herein means a number not divisible by two. Examples of odd numbers are 1, 3, 5, 7, 9, 11 and so on. One or more of the even numbered nucleotides of the first strand of the nucleic acid of the invention may be modified, wherein the first strand is numbered 5' to 3'. The term "even numbered" as described herein means a number which is evenly divisible by two. Examples of even numbers are 2, 4, 6, 8, 10, 12, 14 and so on. One or more of the odd numbered nucleotides of the second strand of the nucleic acid of the invention may be modified wherein the second strand is numbered 3' to 5'. One or more of the even numbered nucleotides of the second strand of the nucleic acid of the invention may be modified, wherein the second strand is numbered 3' to 5'.

One or more nucleotides on the first and/or second strand may be modified, to form modified nucleotides. One or more of the odd numbered nucleotides of the first strand may be modified. One or more of the even numbered nucleotides of the first strand may be modified by at least a second modification, wherein the at least second modification is different from the modification on the one or more add nucleotides. At least one of the one or more modified even numbered nucleotides may be adjacent to at least one of the one or more modified odd numbered nucleotides.

A plurality of odd numbered nucleotides in the first strand may be modified in the nucleic acid of the invention. A plurality of even numbered nucleotides in the first strand may be modified by a second modification. The first strand may comprise adjacent nucleotides that are modified by a common modification. The first strand may also comprise adjacent nucleotides that are modified by a second different modification.

One or more of the odd numbered nucleotides of the second strand may be modified by a modification that is different to the modification of the odd numbered nucleotides on the first strand and/or one or more of the even numbered nucleotides of the second strand may be by the same modification of the odd numbered nucleotides of the first strand. At least one of the one or more modified even numbered nucleotides of the second strand may be adjacent to the one or more modified odd numbered nucleotides. A plurality of odd numbered nucleotides of the second strand may be modified by a common modification and/or a plurality of even numbered nucleotides may be modified by the same modification that is present on the first stand odd numbered nucleotides. A plurality of odd numbered nucleotides on the second strand may be modified by a second modification, wherein the second modification is different from the modification of the first strand odd numbered nucleotides.

The second strand may comprise adjacent nucleotides that are modified by a common modification, which may be a second modification that is different from the modification of the odd numbered nucleotides of the first strand.

In the nucleic acid of the invention, each of the odd numbered nucleotides in the first strand and each of the even numbered nucleotides in the second strand may be modified with a common modification and, each of the even numbered nucleotides may be modified in the first strand with a second modification and each of the odd numbered nucleotides may be modified in the second strand with the second modification.

The nucleic acid of the invention may have the modified nucleotides of the first strand shifted by at least one nucleotide relative to the unmodified or differently modified nucleotides of the second strand.

One or more or each of the odd numbered nucleotides may be modified in the first strand and one or more or each of the even numbered nucleotides may be modified in the second strand. One or more or each of the alternating nucleotides on either or both strands may be modified by a second modification. One or more or each of the even numbered nucleotides may be modified in the first strand and one or more or each of the even numbered nucleotides may be modified in the second strand. One or more or each of the alternating nucleotides on either or both strands may be modified by a second modification. One or more or each of the odd numbered nucleotides may be modified in the first strand and one or more of the odd numbered nucleotides may be modified in the second strand by a common modification. One or more or each of the alternating nucleotides on either or both strands may be modified by a second modification. One or more or each of the even numbered nucleotides may be modified in the first strand and one or more or each of the odd numbered nucleotides may be modified in the second strand by a common modification. One or more or each of the alternating nucleotides on either or both strands may be modified by a second modification.

The nucleic acid of the invention may comprise single or double stranded constructs that comprise at least two regions of alternating modifications in one or both of the strands. These alternating regions can comprise up to about 12 nucleotides but preferably comprise from about 3 to about 10 nucleotides. The regions of alternating nucleotides may be located at the termini of one or both strands of the nucleic acid of the invention. The nucleic acid may comprise from 4 to about 10 nucleotides of alternating nucleotides at each termini (3' and 5') and these regions may be separated by from about 5 to about 12 contiguous unmodified or differently or commonly modified nucleotides.

The odd numbered nucleotides of the first strand may be modified and the even numbered nucleotides may be modified with a second modification. The second strand may comprise adjacent nucleotides that are modified with a common modification, which may be the same as the modification of the odd numbered nucleotides of the first strand. One or more nucleotides of second strand may also be modified with the second modification. One or more nucleotides with the second modification may be adjacent to each other and to nucleotides having a modification that is the same as the modification of the odd numbered nucleotides of the first strand. The first strand may also comprise phosphorothioate linkages between the two nucleotides at the 3' end and at the 5' end. The second strand may comprise a phosphorothioate linkage between the two nucleotides at 5' end. The second strand may also be conjugated to a ligand at the 5' end.

The nucleic acid of the invention may comprise a first strand comprising adjacent nucleotides that are modified with a common modification. One or more of such nucleotides may be adjacent to one or more nucleotides which may be modified with a second modification. One or more nucleotides with the second modification may be adjacent. The second strand may comprise adjacent nucleotides that are modified with a common modification, which may be the same as one of the modifications of one or more nucleotides of the first strand. One or more nucleotides of second strand may also be modified with the second modification. One or more nucleotides with the second modification may be adjacent. The first strand may also comprise phosphorothioate linkages between the two nucleotides at the 5' end and at the 3' end. The second strand may comprise a phosphorothioate linkage between the two nucleotides at 3' end. The second strand may also be conjugated to a ligand at the 5' end.

The nucleotides numbered (from 5' to 3' on the first strand and 3' and 5' on the second strand) 1, 3, 5, 7, 9, 11, 13, 15, 17, 19, 21, 23 and 25 may be modified by a modification on the first strand. The nucleotides numbered 2, 4, 6, 8, 10, 12, 14, 16, 18, 20, 22 and 24 may be modified by a second modification on the first strand. The nucleotides numbered 1, 3, 5, 7, 9, 11, 13, 15, 17, 19, 21, 23 may be modified by a modification on the second strand. The nucleotides numbered 2, 4, 6, 8, 10, 12, 14, 16, 18, 20, 22 and 24 may be modified by a second modification on the second strand. Nucleotides are numbered for the sake of the nucleic acid of the present invention from 5' to 3' on the first strand and 3' and 5' on the second strand.

The nucleotides numbered 2, 4, 6, 8, 10, 12, 14, 16, 18, 20, 22 and 24 may be modified by a modification on the first strand. The nucleotides numbered 1, 3, 5, 7, 9, 11, 13, 15, 17, 19, 21, 23 may be modified by a second modification on the first strand. The nucleotides numbered 1, 3, 5, 7, 9, 11, 13, 15, 17, 19, 21, 23 may be modified by a modification on the second strand. The nucleotides numbered 2, 4, 6, 8, 10, 12, 14, 16, 18, 20, 22 and 24 may be modified by a second modification on the second strand.

Clearly, if the first and/or the second strand are shorter than 25 nucleotides in length, such as 19 nucleotides in length, there are no nucleotides numbered 20, 21, 22, 23, 24 and 25 to be modified. The skilled person understands the description above to apply to shorter strands, accordingly.

One or more modified nucleotides on the first strand may be paired with modified nucleotides on the second strand having a common modification. One or more modified nucleotides on the first strand may be paired with modified nucleotides on the second strand having a different modification. One or more modified nucleotides on the first strand may be paired with unmodified nucleotides on the second strand. One or more modified nucleotides on the second strand may be paired with unmodified nucleotides on the first strand. In other words, the alternating nucleotides can be aligned on the two strands such as, for example, all the modifications in the alternating regions of the second strand are paired with identical modifications in the first strand or alternatively the modifications can be offset by one nucleotide with the common modifications in the alternating regions of one strand pairing with dissimilar modifications (i.e. a second or further modification) in the other strand. Another option is to have dissimilar modifications in each of the strands.

The modifications on the first strand may be shifted by one nucleotide relative to the modified nucleotides on the second strand, such that common modified nucleotides are not paired with each other.

The modification and/or modifications may each and individually be selected from the group consisting of 3-terminal deoxy-thymine, 2'-O-methyl, a 2'-deoxy-modification, a 2'-amino-modification, a 2'-alkyl-modification, a morpholino modification, a phosphoramidate modification, 5'-phosphorothioate group modification, a 5' phosphate or 5' phosphate mimic modification and a cholesteryl derivative or a dodecanoic acid bisdecylamide group modification and/or the modified nucleotide may be any one of a locked nucleotide, an abasic nucleotide or a non-natural base comprising nucleotide.

At least one modification may be 2'-O-methyl and/or at least one modification may be 2'-F. Further modifications as described herein may be present on the first and/or second strand.

Throughout the description of the invention, "same or common modification" means the same modification to any nucleotide, be that A, G, C or U modified with a group such as such as a methyl group or a fluoro group. Is it not taken to mean the same addition on the same nucleotide. For example, 2'F-dU, 2'F-dA, 2'F-dC, 2'F-dG are all considered to be the same or common modification, as are 2'-OMe-rU, 2'-OMe-rA; 2'-OMe-rC; 2'-OMe-rG. A 2'F modification is a different modification to a 2'OMe modification.

Some representative modified nucleic acid sequences of the present invention are shown in the examples. These examples are meant to be representative and not limiting.

Preferably, the nucleic acid may comprise a modification and the second or further modification which are each and individually selected from the group comprising 2'-O-methyl modification and 2'-F modification. The nucleic acid may comprise a modification that is 2'-O-methyl (2'OMe) that may be a first modification, and a second modification that is 2'-F. The nucleic acid of the invention may also include a phosphorothioate modification and/or a deoxy modification which may be present in or between the terminal 1, 2 or 3 nucleotides of each or any end of each or both strands.

The nucleic acid of the invention may be conjugated to a ligand, to form a conjugate.

Some ligands can have endosomolytic properties. The endosomolytic ligands promote the lysis of the endosome and/or transport of the composition of the invention, or its components, from the endosome to the cytoplasm of the cell. The endosomolytic ligand may be a polyanionic peptide or peptidomimetic which shows pH-dependent membrane activity and fusogenicity. The endosomolytic component may contain a chemical group which undergoes a change in charge or protonation in response to a change in pH. The endosomolytic component may be linear or branched.

Ligands can include therapeutic modifiers, e.g., for enhancing uptake; diagnostic compounds or reporter groups e.g., for monitoring distribution; cross-linking agents; and nuclease-resistance conferring moieties. General examples include lipids, steroids, vitamins, sugars, proteins, peptides, polyamines, and peptide mimics. Ligands can include a naturally occurring substance, such as a protein, carbohydrate, or lipid. The ligand may be a recombinant or synthetic molecule.

Ligands can also include targeting groups, e.g. a cell or tissue targeting agent. The targeting ligand may be a lectin, glycoprotein, lipid or protein.

Other examples of ligands include dyes, intercalating agents, cross-linkers, porphyrins, polycyclic aromatic hydrocarbons, artificial endonucleases or a chelator, lipophilic molecules, alkylating agents, phosphate, amino, mercapto, PEG, MPEG, alkyl, substituted alkyl, radiolabelled markers, enzymes, haptens, transport/absorption facilitators, synthetic ribonucleases, or imidazole clusters.

Ligands can be proteins, e.g. glycoproteins or peptides. Ligands may also be hormones or hormone receptors. They may also include non-peptidic species, such as lipids, lectins, carbohydrates, vitamins, or cofactors.

The ligand may be a substance such as a drug which can increase the uptake of the nucleic acid into a cell, for example, by disrupting the cell's cytoskeleton.

The ligand may increase uptake of the nucleic acid into the cell by activating an inflammatory response. Such ligands include tumour necrosis factor alpha (TNF-alpha), interleukin-1 beta, or gamma interferon.

The ligand may be a lipid or lipid-based molecule. The lipid or lipid-based molecule preferably binds a serum protein. Preferably, the lipid-based ligand binds human serum albumin (HSA). A lipid or lipid-based molecule can increase resistance to degradation of the conjugate, increase targeting or transport into target cell, and/or can adjust binding to a serum protein. A lipid-based ligand can be used to modulate binding of the conjugate to a target tissue.

The ligand may be a steroid. Preferably, the ligand is cholesterol or a cholesterol derivative.

The ligand may be a moiety e.g. a vitamin, which is taken up by a target cell. Exemplary vitamins include vitamin A, E, K, and the B vitamins. Vitamins may be taken up by a proliferating cell, which may be useful for delivering the nucleic acid to cells such as malignant or non-malignant tumour cells.

The ligand may be a cell-permeation agent, such as a helical cell-permeation agent. Preferably such an agent is amphipathic.

The ligand may be a peptide or peptidomimetic. A peptidomimetic is a molecule capable of folding into a defined three-dimensional structure similar to a natural peptide. The peptide or peptidomimetic ligand may include naturally occurring or modified peptides, or both. A peptide or peptidomimetic can be a cell permeation peptide, cationic peptide, amphipathic peptide, or hydrophobic peptide. The peptide moiety can be a dendrimer peptide, constrained peptide, or crosslinked peptide. The peptide moiety can include a hydrophobic membrane translocation sequence. The peptide moiety can be a peptide capable of carrying large polar molecules such as peptides, oligonucleotides, and proteins across cell membranes, e.g. sequences from the HIV Tat protein (GRKKRRQRRRPPQ(SEQ ID NO: 204)) and the *Drosophila* Antennapedia protein (RQIKIWFQNRRMKWKK(SEQ ID NO: 205)). Preferably the peptide or peptidomimetic is a cell targeting peptide, e.g. arginine-glycine-aspartic acid (RGD)-peptide.

The ligand may be a cell permeation peptide that is capable of permeating, for example, a microbial cell or a mammalian cell.

The ligand may be a pharmacokinetic modulator. The pharmacokinetic modulator may be lipophiles, bile acids, steroids, phospholipid analogues, peptides, protein binding agents, PEG, vitamins, etc.

When two or more ligands are present, the ligands can all have the same properties, all have different properties, or some ligands have the same properties while others have different properties. For example, a ligand can have targeting properties, have endosomolytic activity or have PK modulating properties. In a preferred embodiment, all the ligands have different properties.

Ligands can be coupled to the nucleic acid at the 3'-end, 5'-end, and/or at an internal position. Preferably the ligand is coupled to the nucleic acid via an intervening tether or linker.

In some embodiments the nucleic acid is a double-stranded nucleic acid. In a double-stranded nucleic acid the ligand may be attached to one or both strands. In some embodiments, a double-stranded nucleic acid contains a ligand conjugated to the sense strand. In other embodiments, a double-stranded nucleic acid contains a ligand conjugated to the antisense strand.

Ligands can be conjugated to nucleobases, sugar moieties, or internucleosidic linkages of nucleic acid molecules. Conjugation to purine nucleobases or derivatives thereof can occur at any position including endocyclic and exocyclic atoms. Conjugation to pyrimidine nucleotides or derivatives thereof can also occur at any position. Conjugation to sugar moieties of nucleosides can occur at any carbon atom. Conjugation to internucleosidic linkages may occur at the phosphorus atom of a phosphorus-containing linkage or at an oxygen, nitrogen, or sulphur atom bonded to the phosphorus atom. For amine- or amide-containing internucleosidic linkages, conjugation may occur at the nitrogen atom of the amine or amide or to an adjacent carbon atom.

The ligand is typically a carbohydrate, e.g. a monosaccharide, disaccharide, trisaccharide, tetrasaccharide or polysaccharide. The ligand may be conjugated to the nucleic acid by a linker. The linker may be a monovalent, bivalent, or trivalent branched linker.

Means for efficient delivery of oligonucleotides, in particular double stranded nucleic acids of the invention, to cells in vivo is important and requires specific targeting and substantial protection from the extracellular environment, particularly serum proteins. One method of achieving specific targeting is to conjugate a targeting moiety or ligand to the nucleic acid. The targeting moiety helps in targeting the nucleic acid to the required target site and there is a need to conjugate appropriate targeting moieties for the desired receptor sites for the conjugated molecules to be taken up by the cells such as by endocytosis. The targeting moiety or ligand can be any moiety or ligand that is capable of targeting a specific receptor.

For example, the Asialoglycoprotein receptor (ASGP-R) is a high capacity receptor, which is highly abundant on hepatocytes. One of the first disclosures of triantennary cluster glycosides was in U.S. Pat. No. 5,885,968. Conjugates having three GalNAc ligands and comprising phosphate groups are known and are described in Dubber et al. (2003). The ASGP-R shows a 50-fold higher affinity for N-Acetyl-D-Galactosylamine (GalNAc) than D-Gal.

Hepatocytes expressing the lectin (asialoglycoprotein receptor; ASGPR), which recognizes specifically terminal β-galactosyl subunits of glycosylated proteins or other oligosaccharides (P. H. Weigel et. al., 2002) can be used for targeting a drug to the liver by covalent coupling of galactose or galactoseamine to the drug substance (S. Ishibashi, et. al. 1994). Furthermore the binding affinity can be significantly increased by the multi-valency effect, which is achieved by the repetition of the targeting unit (E. A. L. Biessen et. al., 1995).

The ASGPR is a mediator for an active endosomal transport of terminal β-galactosyl containing glycoproteins, thus ASGPR is highly suitable for targeted delivery of drug candidates like nucleic acid, which have to be delivered into a cell (Akinc et al.).

The saccharide, which can also be referred to as the ligand, may be selected to have an affinity for at least one type of receptor on a target cell. In particular, the receptor is on the surface of a mammalian liver cell, for example, the hepatic asialoglycoprotein receptor (ASGP-R).

The saccharide may be selected from N-acetyl galactoseamine, mannose, galactose, glucose, glucosamone and fucose. The saccharide may be N-acetyl galactoseamine (GalNAc).

A ligand for use in the present invention may therefore comprise (i) one or more N-acetyl galactosamine (GalNac) moieties and derivatives thereof, and (ii) a linker, wherein the linker conjugates the GalNac moieties to a sequence as defined in any preceding aspects. The linker may be a bivalent or trivalent or tetravalent branched structure. The nucleotides may be modified as defined herein.

"GalNAc" refers to 2-(Acetylamino)-2-deoxy-D-galactopyranose, commonly referred to in the literature as N-acetyl galactosamine. Reference to "GalNAc" or "N-acetyl galactoseamine" includes both the β-form: 2-(Acetylamino)-2-deoxy-β-D-galactopyranose and the α-form: 2-(Acetylamino)-2-deoxy-α-D-galactopyranose. Both the β-form: 2-(Acetylarnino)-2-deoxy-β-D-galactopyranose and α-form: 2-(Acetylamino)-2-deoxy-α-D-galactopyranose may be used interchangeably. Preferably, the compounds of the invention comprise the β-form, 2-(Acetylarnino)-2-deoxy-β-D-galactopyranose.

The ligand may comprise GalNAc.

The ligand may comprise a compound of formula I:

$$[S-X^1-P-X^2]_3-A-X^3- \quad (I)$$

wherein:
S represents a saccharide, wherein the saccharide is N-acetyl galactosamine;
$X^1$ represents $C_3$-$C_6$ alkylene or $(-CH_2-CH_2-O)_m(-CH_2)_2-$ wherein m is 1, 2, or 3;
P is a phosphate or modified phosphate (preferably a thiophosphate);
$X^2$ is alkylene or an alkylene ether of the formula $(-CH_2)_n-O-CH_2-$ where n=1-6;
A is a branching unit;
$X^3$ represents a bridging unit;
wherein a nucleic acid according to the present invention is conjugated to $X^3$ via a phosphate or modified phosphate (preferably a thiophosphate).

In formula I, branching unit "A" branches into three in order to accommodate the three saccharide ligands. The branching unit is covalently attached to the ligands and the nucleic acid. The branching unit may comprise a branched aliphatic group comprising groups selected from alkyl, amide, disulphide, polyethylene glycol, ether, thioether and hydroxyamino groups. The branching unit may comprise groups selected from alkyl and ether groups.

The branching unit A may have a structure selected from:

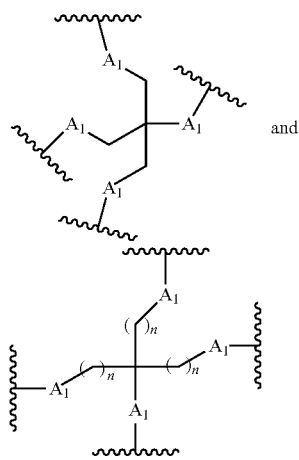

and wherein each $A_1$ independently represents O, S, C=O or NH; and
each n independently represents an integer from 1 to 20.

The branching unit may have a structure selected from:

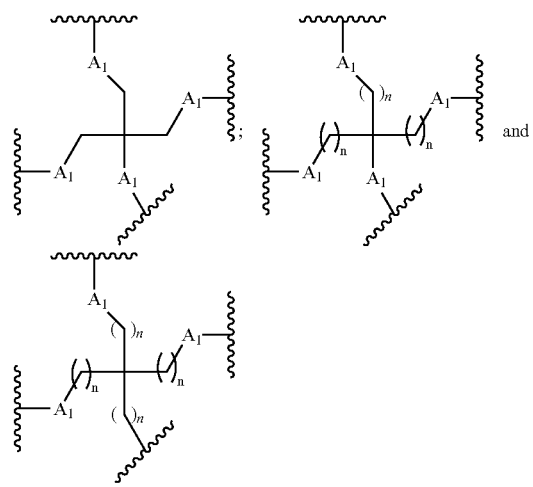

wherein each $A_1$ independently represents O, S, C=O or NH; and
each n independently represents an integer from 1 to 20.

The branching unit may have a structure selected from:

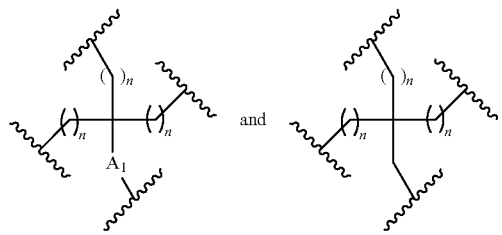

wherein $A_1$ is O, S, C=O or NH; and
each n independently represents an integer from 1 to 20.

The branching unit may have the structure:

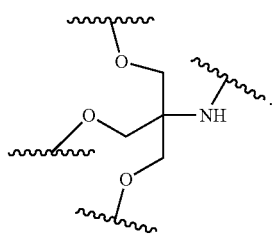 [SMILES: *NC(CO*)(CO*)CO*]

The branching unit may have the structure:

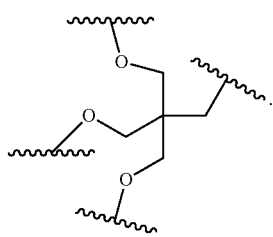 [SMILES: *CC(CO*)(CO*)CO*]

The branching unit may have the structure:

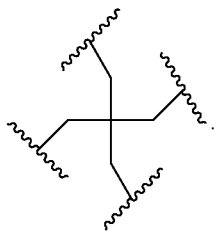 [SMILES: *CC(C*)(C*)C*]

Optionally, the branching unit consists of only a carbon atom.

$X^3$ may be selected from —$C_1$-$C_{20}$ alkylene-, —$C_2$-$C_{20}$ alkenylene-, an alkylene ether of formula —($C_1$-$C_{20}$ alkylene)-O—($C_1$-$C_{20}$ alkylene)-, —C(O)—$C_1$-$C_{20}$ alkylene-, —$C_0$-$C_4$ alkylene(Cy)$C_0$-$C_4$ alkylene- wherein Cy represents a substituted or unsubstituted 5 or 6 membered cycloalkylene, arylene, heterocyclylene or heteroarylene ring, —$C_1$-$C_4$ alkylene-NHC(O)—$C_1$-$C_4$ alkylene-, —$C_1$-$C_4$ alkylene-C(O)NH—$C_1$-$C_4$ alkylene-, —$C_1$-$C_4$ alkylene-SC(O)—$C_1$-$C_4$ alkylene-, —$C_1$-$C_4$ alkylene-C(O)S—$C_1$-$C_4$ alkylene-, —$C_1$-$C_4$ alkylene-OC(O)—$C_1$-$C_4$ alkylene-, —$C_1$-$C_4$ alkylene-C(O)O—$C_1$-$C_4$ alkylene-, and —$C_1$-$C_6$ alkylene-S—S—$C_1$-$C_6$ alkylene-.

$X^3$ may be an alkylene ether of formula —($C_1$-$C_{20}$ alkylene)-O—($C_1$-$C_{20}$ alkylene)-. $X^3$ may be an alkylene ether of formula —($C_1$-$C_{20}$ alkylene)-O—($C_4$-$C_{20}$ alkylene)-, wherein said ($C_4$-$C_{20}$ alkylene) is linked to Z. $X^3$ may be selected from the group consisting of —$CH_2$—O—$C_3H_6$—, —$CH_2$—O—$C_4H_8$—, —$CH_2$—O—$C_6H_{12}$— and —$CH_2$—O—$C_8H_{16}$—, especially —$CH_2$—O—$C_4H_8$—, —$CH_2$—O—$C_6H_{12}$— and —$CH_2$—O—$C_8H_{16}$—, wherein in each case the —$CH_2$— group is linked to A.

The ligand may comprise a compound of formula (II):

wherein:

S represents a saccharide;

$X^1$ represents $C_3$-$C_6$ alkylene or an ethylene glycol stem (—$CH_2$—$CH_2$—O)$_m$(—$CH_2$)$_2$— wherein m is 1, 2, or 3;

P is a phosphate or modified phosphate (preferably a thiophosphate);

$X^2$ is $C_1$-$C_8$ alkylene;

A is a branching unit selected from:

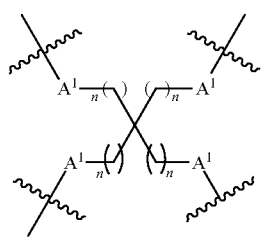

$A^1$ = O, NH
n = 1 to 4

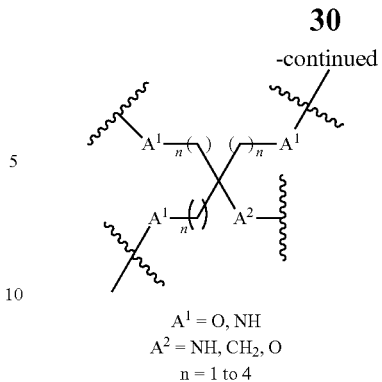

$A^1$ = O, NH
$A^2$ = NH, $CH_2$, O
n = 1 to 4

$X^3$ is a bridging unit;

wherein a nucleic acid according to the present invention is conjugated to $X^3$ via a phosphate or modified phosphate (preferably a thiophosphate)

Branching unit A may have the structure:

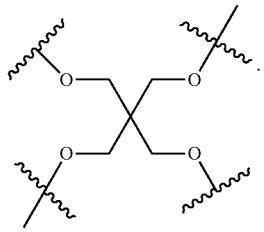 [SMILES: *OCC(CO*)(CO*)CO*]

Branching unit A may have the structure:

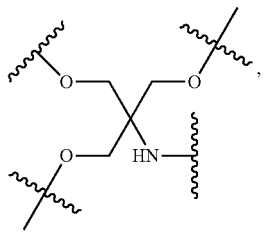

wherein $X^3$ is attached to the nitrogen atom.

$X^3$ may be $C_1$-$C_{20}$ alkylene. Preferably, $X^3$ is selected from the group consisting of —$C_3H_6$—, —$C_4H_8$—, —$C_6H_{12}$— and —$C_8H_{16}$—, especially —$C_4H_8$—, —$C_6H_{12}$— and —$C_8H_{16}$—.

The ligand may comprise a compound of formula (III):

wherein:

S represents a saccharide;

$X^1$ represents $C_3$-$C_6$ alkylene or an ethylene glycol stem (—$CH_2$—$CH_2$—O)$_m$(—$CH_2$)$_2$— wherein m is 1, 2, or 3;

P is a phosphate or modified phosphate (preferably a thiophosphate);

$X^2$ is an alkylene ether of formula —$C_3H_6$—O—$CH_2$—;

A is a branching unit;

$X^3$ is an alkylene ether of formula selected from the group consisting of —$CH_2$—O—$CH_2$—, —$CH_2$—O—$C_2H_4$—, —$CH_2$—O—$C_3H_6$—, —$CH_2$—O—$C_4H_8$—, —$CH_2$—O—$C_5H_{10}$—, —$CH_2$—O—$C_6H_{12}$—, —$CH_2$—O—$C_7H_{14}$—, and —$CH_2$—O—$C_8H_{16}$—, wherein in each case the —CH$_2$— group is linked to A, wherein a nucleic acid according to the present invention is conjugated to X$^3$ via a phosphate or modified phosphate (preferably a thiophosphate)

The branching unit may comprise carbon. Preferably, the branching unit is carbon.

X$^3$ may be selected from the group consisting of —CH$_2$—O—C$_4$H$_8$—, —CH$_2$—O—C$_5$H$_{10}$—, —CH$_2$—O—C$_6$H$_{12}$—, —CH$_2$—O—C$_7$H$_{14}$—, and —CH$_2$—O—C$_8$H$_{16}$—. Preferably, X$^3$ is selected from the group consisting of —CH$_2$—O—C$_4$H$_8$—, —CH$_2$—O—C$_6$H$_{12}$— and —CH$_2$—O—C$_8$H$_{16}$.

For any of the above aspects, P represents a modified phosphate group. P can be represented by:

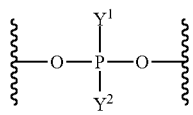

wherein Y$^1$ and Y$^2$ each independently represent =O, =S, —O$^-$, —OH, —SH, —BH$_3$, —OCH$_2$CO$_2$, —OCH$_2$CO$_2$R$^x$, —OCH$_2$C(S)OR$^x$, and —OR$^x$, wherein R$^x$ represents C$_1$-C$_6$ alkyl and wherein

indicates attachment to the remainder of the compound.

By modified phosphate It is meant a phosphate group wherein one or more of oxygens is replaced. Examples of modified phosphate groups include phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulphur. One, each or both non-linking oxygens in the phosphate group can be independently any one of S, Se, B, C, H, N, or OR (R is alkyl or aryl).

The phosphate linker can also be modified by replacement of a linking oxygen with nitrogen (bridged phosphoroamidates), sulfur (bridged phosphorothioates) and carbon (bridged methylenephosphonates). The replacement can occur at a terminal oxygen. Replacement of the non-linking oxygens with nitrogen is possible.

For example, Y$^1$ may represent —OH and Y$^2$ may represent =O or =S; or
Y$^1$ may represent —O$^-$ and Y$^2$ may represent =O or =S;
Y$^1$ may represent =O and Y$^2$ may represent —CH$_3$, —SH, —OR$^x$, or —BH$_3$
Y$^1$ may represent =S and Y$^2$ may represent —CH$_3$, OR$^x$ or —SH.

It will be understood by the skilled person that in certain instances there will be delocalisation between Y$^1$ and Y$^2$.

Preferably, the modified phosphate group is a thiophosphate group. Thiophosphate groups include bithiophosphate (i.e. where Y$^1$ represents =S and Y$^2$ represents —S$^-$) and monothiophosphate (i.e. where Y$^1$ represents —O$^-$ and Y$^2$ represents =S, or where Y$^1$ represents =O and Y$^2$ represents —S$^-$). Preferably, P is a monothiophosphate. The inventors have found that conjugates having thiophosphate groups in replacement of phosphate groups have improved potency and duration of action in vivo.

P may also be an ethylphosphate (i.e. where Y$^1$ represents =O and Y$^2$ represents OCH$_2$CH$_3$).

The saccharide, which can also be referred to as the ligand, may be selected to have an affinity for at least one type of receptor on a target cell. In particular, the receptor is on the surface of a mammalian liver cell, for example, the hepatic asialoglycoprotein receptor (ASGP-R).

For any of the above aspects, the saccharide may be selected from N-acetyl with one or more of galactosamine, mannose, galactose, glucose, glucosamine and fructose. Preferably, the saccharide is two molecules of N-acetyl galactosamine (GalNAc). The compounds of the invention may have 3 ligands which are each preferably N-acetyl galactosamine.

"GalNAc" refers to 2-(Acetylamino)-2-deoxy-D-galactopyranose, commonly referred to in the literature as N-acetyl galactosamine. Reference to "GalNAc" or "N-acetyl galactosamine" includes both the β-form: 2-(Acetylamino)-2-deoxy-β-D-galactopyranose and the α-form: 2-(Acetylamino)-2-deoxy-α-D-galactopyranose. In certain embodiments, both the β-form: 2-(Acetylarnino)-2-deoxy-β-D-galactopyranose and α-form: 2-(Acetylamino)-2-deoxy-α-D-galactopyranose may be used interchangeably. Preferably, the compounds of the invention comprise the β-form, 2-(Acetylarnino)-2-deoxy-β-D-galactopyranose.

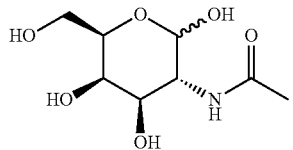

2-(Acetylamino)-2-deoxy-D-galactopyranose

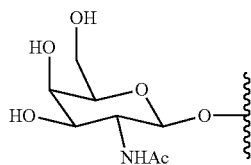 [SMILES: *OC1OC(CO)C(O)C(O)C1NC(C)=O]

2-(Acetylamino)-2-deoxy-β-D-galactopyranose

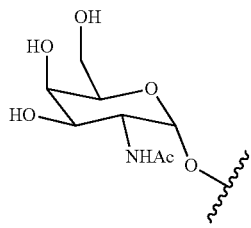 [SMILES: *OC1OC(CO)C(O)C(O)C1NC(C)=O]

2-(Acetylamino)-2-deoxy-α-D-galactopyranose

For any of the above compounds of formula (III), X$^1$ may be an ethylene glycol stem (—CH$_2$—CH$_2$—O)$_m$(—CH$_2$)$_2$— wherein m is 1, 2, or 3. $X^1$ may be (—CH$_2$—CH$_2$—O)(—CH$_2$)$_2$—. $X^1$ may be (—CH$_2$—CH$_2$—O)$_2$(—CH$_2$)$_2$—. $X^1$ may be (—CH$_2$—CH$_2$—O)$_3$(—CH$_2$)$_2$—. Preferably, $X^1$ is (—CH$_2$—CH$_2$—O)$_2$(—CH$_2$)$_2$—. Alternatively, $X^1$ represents $C_3$-$C_6$ alkylene. $X^1$ may be propylene. $X^1$ may be butylene. $X^1$ may be pentylene. $X^1$ may be hexylene. Preferably the alkyl is a linear alkylene. In particular, $X^1$ may be butylene.

For compounds of formula (III), $X^2$ represents an alkylene ether of formula —C$_3$H$_6$—O—CH$_2$— i.e. C$_3$ alkoxy methylene, or —CH$_2$CH$_2$CH$_2$OCH$_2$—.

The present invention therefore additionally provides a conjugated nucleic acid having one of the following structures:

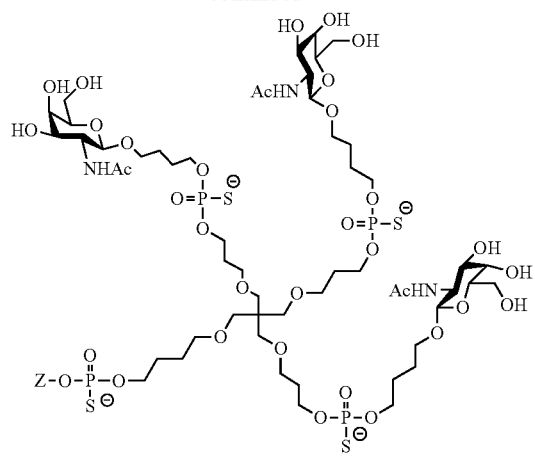

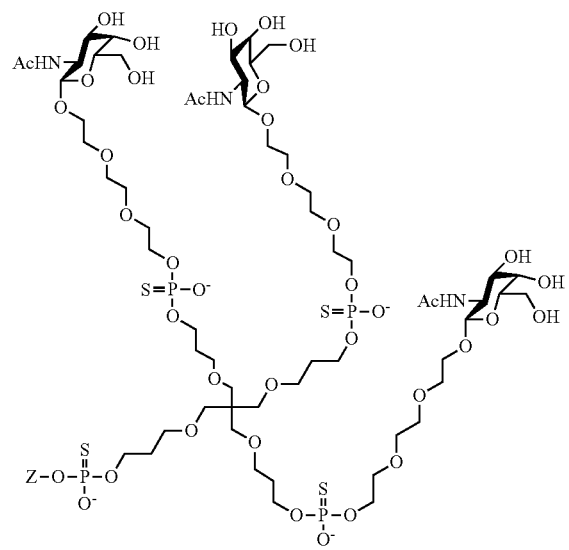

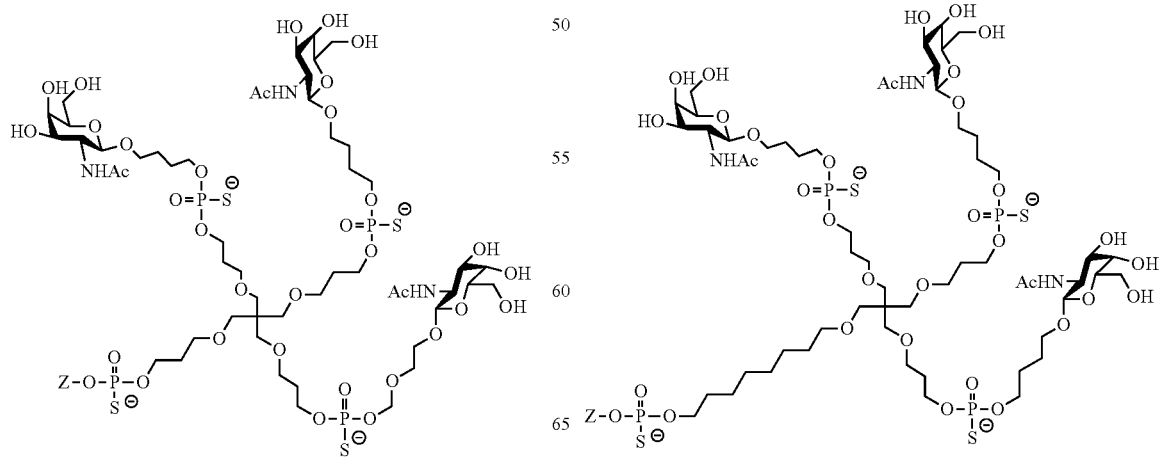

-continued

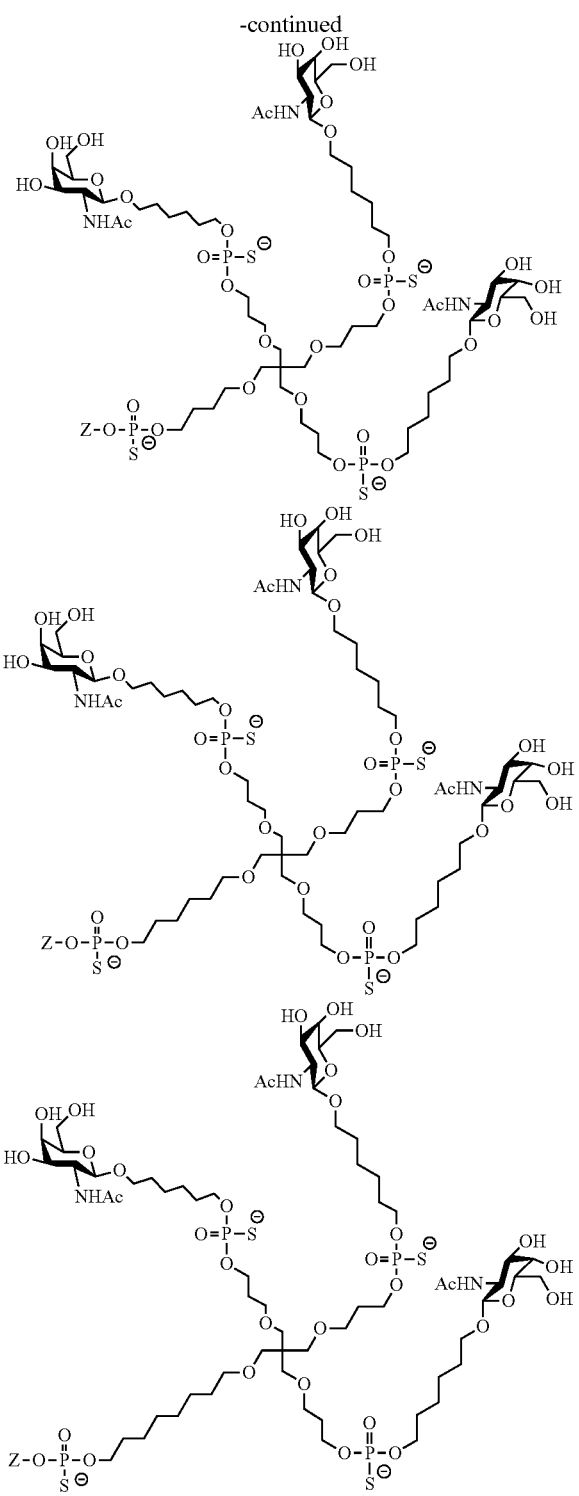

wherein Z represents a nucleic acid as defined herein before.

The invention provides as a further aspect, a nucleic acid for inhibiting expression of a target gene in a cell, comprising at least one duplex region that comprises at least a portion of a first strand and at least a portion of a second strand that is at least partially complementary to the first strand, wherein said first strand is at least partially complementary to at least a portion of a RNA transcribed from said target gene to be inhibited and wherein the terminal nucleotide at the 3' end of at least one of the first strand and the second strand is an inverted nucleotide and is attached to the adjacent nucleotide via the 3' carbon of the terminal nucleotide and the 3' carbon of the adjacent nucleotide and/or the terminal nucleotide at the 5' end of at least one of the first strand and the second strand is an inverted nucleotide and is attached to the adjacent nucleotide via the 5' carbon of the terminal nucleotide and the 5' carbon of the adjacent nucleotide, and wherein the nucleic acid molecule is conjugated to a ligand.

The nucleic acid may be conjugated to a ligand as herein described. The nucleotides of the first and/or second strand may be modified, as herein described.

The ligand may comprise GalNac and may be of the structure set out in 8.

A cleavable linking group is a linker which is stable outside the cell but is cleaved upon entry into a target cell. Cleavage releases the two parts the linker is holding together.

In a preferred embodiment, the nucleic acid of the invention comprises a cleavable linking group that is cleaved at least 10 times or more, preferably at least 100-fold faster in a target cell or under a first reference condition (which can, for example, be selected to mimic or represent intracellular conditions) than in the blood of a subject, or under a second reference condition (which can, for example, be selected to mimic or represent conditions found in the blood or serum).

Cleavable linking groups are susceptible to cleavage agents, e.g. pH, redox potential, or the presence of degradative molecules. Degradative molecules include oxidative or reductive enzymes, reductive agents (such as mercaptans), esterases, endosomes or agents than can create an acidic environment, enzymes that can hydrolyze or degrade an acid cleavable linking group by acting as a general acid, peptidases, and phosphatases.

A cleavable linking group may be a disulphide bond, which is susceptible to pH.

A linker may include a cleavable linking group that is cleavable by a particular enzyme. The type of cleavable linking group incorporated into a linker can depend on the target cell. For example, a linker that includes an ester group is preferred when a liver cell is the target. Linkers that contain peptide bonds can be used when targeting cells rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. In preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

In one aspect, the cleavable linking group may be a redox cleavable linking group. The redox cleavable linking group may be a disulphide linking group.

In one aspect, the linking group may be a phosphate-based cleavable linking group. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—. A preferred embodiment is —O—P(O)(OH)—O—.

In one aspect, the cleavable linking group may be an acid cleavable linking group. Preferably the acid cleavable linking group are cleaved in environments where the pH is 6.5 or lower, or are cleaved by agents such as enzymes that can act as a general acid. Examples of acid cleavable linking groups include but are not limited to hydrazones, esters, and esters of amino acids. Acid cleavable groups can have the general formula —C=NN—; C(O)O, or —OC(O). A preferred embodiment is a linking group where the carbon attached to the oxygen of the ester (the alkoxy group) is an aryl group, substituted alkyl group, or tertiary alkyl group such as dimethyl pentyl or t-butyl.

In one embodiment, the cleavable linking group may be an ester-based cleavable linking group. Examples of ester-based cleavable linking groups include but are not limited to esters of alkylene, alkenylene and alkynylene groups.

In one embodiment, the cleavable linking group may be a peptide-based cleavable linking group. Peptide-based cleavable linking groups are peptide bonds formed between amino acids to yield oligopeptides (e.g., dipeptides, tripeptides etc.) and polypeptides. The peptide based cleavage group is generally limited to the peptide bond (i.e., the amide bond) formed between amino acids yielding peptides and proteins and does not include the entire amide functional group. Peptide-based cleavable linking groups have the general formula —NHCHR$^A$C(O)NHCHR$^B$C(O)—, where RA and RB are the R groups of the two adjacent amino acids.

The nucleic acid as described herein may be formulated with a lipid in the form of a liposome. Such a formulation may be described in the art as a lipoplex. The composition with a lipid/liposome may be used to assist with delivery of the nucleic acid of the invention to the target cells. The lipid delivery system herein described may be used as an alternative to a conjugated ligand. The modifications herein described may be present when using the nucleic acid of the invention with a lipid delivery system or with a ligand conjugate delivery system.

Such a lipoplex may comprise a lipid composition comprising:
i) a cationic lipid, or a pharmaceutically acceptable salt thereof;
ii) a steroid;
iii) a phosphatidylethanolamine phospholipid;
iv) a PEGylated lipid.

The cationic lipid may be an amino cationic lipid.

The cationic lipid may have the formula (I):

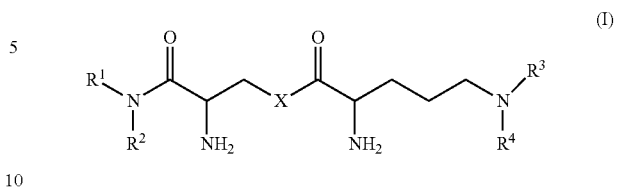

or a pharmaceutically acceptable salt thereof, wherein:

X represents O, S or NH;

$R^1$ and $R^2$ each independently represents a $C_4$-$C_{22}$ linear or branched alkyl chain or a $C_4$-$C_{22}$ linear or branched alkenyl chain with one or more double bonds, wherein the alkyl or alkenyl chain optionally contains an intervening ester, amide or disulfide;

when X represents S or NH, $R^3$ and $R^4$ each independently represent hydrogen, methyl, ethyl, a mono- or polyamine moiety, or $R^3$ and $R^4$ together form a heterocyclyl ring;

when X represents O, $R^3$ and $R^4$ each independently represent hydrogen, methyl, ethyl, a mono- or polyamine moiety, or $R^3$ and $R^4$ together form a heterocyclyl ring, or $R^3$ represents hydrogen and $R^4$ represents C(NH)(NH$_2$).

The cationic lipid may have the formula (IA):

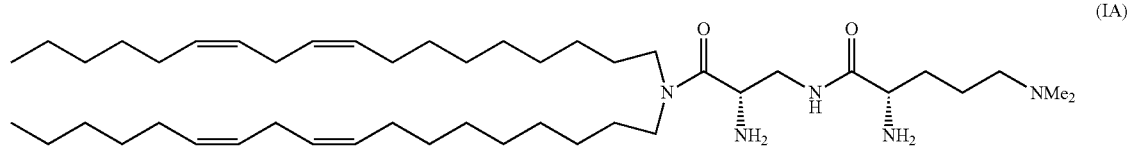 [SMILES: CCCCC/C=C\C/C=C\CCCCCCCCN(CCCCCCCC/C=C\C/C=C\CCCCC)C(=O)[C@@H](N)CNC(=O)[C@@H](N)CCCN(C)C]

or a pharmaceutically acceptable salt thereof.

The cationic lipid may have the formula (IB):

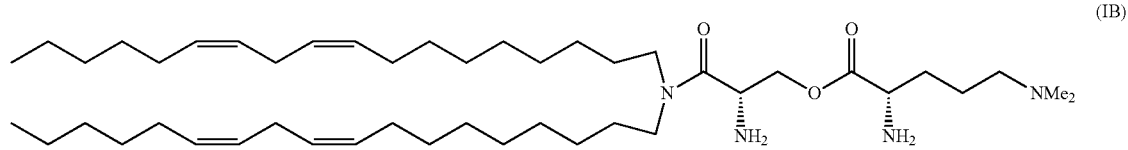 [SMILES: CCCCC/C=C\C/C=C\CCCCCCCCN(CCCCCCCC/C=C\C/C=C\CCCCC)C(=O)[C@@H](N)COC(=O)[C@@H](N)CCCN(C)C]

or a pharmaceutically acceptable salt thereof.

The content of the cationic lipid component may be from about 55 mol % to about 65 mol % of the overall lipid content of the formulation. In particular, the cationic lipid component is about 59 mol % of the overall lipid content of the formulation.

The formulations further comprise a steroid. the steroid may be cholesterol. The content of the steroid may be from about 26 mol % to about 35 mol % of the overall lipid content of the lipid formulation. More particularly, the content of steroid may be about 30 mol % of the overall lipid content of the lipid formulation.

The phosphatidylethanolamine phospholipid may be selected from group consisting of 1,2-diphytanoyl-sn-glycero-3-phosphoethanolamine (DPhyPE), 1,2-dioleoyl-sn-glycero-3-phosphoethanolamine (DOPE), 1,2-distearoyl-sn-glycero-3-phosphoethanolamine (DSPE), 1,2-Dilauroyl-sn-glycero-3-phosphoethanolamine (DLPE), 1,2-Dimyristoylsn-glycero-3-phosphoethanolamine (DMPE), 1,2-Dipalmitoyl-sn-glycero-3-phosphoethanolamine (DPPE), 1,2-Dilinoleoyl-sn-glycero-3-phosphoethanolamine (DLoPE), 1-Palmitoyl-2-oleoyl-sn-glycero-3-phosphoethanolamine (POPE), 1,2-Dierucoyl-sn-glycero-3-phosphoethanolamine (DEPE), 1,2-Disqualeoyl-sn-glycero-3-phosphoethanolamine (DSQPE) and 1-Stearoyl-2-linoleoyl-sn-glycero-3-phosphoethanolamine (SLPE). The content of the phospholipid may be about 10 mol % of the overall lipid content of the composition.

The PEGylated lipid may be selected from the group consisting of 1,2-dimyristoyl-sn-glycerol, methoxypolyethylene glycol (DMG-PEG) and C16-Ceramide-PEG. The content of the PEGylated lipid may be about 1 to 5 mol % of the overall lipid content of the formulation.

The content of the cationic lipid component in the composition may be from about 55 mol % to about 65 mol % of the overall lipid content of the lipid formulation, preferably about 59 mol % of the overall lipid content of the lipid formulation.

The composition may have a molar ratio of the components of i): ii): iii): iv) selected from 55:34:10:1; 56:33:10:1; 57:32:10:1; 58:31:10:1; 59:30:10:1; 60:29:10:1; 61:28:10:1; 62:27:10:1; 63:26:10:1; 64:25:10:1; and 65:24:10:1.

The composition may comprise a cationic lipid having the structure

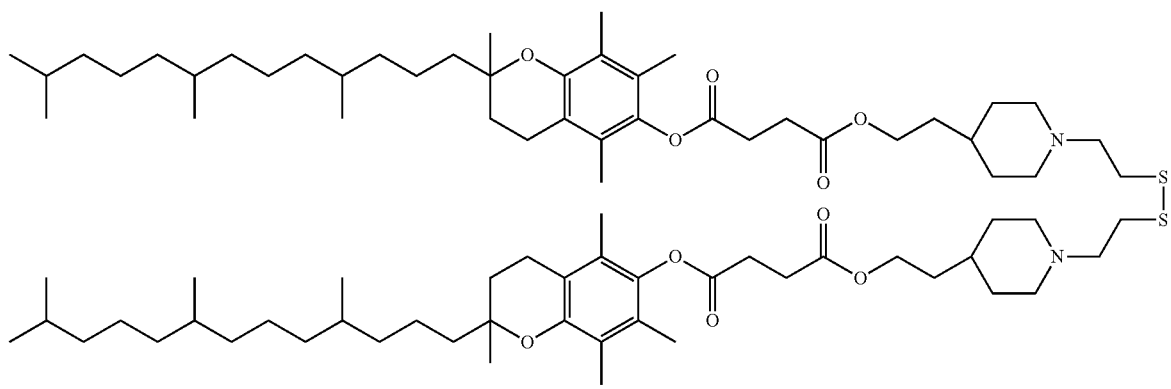 [SMILES: Cc1c(C)c2c(c(C)c1OC(=O)CCC(=O)OCCC1CCN(CCSSCCN3CCC(CCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2]

a steroid having the structure

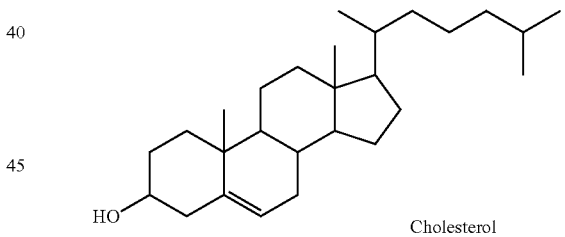

Cholesterol a phosphatidylethanolamine phospholipid having the structure

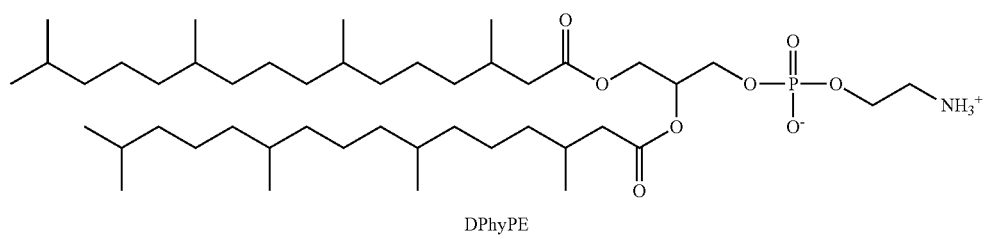 [SMILES: CC(C)CCCC(C)CCCC(C)CCCC(C)CC(=O)OCC(COP(=O)([O-])OCC[NH3+])OC(=O)CC(C)CCCC(C)CCCC(C)CCCC(C)C]

DPhyPE and a PEGylated lipid having the structure

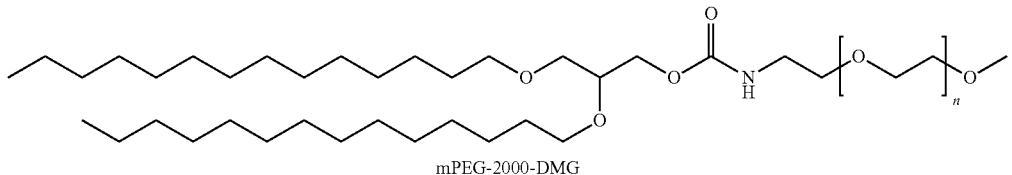

mPEG-2000-DMG

Neutral liposome compositions may be formed from, for example, dimyristoyl phosphatidylcholine (DMPC) or dipalmitoyl phosphatidylcholine (DPPC). Anionic liposome compositions may be formed from dimyristoyl phosphatidylglycerol, while anionic fusogenic liposomes may be formed primarily from dioleoyl phosphatidylethanolamine (DOPE). Another type of liposomal composition may be formed from phosphatidylcholine (PC) such as, for example, soybean PC, and egg PC. Another type is formed from mixtures of phospholipid and/or phosphatidylcholine and/or cholesterol.

A positively charged synthetic cationic lipid, N—[I-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells. DOTMA analogues can also be used to form liposomes.

Derivatives and analogues of lipids described herein may also be used to form liposomes.

A liposome containing a nucleic acid can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The nucleic acid preparation is then added to the micelles that include the lipid component. The cationic groups on the lipid interact with the nucleic acid and condense around the nucleic acid to form a liposome. After condensation, the detergent is removed, e.g., by dialysis, to yield a liposomal preparation of nucleic acid.

If necessary a carrier compound that assists in condensation can be added during the condensation reaction, e.g., by controlled addition. For example, the carrier compound can be a polymer other than a nucleic acid (e.g., spermine or spermidine). pH can also be adjusted to favour condensation.

Nucleic acid formulations may include a surfactant. In one embodiment, the nucleic acid is formulated as an emulsion that includes a surfactant.

A surfactant that is not ionized is a non-ionic surfactant. Examples include non-ionic esters, such as ethylene glycol esters, propylene glycol esters, glyceryl esters etc., nonionic alkanolamides, and ethers such as fatty alcohol ethoxylates, propoxylated alcohols, and ethoxylated/propoxylated block polymers.

A surfactant that carries a negative charge when dissolved or dispersed in water is an anionic surfactant. Examples include carboxylates, such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates.

A surfactant that carries a positive charge when dissolved or dispersed in water is a cationic surfactant. Examples include quaternary ammonium salts and ethoxylated amines.

A surfactant that has the ability to carry either a positive or negative charge is an amphoteric surfactant. Examples include acrylic acid derivatives, substituted alkylamides, N-alkylbetaines and phosphatides.

"Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic. A micelle may be formed by mixing an aqueous solution of the nucleic acid, an alkali metal alkyl sulphate, and at least one micelle forming compound.

Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof.

Phenol and/or m-cresol may be added to the mixed micellar composition to act as a stabiliser and preservative. An isotonic agent such as glycerine may as be added.

A nucleic acid preparation may be incorporated into a particle such as a microparticle. Microparticles can be produced by spray-drying, lyophilisation, evaporation, fluid bed drying, vacuum drying, or a combination of these methods.

The present invention also provides pharmaceutical compositions comprising the nucleic acid or conjugated nucleic acid of the invention. The pharmaceutical compositions may be used as medicaments or as diagnostic agents, alone or in combination with other agents. For example, a nucleic acid or conjugated nucleic acid of the invention can be combined with a delivery vehicle (e.g., liposomes) and excipients, such as carriers, diluents. Other agents such as preservatives and stabilizers can also be added. Methods for the delivery of a nucleic acid or conjugated nucleic acid are known in the art and within the knowledge of the person skilled in the art.

The nucleic acid or conjugated nucleic acid of the present invention can also be administered in combination with other therapeutic compounds, either administrated separately or simultaneously, e.g., as a combined unit dose. The invention also includes a pharmaceutical composition comprising a nucleic acid or conjugated nucleic acid according to the present invention in a physiologically/pharmaceutically acceptable excipient, such as a stabilizer, preservative, diluent, buffer, and the like.

The pharmaceutical composition may be specially formulated for administration in solid or liquid form. The composition may be formulated for oral administration, parenteral administration (including, for example, subcutaneous, intramuscular, intravenous, or epidural injection), topical application, intravaginal or intrarectal administration, sublingual administration, ocular administration, transdermal administration, or nasal administration. Delivery using subcutaneous or intravenous methods are preferred.

Dosage levels for the medicament and pharmaceutical compositions of the invention can be determined by those skilled in the art by routine experimentation. In one embodiment, a unit dose may contain between about 0.01 mg/kg and about 100 mg/kg body weight of nucleic acid. Alternatively, the dose can be from 10 mg/kg to 25 mg/kg body weight, or 1 mg/kg to 10 mg/kg body weight, or 0.05 mg/kg to 5 mg/kg body weight, or 0.1 mg/kg to 5 mg/kg body weight, or 0.1 mg/kg to 1 mg/kg body weight, or 0.1 mg/kg to 0.5 mg/kg body weight, or 0.5 mg/kg to 1 mg/kg body weight. Dosage levels may also be calculated via other parameters such as, e.g., body surface area.

The pharmaceutical composition may be a sterile injectable aqueous suspension or solution, or in a lyophilized form. In one embodiment, the pharmaceutical composition may comprise lyophilized lipoplexes or an aqueous suspension of lipoplexes. The lipoplexes preferably comprises a nucleic acid of the present invention. Such lipoplexes may be used to deliver the nucleic acid of the invention to a target cell either in vitro or in vivo.

The pharmaceutical compositions and medicaments of the present invention may be administered to a mammalian subject in a pharmaceutically effective dose. The mammal may be selected from humans, dogs, cats, horses, cattle, pig, goat, sheep, mouse, rat, hamster and guinea pig.

A further aspect of the invention relates to a nucleic acid or conjugated nucleic acid of the invention or the pharmaceutical composition comprising the nucleic acid or conjugated nucleic acid of the invention for use in the treatment or prevention of a disease or disorder. The invention includes a pharmaceutical composition comprising one or more RNAi molecules according to the present invention in a physiologically/pharmaceutically acceptable excipient, such as a stabiliser, preservative, diluent, buffer and the like.

The pharmaceutical composition may be a sterile injectable aqueous suspension or solution, or in a lyophilised form.

Pharmaceutically acceptable compositions may comprise a therapeutically-effective amount of one or more nucleic acid(s) in any embodiment according to the invention, taken alone or formulated with one or more pharmaceutically acceptable carriers, excipient and/or diluents.

Examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; and (22) other non-toxic compatible substances employed in pharmaceutical formulations.

Stabilisers may be agents that stabilise the nucleic acid agent, for example a protein that can complex with the nucleic acid, chelators (e.g. EDTA), salts, RNAse inhibitors, and DNAse inhibitors.

In some cases it is desirable to slow the absorption of the drug from subcutaneous or intramuscular injection in order to prolong the effect of a drug. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

The nucleic acid described herein may be capable of inhibiting the expression of a target gene in a cell. The nucleic acid described herein may be capable of partially inhibiting the expression of a target gene in a cell. Inhibition may be complete, i.e. 0% of the expression level of target gene expression in the absence of the nucleic acid of the invention. Inhibition of target gene expression may be partial, i.e. it may be 15%, 20%, 30%, 40%, 50%, 60%, 70%, 75%, 80%, 85%, 90%, 95% of target gene expression in the absence of a nucleic acid of the invention. Inhibition may last 4 weeks, 5 weeks, 6 weeks, 7 weeks, 8 weeks, 10 weeks, 11 weeks, 12 weeks, 13 weeks, 14 weeks or up to 3 months, when used in a subject, such as a human subject. The nucleic acid or composition comprising the nucleic acid composition may be for use once, every week, every two weeks, every three weeks, every four weeks, every five weeks, every six weeks, every seven weeks, or every eight weeks. The nucleic acid may be for use subcutaneously, intravenously or using any other application routes such as oral, rectal or intraperitoneal.

In cells and/or subjects treated with or receiving the nucleic acid of the present invention, the target gene expression may be inhibited compared to untreated cells and/or subjects by at least about 30%, 35%, 40%, 45%, 50%, 55%, 60%, 65%, 70%, 75%, 80%, 85%, 90%, 95%, 98%, or 100%. The level of inhibition may allow treatment of a disease associated with target gene expression or overexpression, or may allow further investigation into the functions of the target gene product.

The target gene may be Factor VII, Eg5, PCSK9, TPX2, apoB, SAA, TTR, RSV, PDGF beta gene, Erb-B gene, Src gene, CRK gene, GRB2 gene, RAS gene, MEKK gene, JNK gene, RAF gene, Erkl/2 gene, PCNA(p21) gene, MYB gene, JU gene, FOS gene, BCL-2 gene, hepcidin, Activated Protein C, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, topoisomerase I gene, topoisomerase II alpha gene, mutations in the p73 gene, mutations in the p21(WAF I/CIPI) gene, mutations in the p27(KIPI) gene, mutations in the PPM ID gene, mutations in the RAS gene, mutations in the caveolin I gene, mutations in the MIB I gene, mutations in the MTAI gene, mutations in the M68 gene, mutations in tumor suppressor genes, and mutations in the p53 tumor suppressor gene.

A further aspect of the invention relates to nucleic acid of the invention in the manufacture of a medicament for treating or preventing a disease or disorder.

Also included in the invention is a method of treating or preventing a disease or disorder comprising administration of a pharmaceutical composition comprising a nucleic acid or conjugated nucleic acid as described herein, to an individual in need of treatment. The nucleic acid composition may be administered twice every week, once every week, every two weeks, every three weeks, every four weeks, every five weeks, every six weeks, every seven weeks, or every eight weeks. The nucleic acid or conjugated nucleic acid may be administered to the subject subcutaneously, intravenously or using any other application routes such as oral, rectal or intraperitoneal.

In one embodiment, a subject is administered an initial dose and one or more maintenance doses of a nucleic acid agent. The maintenance dose or doses can be the same or lower than the initial dose, e.g., one-half less of the initial dose. The maintenance doses are, for example, administered no more than once every 2, 5, 10, or 30 days. The treatment regimen may last for a period of time which will vary depending upon the nature of the particular disease, its severity and the overall condition of the patient.

In one embodiment, the composition includes a plurality of nucleic acid agent species. In another embodiment, the nucleic acid agent species has sequences that are non-overlapping and non-adjacent to another species with respect to a naturally occurring target sequence. In another embodiment, the plurality of nucleic acid agent species is specific for different naturally occurring target genes. In another embodiment, the nucleic acid agent is allele specific.

The nucleic acid or conjugated nucleic acid of the present invention can also be administered or for use in combination with other therapeutic compounds, either administered separately or simultaneously, e.g. as a combined unit dose.

The nucleic acid or conjugated nucleic acid of the present invention can be produced using routine methods in the art including chemically synthesis or expressing the nucleic acid either in vitro (e.g., run off transcription) or in vivo. For example, using solid phase chemical synthesis or using an expression vector. In one embodiment, the expression vector can produce the nucleic acid of the invention in a target cell. Methods for the synthesis of the nucleic acid described herein are known to persons skilled in the art.

Another aspect of the invention includes any nucleic acid, method, use or composition disclosed herein, wherein there is no terminal phosphorothioate in the nucleic acid.

Another aspect of the invention includes any nucleic acid, method, use or composition disclosed herein, wherein the terminal nucleotide is located at the 3' end of at least one of the first strand and the second strand, or both.

Another aspect of the invention includes any nucleic acid, method, use or composition disclosed herein, wherein the ligand does not contain a phosphorothioate, such as a nucleic acid according conjugated to a Galnac moiety which does not contain phosphorothioates.

The invention will now be described with reference to the following non-limiting figures and examples in which:

FIG. 1 shows the 3'-3' and 5'-5' linkages used to form an inverted nucleotide;

FIG. 2 shows siRNA sequences targeting TMPRSS6 with inverted RNA nucleotides at 3'-ends of first and second strand; Duplex ID (SEQ ID NO: top; bottom): TMP01 (1; 2), TMP70 (3; 4), TMP71 (5; 6), TMP72 (7; 8), TMP73 (9; 10), TMP74 (11; 12), TMP75 (13; 14), TMP76 (15; 16), TMP77 (17; 18), TMP78 (19; 20);

FIG. 7 shows the structure of an example of a GalNac ligand referred to herein;

FIG. 8 shows siRNA sequences targeting TMPRSS6 with phosphorothioate-linked inverted RNA nucleotides; Duplex ID (SEQ ID NO: top; bottom): TMP70 (3; 4), TMP82 (21; 22), TMP83 (23; 24);

FIG. 19 shows the in vivo activity of GalNAc-conjugated siRNAs targeting ALDH2 with ivA at the first strand 3'-end in mice;

FIGS. 20 and 21 show in vitro activity of GalNAc-conjugated siRNAs against ALDH2 (STS22006) containing inverted RNA nucleotides in addition to terminal nucleotides. Duplex ID (SEQ ID NO: top; bottom): STS22006L6 (79; 80), STS22006V7L6 (81; 82), STS22006V8L6 (83; 84), STS22006V9L6 (85; 86), STS22006V10L35 (87; 88).

FIGS. 22 and 23 show in vitro activity of GalNAc-conjugated siRNAs against ALDH2 (STS22009) containing inverted RNA nucleotides in addition to terminal nucleotides. Duplex ID (SEQ ID NO: top; bottom): STS22009L6 (89; 90), STS22009V3L6 (91; 92), STS22009V4L6 (93; 94), STS22009V5L6 (95; 96), STS22009V6L35 (97; 98).

FIGS. 24 and 25 show in vitro activity of GalNAc-conjugated siRNAs against TTR containing inverted RNA nucleotides in addition to terminal nucleotides. Duplex ID (SEQ ID NO: top; bottom): STS16001L1 (99; 100), STS16001V11L1 (101; 102), STS16001V12L1 (103; 104), STS16001V13L1 (105; 106), STS16001V14L35 (107; 108).

FIGS. 26 and 27 show in vitro activity of GalNAc-conjugated siRNAs against ALDH2 containing inverted RNA nucleotides at 3'-ends instead of the last nucleotide. Duplex ID (SEQ ID NO: top; bottom): STS22002L6 (109; 110), STS22002V8L6 (111; 112), STS22002V9L6 (113; 114), STS22002V10L6 (115; 116).

FIGS. 28 and 29 show in vivo activity of different modified variants of the GalNAc-siRNA conjugates STS22006 and STS22009 in mice. Duplex ID (SEQ ID NO: top; bottom): STS22006L6 (79; 80), STS22006V1 L6 (117; 118), STS22009L6 (89; 90), STS22009V1 L6 (119; 120), STS22009V2L6 (121; 122).

FIG. 30 shows siRNA sequences with 5'-5'-linked ribonucleotides. Duplex ID (SEQ ID NO: top; bottom): STS18001L4 (166; 167), STS16001V4L11 (168; 169), STS16001L22 (170; 171), STS16001V7L22 (172; 173), STS16001V8L22 (174; 175), STS16001V9L22 (176; 177), STS16001V10L22 (178; 179), STS16001V6L11 (180; 181), STS16001V7L11 (182; 183), STS16001V8L11 (184; 185), STS16001V9L11 (186; 187).

EXAMPLES

Figure 3:
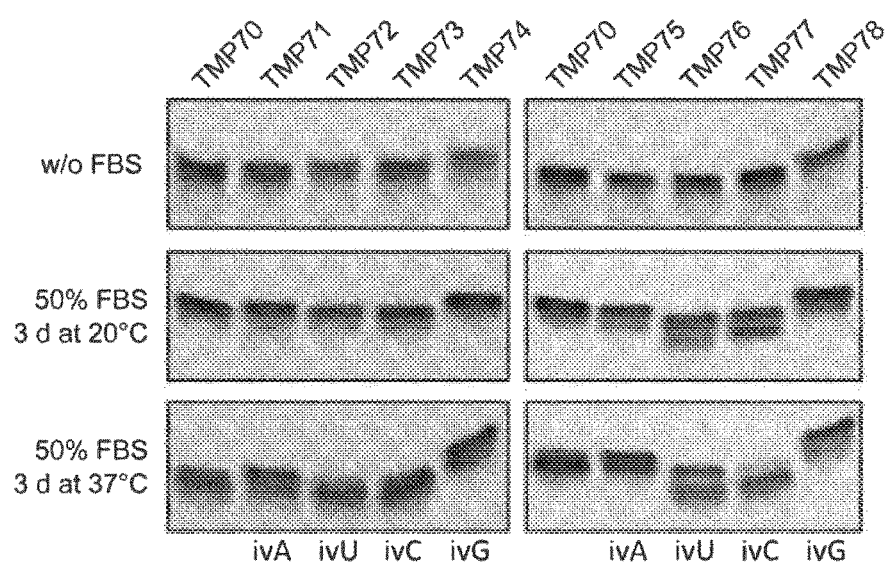
FIGS. 3 and 4 show the serum stability of ivR-modified siRNAs.

Example 1 siRNA Modification: Using Inverted Nucleotides.

The terminal nucleotide at the 3' end of an oligonucleotide strand can be attached to the adjacent nucleotide via the 3' carbon of the terminal nucleotide and the 3' carbon of the adjacent nucleotide to form a 3'-3'-inverted nucleotide (FIG. 1A). Likewise, the terminal nucleotide at the 5' end of an oligonucleotide strand can be attached to the adjacent nucleotide via the 5' carbon of the terminal nucleotide and the 5' carbon of the adjacent nucleotide to form a 5'-5'-inverted nucleotide (FIG. 1B). 5'-3', 3'-3' and 5'-5' phosphodiester linkages are shown in FIG. 1.

Example 2 siRNA Modification: Synthesis of siRNA with Inverted Nucleotides.

All Oligonucleotides were either obtained from a commercial oligonucleotide manufacturer (Eurogentech, Belgium) or synthesized on an AKTA oligopilot synthesizer using standard phosphoramidite chemistry. Commercially available solid support and 2'O-Methyl RNA phosphoramidtes, 2'Fluoro DNA phosphoramidites (all standard protection) and commercially available long trebler phosphoramidite (Glen research) were used. Synthesis was performed using 0.1 M solutions of the phosphoramidite in dry acetonitrile and benzylthiotetrazole (BTT) was used as activator (0.3M in acetonitrile). All other reagents were commercially available standard reagents.

Conjugation of the GalNac synthon (ST23) or treblers ST41 and ST43 was achieved by coupling of the respective phosphoramidite to the 5'end of the oligochain under standard phosphoramidite coupling conditions. Phosphorothioates were introduced using standard commercially available thiolation reagents (EDITH, Link technologies).

ST23 is a GalNac C4 phosphoramidite (structure components as below)

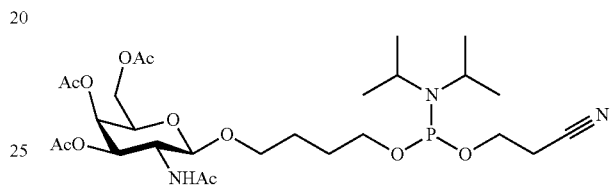

ltrb is as follows:

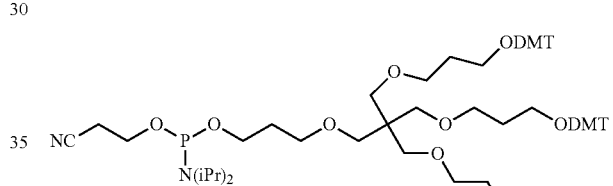

Long Trebler (Ltrb)

ST41 is as follows (and as described in WO2017/174657):

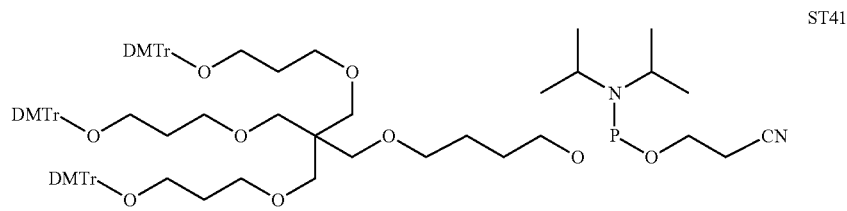

ST41

ST43 is as follows (and as described in WO2017/174657):

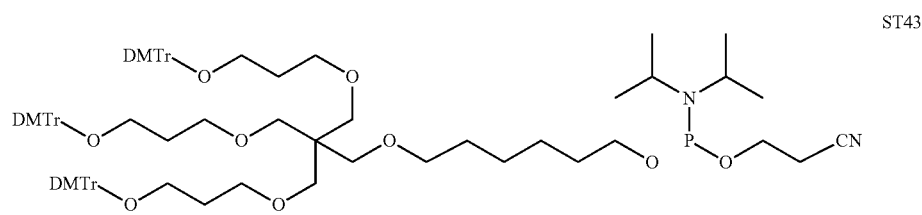

ST43

The single strands were cleaved off the CPG by using Methylamine. Where TBDMS protected RNA nucleosides were used, additional treatment with TEA*3HF was performed to remove the silyl protection, as known in the art. The resulting crude oligonucleotide was purified by Ionexchange chromatography (Resource Q, 6 mL, GE Healthcare) on a AKTA Pure HPLC System using a Sodium chloride gradient. Product containing fractions were pooled, desalted on a size exclusion column (Zetadex, EMP Biotech) and lyophilised.

For Duplexation, equimolar amounts of the respective single strands were dissolved in water and heated to 80° C. for 5 min. After cooling the resulting Duplex was lyophilised.

Example 3 siRNAs Containing Different Inverted RNA Bases in their 3'-Terminal Positions were Tested for Serum Stability.

All siRNAs are modified by alternating 2'-OMe/2'-F in both strands, such that every 2'-OMe modified nucleotide on the first strand is paired with a 2'-F modified nucleotide on the second strand. TMP70 comprises two terminal phosphorothioates at 5'- and 3'-ends of both strands. TMP71-74 are modified by terminal phosphorothioates at 5'- and 3'-ends and one additional inverted nucleotide (A, U, C, G) at their 3'-ends. In contrast, TMP75-78 each have two phosphorothioate at the 5'-ends, no phosphorothioate at the 3'-ends and one additional inverted nucleotide (A, U, C, G) at the 3'-ends. Inverted RNA nucleotides are attached via a phosphodiester linkage.

Serum stability of ivR-modified siRNAs was tested. "w/o FBS" and "UT" indicates untreated samples. "FBS" indicates siRNA duplexes which were incubated at 5 µM final concentration with 50% FBS for 3 d, phenol/chloroform-extracted and precipitated with Ethanol. Samples were analyzed on 20% TBE polyacrylamide gels in native gel electrophoresis. TMP75 (which includes an inverted A) and TMP78 (which includes an inverted G) are more stable than TMP70.

Figure 4:
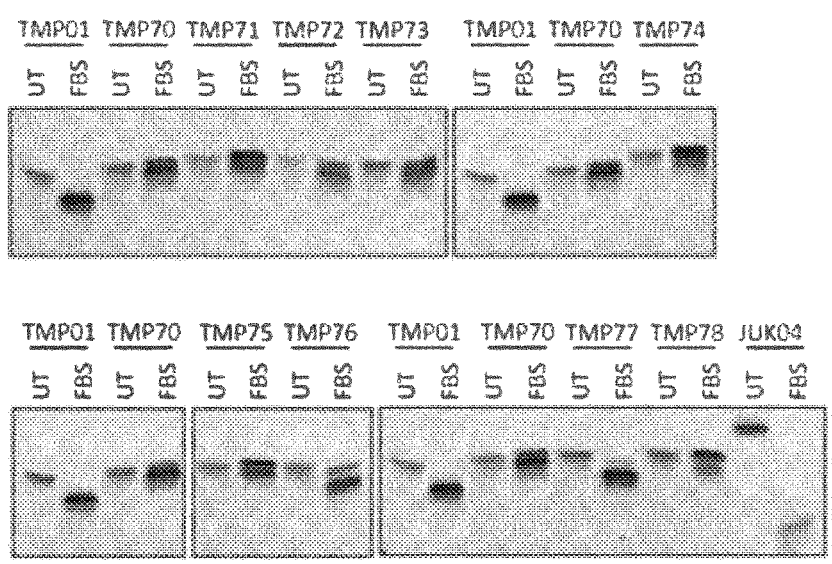

Data are shown in FIGS. 2-4.

Example 4

The influence of inverted RNA nucleotides at terminal 3' positions was analyzed using an siRNA against TMPRSS6. TMP70-TMP74 contain phosphorothioates at all termini, whereas TMP75-TMP78 do not contain terminal phosphorothioates at the 3'-ends of both strands. Inverted RNA nucleotides are present in addition to the terminal nucleotide as inverted A (TMP71, TMP75), inverted U (TMP72, TMP76), inverted C (TMP 73, TMP77) and inverted G (TMP74, TMP78). These siRNAs were tested for knockdown of the target gene in vitro. A non-related siRNA (PTEN) and a non-targeting siRNA (Luci) were included as controls. All tested variants show comparable activity under the tested conditions.

The experiment was conducted in Hep3B. Cells were seeded at a density of 150,000 cells per 6-well, transfected with 0.1 and 1 nM siRNA and 1 µg/ml Atufect after 24 h and lysed after 48 h. Total RNA was extracted and TMPRSS6 and Actin mRNA levels were determined by Taqman qRT-PCR. Each bar represents mean±SD of three technical replicates.

Knockdown activity of ivR-modified siRNAs in vitro was tested. A Hep3B cell line was seeded at a density of 150,000 cells per 6-well. Experimental conditions: 0.1 and 1 nM siRNA, 1 µg/ml Atufect, lysis 48 hpt. All variants were found to be equally active in vitro.

Figure 5:
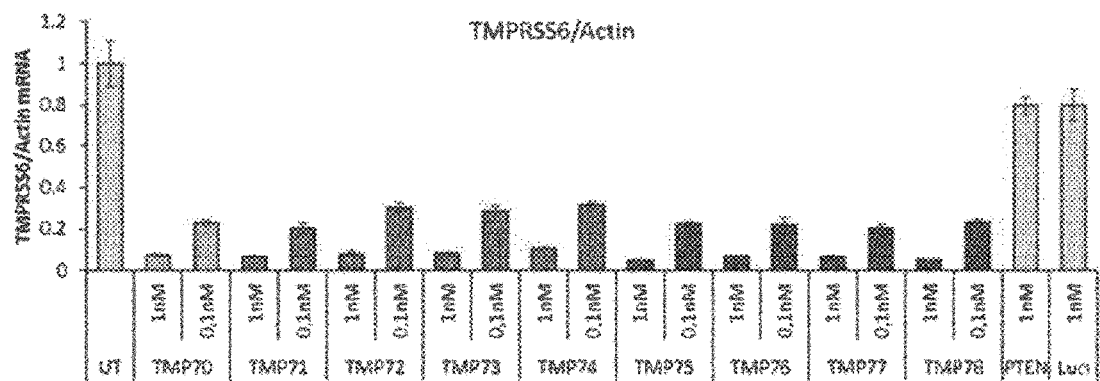
FIG. 5 shows the in vitro knockdown activity of ivR-modified siRNAs.

Data are shown in FIGS. 2 and 5.

Example 5

The influence of inverted A and G RNA nucleotides at terminal 3' positions was analyzed using an siRNA against TMPRSS6. TMP70 contains phosphorothioates at all termini, whereas TMP75 contains ivA and TMP78 contains ivG at the 3'-ends of both first and second strand. At these ends, ivA and ivG substitute for terminal phosphorothioates and are present in addition to the terminal nucleotide of the respective strands. The siRNA were tested for target knockdown in vitro. A non-related siRNA (PTEN) and a non-targeting siRNA (Luci) were included as controls. All tested variants show comparable activity under the tested conditions.

The experiment was conducted in Hep3B. Cells were seeded at a density of 150,000 cells per 6-well, transfected with 5 to 0.00016 nM siRNA and 1 µg/ml Atufect after 24 h and lysed after 48 h. Total RNA was extracted and TMPRSS6 and Actin mRNA levels were determined by Taqman qRT-PCR. Each bar represents mean±SD of three technical replicates.

Figure 6:
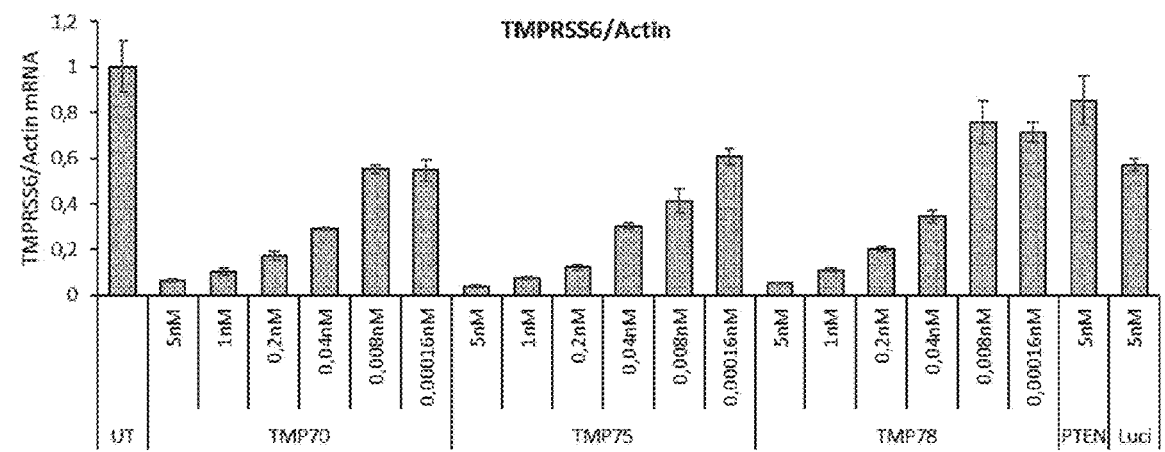
FIG. 6 shows the in vitro knockdown activity of selected ivR-modified siRNAs.

Data are shown in FIGS. 2 and 6.

Example 6

The influence of inverted A and G RNA nucleotides at terminal 3' positions was analysed using an siRNA against TMPRSS6. TMP70 contains each two phosphorothioate linkages at all termini, whereas TMP82 and TMP83 contain ivA (TMP82) and ivG (TMP83) at the 3'-end of the first strand and at the 3'-end of the second strand. Both inverted nucleotides are present in addition to the terminal nucleotide of the respective strands and are linked via a phosphorothioate bond. A non-related siRNA (PTEN) and a non-targeting siRNA (Luci) were included as controls. All tested variants show comparable activity under the tested conditions.

Figure 9:
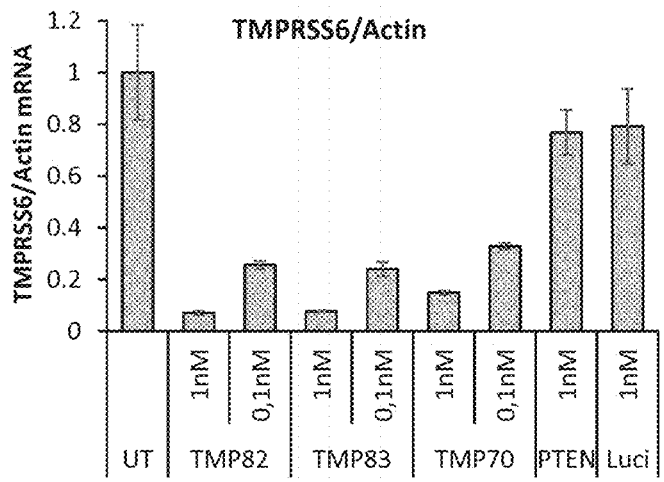
FIG. 9 shows in vitro activity siRNAs with phosphorothioate-linked inverted A and G RNA nucleotides at terminal 3' positions.

The experiment was conducted in Hep3B. Cells were seeded at a density of 150,000 cells per 6-well, transfected with 1 nM and 0.1 nM siRNA and 1 µg/ml Atufect after 24 h and lysed after 48 h. Total RNA was extracted and TMPRSS6 and Actin mRNA levels were determined by Taqman qRT-PCR. The results are shown in FIG. 9. Each bar represents mean±SD from three technical replicates.

Data are shown in FIGS. 8 and 9.

Example 7

Different siRNA duplexes containing inverted RNA nucleotides at both 3'-ends were tested for serum stability. TMP84-TMP87 contain inverted RNA in addition to the last nucleotide in the second strand and instead of the last nucleotide in the first strand. TMP88-TMP91 contain inverted RNA in addition to the last nucleotide in the first strand and instead of the last nucleotide in the second strand. All inverted RNA nucleotides substitute for terminally used phosphorothioates. In the design of TMP84-TMP87, ivA and ivG confer higher stability to the tested sequence than ivU and ivC (part A). In the design of TMP88-TMP91, there is no influence of base identity on duplex stability (part B).

Figure 10:
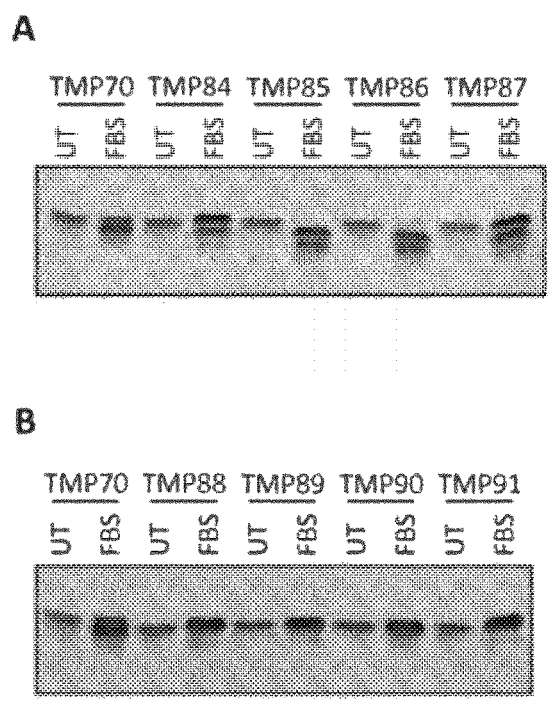
FIG. 10 shows the serum stability of different siRNA duplexes containing inverted RNA nucleotides at both 3'-ends.

"UT" indicates untreated samples. "FBS" indicates siRNA duplexes which were incubated at 5 µM final concentration with 50% FBS for 3 d, phenol/chloroform-extracted and precipitated with Ethanol. Samples were analysed on 20% TBE polyacrylamide gels in native gel electrophoresis and results are shown in FIG. 10.

Sequences are set out in Table 1.

TABLE 1

Different siRNA duplexes containing inverted RNA nucleotides at both 3'-ends.

| Duplex ID | sequence and chemistry<br>top: first strand,<br>bottom: second strand, both 5'-3' |
|---|---|
| TMP70 | mA(ps)fA(ps)mCfCmAfGmAfAmGfAmAfGmCfAmGfGmU(ps)fG(ps)mA<br>fU(ps)mC(ps)fAmCfCmUfGmCfUmUfCmUfUmCfUmGfG(ps)mU(ps)fU |
| TMP84 | mA(ps)fA(ps)mCfCmAfGmAfAmGfAmAfGmCfAmGfGmU fG ivA<br>fU(ps)mC(ps)fAmCfCmUfGmCfUmUfCmUfUmCfUmGfG mUfU ivG |
| TMP85 | mA(ps)fA(ps)mCfCmAfGmAfAmGfAmAfGmCfAmGfGmU fG ivU<br>fU(ps)mC(ps)fAmCfCmUfGmCfUmUfCmUfUmCfUmGfG mUfU ivG |
| TMP86 | mA(ps)fA(ps)mCfCmAfGmAfAmGfAmAfGmCfAmGfGmU fG ivC<br>fU(ps)mC(ps)fAmCfCmUfGmCfUmUfCmUfUmCfUmGfG mUfU ivG |
| TMP87 | mA(ps)fA(ps)mCfCmAfGmAfAmGfAmAfGmCfAmGfGmU fG ivG<br>fU(ps)mC(ps)fAmCfCmUfGmCfUmUfCmUfUmCfUmGfG mUfU ivG |
| TMP88 | mA(ps)fA(ps)mCfCmAfGmAfAmGfAmAfGmCfAmGfGmU fGmA ivG<br>fU(ps)mC(ps)fAmCfCmUfGmCfUmUfCmUfUmCfUmGfG mU ivA |
| TMP89 | mA(ps)fA(ps)mCfCmAfGmAfAmGfAmAfGmCfAmGfGmU fGmA ivG<br>fU(ps)mC(ps)fAmCfCmUfGmCfUmUfCmUfUmCfUmGfG mU ivU |
| TMP90 | mA(ps)fA(ps)mCfCmAfGmAfAmGfAmAfGmCfAmGfGmU fGmA ivG<br>fU(ps)mC(ps)fAmCfCmUfGmCfUmUfCmUfUmCfUmGfG mU ivC |
| TMP91 | mA(ps)fA(ps)mCfCmAfGmAfAmGfAmAfGmCfAmGfGmU fGmA ivG<br>fU(ps)mC(ps)fAmCfCmUfGmCfUmUfCmUfUmCfUmGfG mU ivG |

Duplex ID (SEQ ID NO: top; bottom):
TMP70 (SEQ ID NO: 3; 4),
TMP84 (SEQ ID NO: 25; 26), TMP85 (SEQ ID NO: 27; 28),
TMP86 (SEQ ID NO: 29; 30), TMP87 (SEQ ID NO: 31; 32),
TMP88 (SEQ ID NO: 33; 34), TMP89 (SEQ ID NO: 35; 36),
TMP90 (SEQ ID NO: 37; 38), TMP91 (SEQ ID NO: 39; 40).
mA, mU, mC, mG-2'-OMe RNA
fA, fU, fC, fG-2'-F RNA
ivA, ivU, ivC, ivG-inverted RNA (3'-3')
(ps)-phosphorothioate Example 8

The influence of inverted RNA nucleotides at terminal 3' positions was analysed using an siRNA against TMPRSS6. Sequences are set out in Table 1. TMP70 contains phosphorothioates at all termini, whereas TMP84-TMP87 contain ivG at the 3'-end of the second strand. The inverted RNA nucleotide is present in addition to the last nucleotide and substitutes for two terminal phosphorothioates. At the first strand 3'-end, ivA (TMP84), ivU (TMP85), ivC (TMP86) and ivG (TMP87) were tested. These inverted RNA nucleotides were added instead of the terminal nucleotide and substitute for phosphorothioates. A non-related siRNA (PTEN) and a non-targeting siRNA (Luci) were included as controls. All tested variants show comparable activity under the tested conditions.

Figure 11:
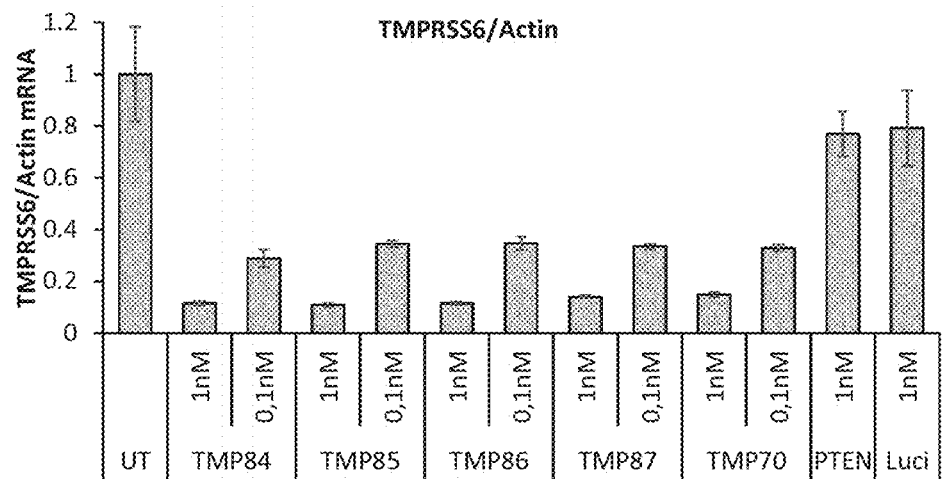
FIG. 11 shows in vitro activity of siRNAs targeting TMPRSS6 with inverted RNA nucleotides at terminal 3' positions.

The experiment was conducted in Hep3B. Cells were seeded at a density of 150,000 cells per 6-well, transfected with 1 nM and 0.1 nM siRNA and 1 µg/ml Atufect after 24 h and lysed after 48 h. Total RNA was extracted and TMPRSS6 and Actin mRNA levels were determined by Taqman qRT-PCR. Results are shown in FIG. 11. Each bar represents mean±SD of three technical replicates.

Example 9

The influence of inverted RNA nucleotides at terminal 3' positions was analysed using an siRNA against TMPRSS6. The sequences are set out in Table 1. TMP70 contains phosphorothioates at all termini, whereas TMP88-TMP91 contain ivG at the 3'-end of the first strand. The inverted RNA nucleotide is present in addition to the last nucleotide and substitutes for two phosphorothioates. At the second strand 3'-end, ivA (TMP88), ivU (TMP89), ivC (TMP90) and ivG (TMP91) were tested. These inverted RNA nucleotides were added instead of the terminal nucleotide and substitute for phosphorothioates. A non-related siRNA (PTEN) and a non-targeting siRNA (Luci) were included as controls. All tested variants show comparable activity under the tested conditions.

Figure 12:
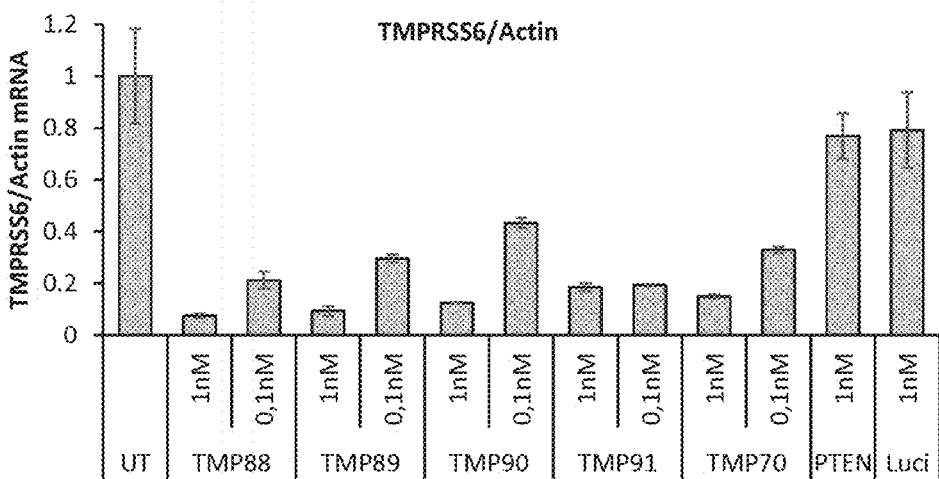
FIG. 12 shows in vitro activity of siRNAs targeting TMPRSS6 with inverted RNA nucleotides at terminal 3' positions.

The experiment was conducted in Hep3B. Cells were seeded at a density of 150,000 cells per 6-well, transfected with 1 nM and 0.1 nM siRNA and 1 µg/ml Atufect after 24 h and lysed after 48 h. Total RNA was extracted and TMPRSS6 and Actin mRNA levels were determined by Taqman qRT-PCR. Results are shown in FIG. 12. Each bar represents mean±SD of three technical replicates.

Example 10

The influence of inverted RNA nucleotides at terminal 3' positions was analysed using a GalNAc-siRNA conjugate targeting TMPRSS6 in liposomal transfections. STS12009-L4 contains phosphorothioates at all non-conjugated termini, whereas the tested variants contain an inverted RNA nucleotide at the 3'-ends of both first and second strand. The inverted RNA is present in addition to the last nucleotide and substitutes for two terminal phosphorothioates (STS12009V10-L4 and -V11-L4) or is used in addition to two terminal phosphorothioates (STS12009V29-L4 and STS12009V30-L4). Inverted A (STS12009V10-L4 and -V29-L4) and inverted G (STS12009V11-L4 and -V30-L4) were used. All tested variants show comparable activity under the tested conditions.

The experiment was conducted in Hep3B. Cells were seeded at a density of 150,000 cells per 6-well, transfected with 5 nM to 0.0016 nM siRNA and 1 µg/ml Atufect after 24 h and lysed after 48 h. Total RNA was extracted and TMPRSS6 and Actin mRNA levels were determined by Taqman qRT-PCR. Each bar represents mean±SD of three technical replicates.

Figure 13:
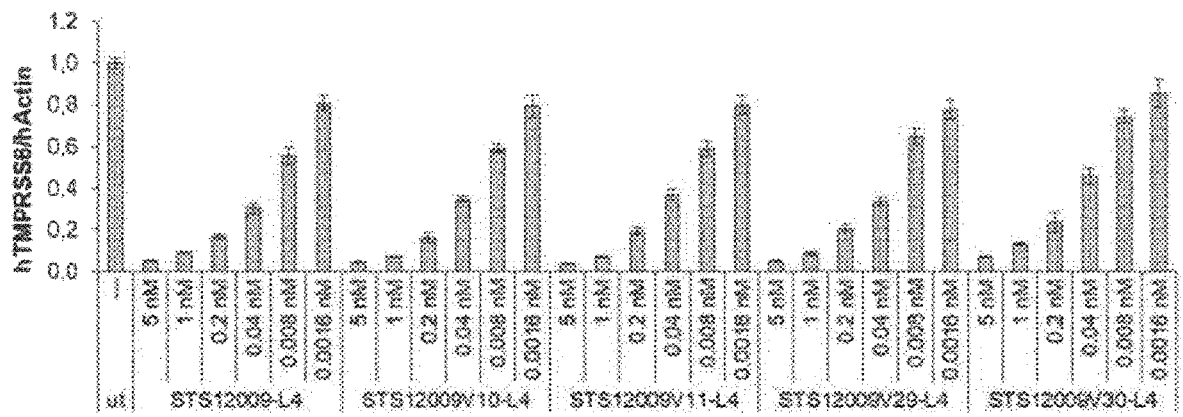
FIG. 13 shows the in vitro activity of a GalNAc-conjugated siRNA targeting TMPRSS6 and containing inverted RNA nucleotides at terminal 3' positions after liposomal transfection.

Sequences are listed in Table 2 and results are shown in FIG. 13.

TABLE 2

GalNAc-siRNA conjugates targeting TMPRSS6
sequence were used to investigate the influence of
inverted RNA nucleotides at terminal 3' positions.

| Duplex ID | sequence chemistry<br>top: first strand,<br>bottom: second strand, both 5'-3' |
|---|---|
| STS12009L4 | mA(ps)fA(ps)mCfCmAfGmAfAmGfAmAfGmCf<br>AmGfGmU(ps)fG(ps)mA<br>[ST23(ps)]3 ST41(ps)fUmCfAmCfCmUfGm<br>CfUmUfCmUfUmCfUmGfG(ps)mU(ps)fU |
| STS12009V10L4 | mA(ps)fA(ps)mCfCmAfGmAfAmGfAmAfGmCf<br>AmGfGmUfGmA ivA<br>[ST23(ps)]3 ST41(ps)fUmCfAmCfCmUfGm<br>CfUmUfCmUfUmCfUmGfGmUfU ivA |
| STS12009V11L4 | mA(ps)fA(ps)mCfCmAfGmAfAmGfAmAfGmCf<br>AmGfGmUfGmA ivG<br>[ST23(ps)]3 ST41(ps)fUmCfAmCfCmUfGm<br>CfUmUfCmUfUmCfUmGfGmUfU ivG |
| STS12009V29L4 | mA(ps)fA(ps)mCfCmAfGmAfAmGfAmAfGmCf<br>AmGfGmU(ps)fG(ps)mA ivA<br>[ST23(ps)]3 ST41(ps)fUmCfAmCfCmUfGm<br>CfUmUfCmUfUmCfUmGfG(ps)mU(ps)fU ivA |
| STS12009V30L4 | mA(ps)fA(ps)mCfCmAfGmAfAmGfAmAfGmCf<br>AmGfGmU(ps)fG(ps)mA ivG<br>[ST23(ps)]3 ST41(ps)fUmCfAmCfCmUfGm<br>CfUmUfCmUfUmCfUmGfG(ps)mU(ps)fUivG |

Duplex ID (SEQ ID NO: top; bottom):
STS12009L4 (41; 42), STS12009V10L4 (43; 44),
STS12009V11L4 (45; 46), STS12009V29L4 (47; 48),
STS12009V30L4 (49; 50).
mA, mU, mC, mG-2'OMe RNA
fA, fU, fC, fG-2'F RNA
ivA, ivG-inverted RNA (3'-3')
(ps)-phosphorothioate

Example 11

Different siRNA duplexes targeting ALDH2 and containing inverted RNA nucleotides at both 3'-ends were tested for serum stability. ALD02-ALD05 contain inverted RNA in addition to the last nucleotide in first and second strand. ALD06-ALD09 contain inverted RNA instead of the last nucleotide in first and second strand. All inverted RNA nucleotides substitute for terminally used phosphorothioates. In both designs, ivA and ivG confer higher stability to the tested sequence than ivU and ivC.

Figure 14:
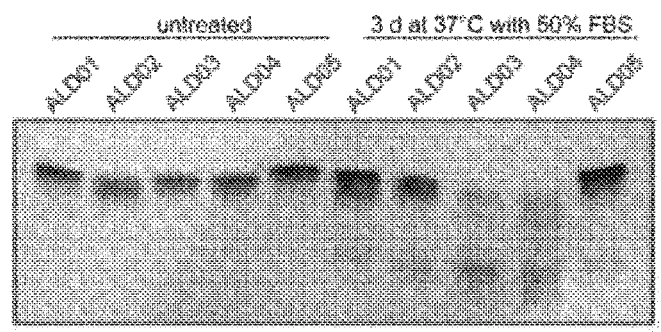
FIG. 14 shows the serum stability of different siRNA duplexes targeting ALDH2 and containing inverted RNA nucleotides at both 3'-ends.

"UT" indicates untreated samples. "FBS" indicates siRNA duplexes which were incubated at 5 µM concentration with 50% FBS for 3 d, phenol/chloroform-extracted and precipitated with Ethanol. Samples were analysed on 20% TBE polyacrylamide gels in native gel electrophoresis and results are shown in FIG. 14.

Sequences are shown in Table 3.

TABLE 3

Different siRNA duplexes
containing inverted RNA nucleotides at
both 3'-ends, where each sequence targets ALDH2.

| Duplex ID | sequence and chemistry<br>top: first strand,<br>bottom: second strand, both 5'-3' |
|---|---|
| ALD01 | mA(ps)fA(ps)mUfGmUfUmUfUmCfCmUfGmCfUmGfAmC<br>(ps)fG(ps)mG<br>fC(ps)mC(ps)fGmUfCmAfGmCfAmGfGmAfAmAfAmCfA<br>(ps)mU(ps)fU |
| ALD02 | mA(ps)fA(ps)mUfGmUfUmUfUmCfCmUfGmCfUmGfAmC<br>fGmG ivA<br>fC(ps)mC(ps)fGmUfCmAfGmCfAmGfGmAfAmAfAmCfA<br>mUfU ivA |
| ALD03 | mA(ps)fA(ps)mUfGmUfUmUfUmCfCmUfGmCfUmGfAmC<br>fGmG ivU<br>fC(ps)mC(ps)fGmUfCmAfGmCfAmGfGmAfAmAfAmCfA<br>mUfU ivU |
| ALD04 | mA(ps)fA(ps)mUfGmUfUmUfUmCfCmUfGmCfUmGfAmC<br>fGmG ivC<br>fC(ps)mC(ps)fGmUfCmAfGmCfAmGfGmAfAmAfAmCfA<br>mUfU ivC |
| ALD05 | mA(ps)fA(ps)mUfGmUfUmUfUmCfCmUfGmCfUmGfAmC<br>fGmG ivG<br>fC(ps)mC(ps)fGmUfCmAfGmCfAmGfGmAfAmAfAmCfA<br>mUfU ivG |
| ALD06 | mA(ps)fA(ps)mUfGmUfUmUfUmCfCmUfGmCfUmGfAmC<br>fG ivA<br>fC(ps)mC(ps)fGmUfCmAfGmCfAmGfGmAfAmAfAmCfA<br>mU ivA |
| ALD07 | mA(ps)fA(ps)mUfGmUfUmUfUmCfCmUfGmCfUmGfAmC<br>fG ivU<br>fC(ps)mC(ps)fGmUfCmAfGmCfAmGfGmAfAmAfAmCfA<br>mU ivU |
| ALD08 | mA(ps)fA(ps)mUfGmUfUmUfUmCfCmUfGmCfUmGfAmC<br>fG ivC<br>fC(ps)mC(ps)fGmUfCmAfGmCfAmGfGmAfAmAfAmCfA<br>mU ivC |
| ALD09 | mA(ps)fA(ps)mUfGmUfUmUfUmCfCmUfGmCfUmGfAmC<br>fG ivG<br>fC(ps)mC(ps)fGmUfCmAfGmCfAmGfGmAfAmAfAmCfA<br>mU ivG |

Duplex ID (SEQ ID NO: top; bottom):
ALD01 (51; 52), ALD02 (53; 54), ALD03 (55; 56),
ALD04 (57; 58), ALD05 (59; 60), ALD06 (61; 62),
ALD07 (63; 64), ALD08 (65; 66), ALD09 (67; 68).
mA, mU, mC, mG-2'OMe RNA
fA, fU, fC, fG-2'-F RNA
ivA, ivU, ivC, ivG-inverted RNA (3'-3')
(ps)-phosphorothioate

Example 12

The influence of inverted A, U, C and G RNA nucleotides at 3'-overhang positions was analysed using an siRNA against ALDH2. Sequences are set out in Table 3. ALD01 contains phosphorothioates at all termini, whereas ALD02-ALD05 contain ivA (ALD01), ivU (ALD03), ivC (ALD04) and ivG (ALD05) at the 3'-end of the first strand and at the 3'-end of the second strand. Both inverted nucleotides are present in addition to the terminal nucleotide of the respective strands and substitute for terminal phosphorothioates. A non-related siRNA (PTEN) and a non-targeting siRNA (Luci) were included as controls. All tested variants show comparable activity under the tested conditions.

Figure 15:
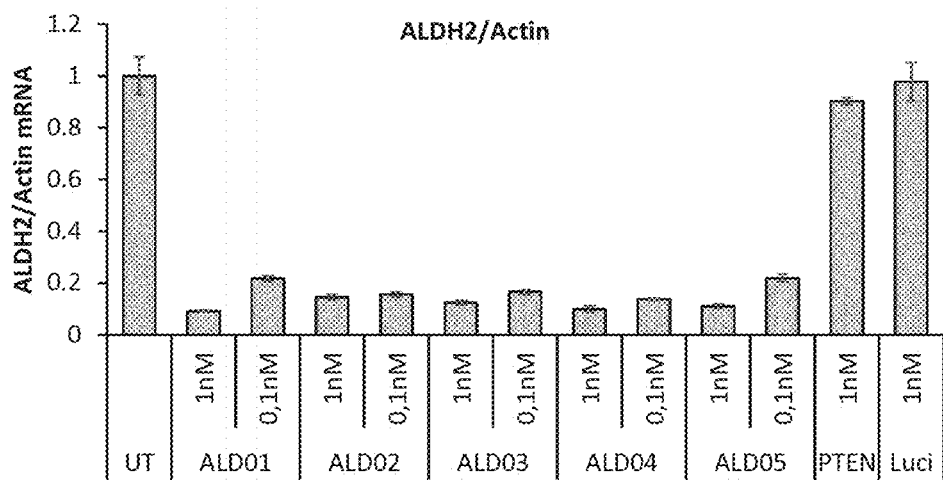
FIG. 15 shows the in vitro activity of siRNAs targeting ALDH2 with inverted A, U, C and G RNA nucleotides at 3'-overhang positions.

The experiment was conducted in Hep3B. Cells were seeded at a density of 150,000 cells per 6-well, transfected with 0.1 nM and 1 nM siRNA and 1 µg/ml Atufect after 24 h and lysed after 48 h. Total RNA was extracted and ALDH2 and Actin mRNA levels were determined by Taqman qRT-PCR. Results are shown in FIG. 15. Each bar represents mean±SD of three technical replicates.

Example 13

The influence of inverted A, U, C and G RNA nucleotides at terminal 3' positions was analysed using an siRNA against ALDH2. Sequences are set out in Table 3. ALD01 contains phosphorothioates at all termini, whereas ALD06-ALD09 contain ivA (ALD06), ivU (ALD07), ivC (ALD08) and ivG (ALD09) at the 3'-end of the first strand and at the 3'-end of the second strand. Both inverted nucleotides are present instead of the terminal nucleotide of the respective strands and substitute for terminal phosphorothioates. A non-related siRNA (PTEN) and a non-targeting siRNA (Luci) were included as controls. All tested variants show comparable activity under the tested conditions.

Figure 16:
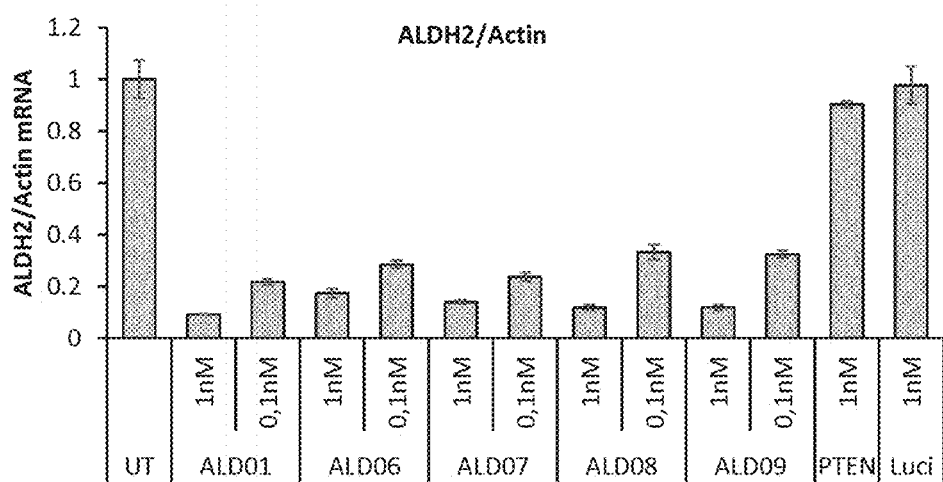
FIG. 16 shows the in vitro activity of siRNAs targeting ALDH2 with inverted A, U, C and G RNA nucleotides at terminal 3' positions.

The experiment was conducted in Hep3B. Cells were seeded at a density of 150,000 cells per 6-well, transfected with 0.1 nM and 1 nM siRNA and 1 µg/ml Atufect after 24 h and lysed after 48 h. Total RNA was extracted and ALDH2 and Actin mRNA levels were determined by Taqman qRT-PCR. Results are shown in FIG. 16. Each bar represents mean±SD of three technical replicates.

Example 14

Different GalNAc-siRNA conjugates containing inverted RNA nucleotides were tested for serum stability. STS22002L6 contains phosphorothioates at all non-conjugated ends, whereas STS22002V1 L6 and STS22002V2L6 contain inverted RNA nucleotides at the second strand 3'-end, where the nucleotide is present instead of the last nucleotide. STS22002V3L6 and -V4L6 contain inverted RNA nucleotides at the first strand 3'-end, where the nucleotide is present in addition to the last nucleotide. ivA was used in STS22002V1 L6 and -V3L6, whereas ivG was used in STS22002V2L6 and -V4L6. All inverted RNA nucleotides substitute for terminally used phosphorothioates. STS22002V1 L6 and -V2L6 are slightly more stable than the other variants tested here.

Figure 17:
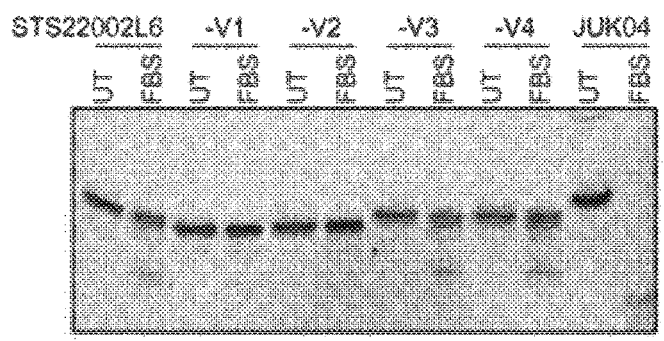
FIG. 17 shows the serum stability of different GalNAc-siRNA conjugates targeting ALDH2 and containing inverted RNA nucleotides.

"UT" indicates untreated samples. "FBS" indicates GalNAc-siRNA conjugates which were incubated at 5 µM concentration with 50% FBS for 3 d, phenol/chloroform-extracted and precipitated with Ethanol. Samples were analysed on 20% TBE polyacrylamide gels in native gel electrophoresis and results are shown in FIG. 17.

Sequences are set out in Table 4.

TABLE 4

Different GalNAc-siRNA conjugates of a ALDH2 targeting sequence, containing inverted RNA nucleotides.

| Duplex ID | sequence chemistry top: first strand, bottom: second strand, both 5'-3' |
|---|---|
| STS22002L6 | mA(ps)fA(ps)mUfGmUfUmUfmCfCmUfGmCfUmGf AmC(ps)fG(ps)mG [ST23(ps)]3 ST43(ps)fCmCfGmUfCmAfGmCfA mGfGmAfAmAfAmCfA(ps)mU(ps)fU |
| STS22002V1L6 | mA(ps)fA(ps)mUfGmUfUmUfmCfCmUfGmCfUmGf AmC(ps)fG(ps)mG [ST23(ps)]3 ST43(ps)fCmCfGmUfCmAfGmCfA mGfGmAfAmAfAmCfAmUfU ivA |

TABLE 4-continued

Different GalNAc-siRNA conjugates of a ALDH2 targeting sequence, containing inverted RNA nucleotides.

| Duplex ID | sequence chemistry top: first strand, bottom: second strand, both 5'-3' |
|---|---|
| STS22002V2L6 | mA(ps)fA(ps)mUfGmUfUmUfmCfCmUfGmCfUmGf AmC(ps)fG(ps)mG [ST23(ps)]3 ST43(ps)fCmCfGmUfCmAfGmCfA mGfGmAfAmAfAmCfAmUfU ivG |
| STS22002V3L6 | mA(ps)fA(ps)mUfGmUfUmUfmCfCmUfGmCfUmGf AmCfGmG ivA [ST23(ps)]3 ST43(ps)fCmCfGmUfCmAfGmCfA mGfGmAfAmAfAmCfA(ps)mU(ps)fU |
| STS22002V4L6 | mA(ps)fA(ps)mUfGmUfUmUfmCfCmUfGmCfUmGf AmCfGmG ivG [ST23(ps)]3 ST43(ps)fCmCfGmUfCmAfGmCfA mGfGmAfAmAfAmCfA(ps)mU(ps)fU |

Duplex ID (SEQ ID NO: top; bottom):
STS22002L6 (199; 70), STS22002V1L6 (200; 72),
STS2200V2L6 (201; 74), STS22002V3L6 (202; 76),
STS22002V4L6 (203; 78).
mA, mU, mC, mG-2'OMe RNA
fA, fU, fC, fG-2'F RNA
ivA, ivG-inverted RNA (3'-3')
(ps)-phosphorothioate Example 14

The influence of inverted RNA nucleotides at terminal 3' positions was analysed using a GalNAc-siRNA conjugate targeting ALDH2 by receptor-mediated uptake in mouse primary hepatocytes. The sequences are set out in Table 4. STS22002L6 contains phosphorothioates at all non-conjugated ends, whereas STS22002V1 L6 and STS22002V2L6 contain inverted RNA nucleotides at the second strand 3'-end, where the nucleotide is present instead of the last nucleotide. STS22002V3L6 and -V4L6 contain inverted RNA nucleotides at the first strand 3'-end, where the nucleotide is present in addition to the last nucleotide. ivA was used in STS22002V1 L6 and -V3L6, whereas ivG was used in STS22002V2L6 and -V4L6. All inverted RNA nucleotides substitute for terminally used phosphorothioates. All tested variants show comparable activity.

Figure 18:
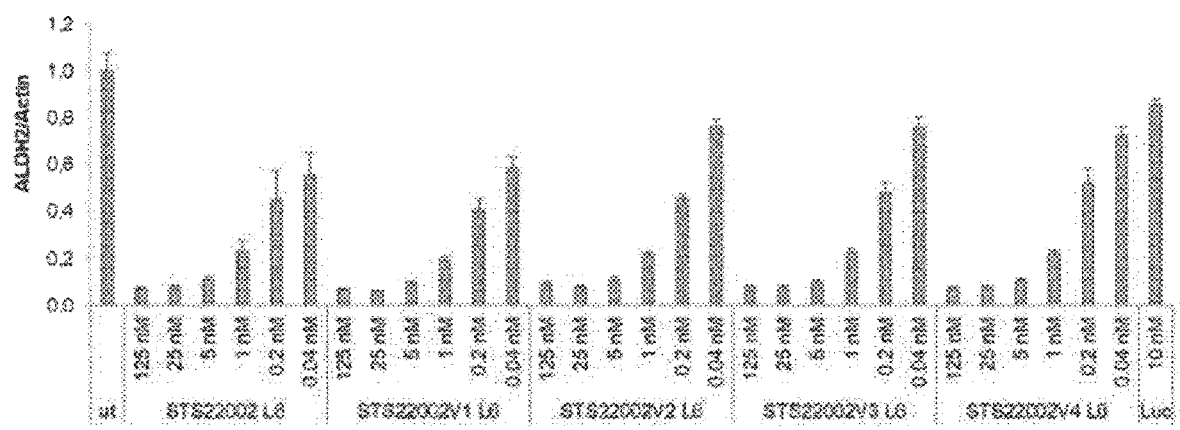
FIG. 18 shows the in vitro activity of GalNAc-conjugated siRNAs targeting ALDH2 with inverted RNA nucleotides at terminal 3' positions after receptor-mediated uptake in mouse primary hepatocytes.

The experiment was conducted in primary mouse hepatocytes. Cells were seeded at a density of 20,000 cells per 96-well, treated with 125 nM to 0.04 nM siRNA conjugate directly after plating and lysed after 24 h. Total RNA was extracted and ALDH2 and Actin mRNA levels were determined by Taqman qRT-PCR. Results are shown in FIG. 18. Each bar represents mean±SD of three technical replicates.

Example 15

The influence of ivA at the first strand 3'-end was analysed in vivo in mice. Therefore, GalNAc-siRNA conjugates targeting ALDH2 were used. Sequences are set out in Table 4. STS22002L6 contains phosphorothioates at all non-conjugated termini, whereas STS22002V3L6 contains ivA at the first strand 3'-end in addition to the last nucleotide.

C57BL/6 male mice were subcutaneously treated with 10 mg/kg and 3 mg/kg GalNAc conjugate. Liver sections were prepared 7 days after treatment, RNA was extracted from the tissue and ALDH2 and ApoB mRNA levels were analysed by Taqman qRT-PCR. Results are shown in FIG. 19. Each bar represents mean±SD of six animals.

Example 16

In Vitro Activity of GalNAc-Conjugated siRNAs Against ALDH2 (STS22006) Containing Inverted RNA Nucleotides in Addition to Terminal Nucleotides.

The influence of inverted RNA nucleotides at terminal positions was analyzed using GalNAc-siRNA conjugates targeting ALDH2 after receptor-mediated uptake in mouse primary hepatocytes. STS22006L6 contains phosphorothioates at all non-conjugated ends, whereas STS22006V7L6 contains one ivA at the first strand 3'-end and STS22006V8L6 contains one ivA at the second strand 3'-end. STS22006V9L6 contains each one ivA at the first strand and second strand 3'-ends. The named conjugates contain a GalNAc moiety at the second strand 5'-end. STS22006V10L35 contains a GalNAc moiety at the first strand 3'-end with each one ivA at the second strand 5'- and 3'-ends. All siRNA conjugates described here contain ivA instead of the terminal nucleotide and instead of terminal phosphorothioates.

The experiment was conducted in primary mouse hepatocytes. Cells were seeded at a density of 20,000 cells per 96-well, treated with 100, 10 and 1 nM siRNA conjugate directly after plating and lysed after 24 h. Total RNA was extracted and ALDH2 and PTEN mRNA levels were determined by Taqman qRT-PCR. Each bar represents mean±SD of three technical replicates Data is shown in FIGS. 20 and 21

Example 17

In Vitro Activity of GalNAc-Conjugated siRNAs Against ALDH2 (STS22009) Containing Inverted RNA Nucleotides in Addition to Terminal Nucleotides.

The influence of inverted RNA nucleotides at terminal positions was analyzed using GalNAc-siRNA conjugates targeting ALDH2 after receptor-mediated uptake in mouse primary hepatocytes. STS22009L6 contains phosphorothioates at all non-conjugated ends, whereas STS22009V3L6 contains one ivA at the first strand 3'-end and STS22009V4L6 contains one ivA at the second strand 3'-end. STS22009V5L6 contains each one ivA at the first strand and second strand 3'-ends. The named conjugates contain a GalNAc moiety at the second strand 5'-end. STS22009V6L35 contains a GalNAc moiety at the first strand 3'-end with each one ivA at the second strand 5'- and 3'-ends. All siRNA conjugates described here contain ivA instead of the terminal nucleotide and instead of terminal phosphorothioates.

The experiment was conducted in primary mouse hepatocytes. Cells were seeded at a density of 20,000 cells per 96-well, treated with 100, 10 and 1 nM siRNA conjugate directly after plating and lysed after 24 h. Total RNA was extracted and ALDH2 and PTEN mRNA levels were determined by Taqman qRT-PCR. Each bar represents mean±SD of three technical replicates Data is shown in FIGS. 22 and 23

Example 18

In Vitro Activity of GalNAc-Conjugated siRNAs Against TTR Containing Inverted RNA Nucleotides in Addition to Terminal Nucleotides.

The influence of inverted RNA nucleotides at terminal positions was analyzed using GalNAc-siRNA conjugates targeting TTR after receptor-mediated uptake in mouse primary hepatocytes. STS16001 L1 contains phosphorothioates at all non-conjugated ends, whereas STS16001V11 L1 contains one ivA at the first strand 3'-end and STS16001V12L1 contains one ivA at the second strand 3'-end. STS16001V13L1 contains each one ivA at the first strand and second strand 3'-ends. The named conjugates contain a GalNAc moiety at the second strand 5'-end. STS16001V14L35 contains a GalNAc moiety at the first strand 3'-end with each one ivA at the second strand 5'- and 3'-ends. All siRNA conjugates described here contain ivA instead of the terminal nucleotide and instead of terminal phosphorothioates.

The experiment was conducted in primary mouse hepatocytes. Cells were seeded at a density of 20,000 cells per 96-well, treated with 10, 1 and 0.1 nM siRNA conjugate directly after plating and lysed after 24 h. Total RNA was extracted and TTR and PTEN mRNA levels were determined by Taqman qRT-PCR. Each bar represents mean±SD of three technical replicates.

Data is shown in FIGS. 24 and 25

Example 19

In Vitro Activity of GalNAc-Conjugated siRNAs Against ALDH2 Containing Inverted RNA Nucleotides at 3'-Ends Instead of the Last Nucleotide.

The influence of inverted RNA nucleotides at terminal 3' positions was analyzed using GalNAc-siRNA conjugates targeting ALDH2 after receptor-mediated uptake in mouse primary hepatocytes. STS22002L6 contains phosphorohioates at all non-conjugated ends, whereas STS22002V8L6 contains one ivA at the first strand 3'-end instead of the last nucleotide and instead of phosphorothioates. STS22002V9L6 contains each one ivA at the first and second strand 3'-ends instead of the respective last nucleotides and terminal phosphorothioates. STS22002V10L6 contains one ivA at the first strand 3'-end in addition to the last nucleotide and one ivA at the second strand 3'-end instead of the last nucleotide. Both ivA-containing ends are not stabilized by terminal phosphorothioates and the siRNA is conjugated to a GalNAc moiety which does not contain phosphorothioates.

The experiment was conducted in primary mouse hepatocytes. Cells were seeded at a density of 20,000 cells per 96-well, treated with 100, 10 and 1 nM siRNA conjugate directly after plating and lysed after 24 h. Total RNA was extracted and ALDH2 and PTEN mRNA levels were determined by Taqman qRT-PCR. Each bar represents mean±SD of three technical replicates.

Data is shown in FIGS. 26 and 27

Example 20

Different modified variants of the GalNAc-siRNA conjugates STS22006 and STS22009 were analyzed for knockdown activity in vivo. "V1" variants contain a different 2'-OMe/2'-F modification pattern in the second strand and an ivA nucleotide at the 3'-end of the second strand, substituting for the last nucleotide and for terminal phosphorothioates at this end. "V2" additionally contains a different 2'-OMe/2'-F modification pattern in the first strand.

C57BL/6 male mice were subcutaneously treated with 3 mg/kg and 1 mg/kg GalNAc conjugate. Liver sections were prepared 9 days after treatment, RNA was extracted from the tissue and ALDH2 and ApoB mRNA levels were analyzed by Taqman qRT-PCR. Each bar represents mean±SD of six animals. Statistical analysis is based on Kruskal-Wallis test with Dunn's multiple comparisons test against control group (PBS).

Data is shown in FIGS. 28 and 29.

Example 21

Serum stability of siRNA-conjugates (X0258-261) with non-cleavable GalNAc linker at the 5'-end of the second strand and 3' phosphorylated ivR substituting the first nucleotide at the 5'-end of the first strand in comparison to stable X0139 and less stabilized positive (Juk) control for nuclease degradation.

The siRNA conjugates were incubated for 4 hours (4h) or 3 days (3d) in 50% FBS at 37° C. or left untreated (0h). After incubation, RNA was extracted by phenol/chloroform/isoamyl alcohol extraction. Degradation was visualized by TBE-Polyacrylamid gel electrophoresis and staining of RNA with SYBRGold.

Figure 31:
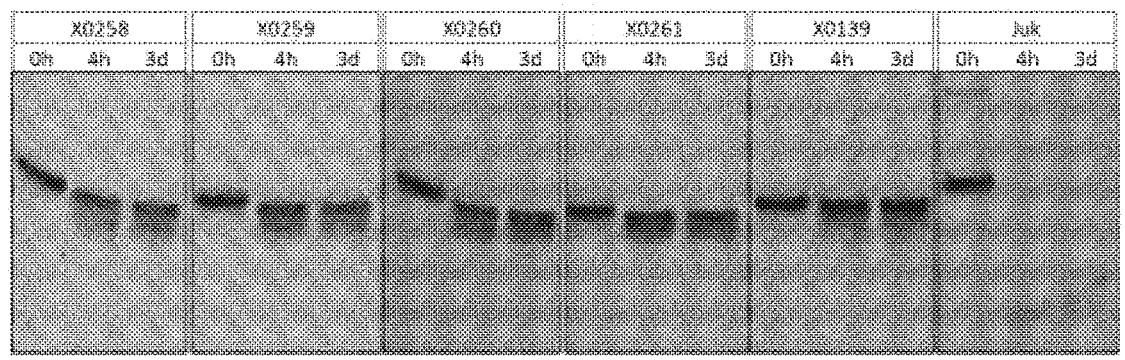
FIG. 31 shows serum stability of siRNAs containing 5'-5'-linked ribonucleotides at the 5'-end of the first strand.

Data are shown in FIGS. 30 and 31.

Example 22

Target gene expression in primary murine hepatocytes 24 h following treatment with TTR-siRNA conjugates with non-cleavable GalNAc-cluster at the 5'-end of the second strand and with one 3'-phosphorylated inverted ribonucleotide at the 5'-position of the first strand, without stabilizing phosphorothioate linkages between the three terminal nucleotides at that end (X0258-261), in comparison to a non-targeting GalNAc-siRNA (Luc), and a positive control (X0139) at indicated concentrations or cells left untreated (UT).

The experiment was conducted in murine primary hepatocytes. Cells were seeded at a density of 30,000 cells per 96-well and treated with siRNA-conjugates at concentrations ranging from 10 nM to 0.0001 nM. 24 h post treatment cells were lysed and RNA was extracted. Transcript levels of TTR and housekeeping mRNA (PTEN) were quantified by TaqMan analysis. Each bar represents mean±SD of three technical replicates.

Figure 32:
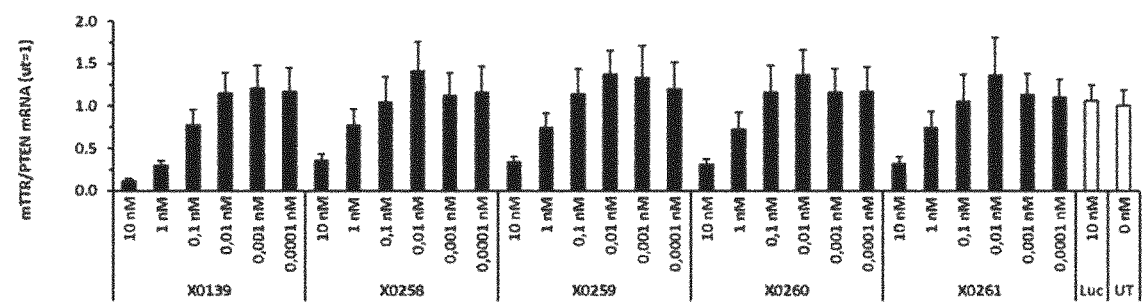
FIG. 32 shows in vitro activity of siRNAs with 5'-5'-linked ribonucleotides at the 5'-end of the first strand.

Data are shown in FIGS. 30 and 32.

Example 23

Target gene expression in primary murine hepatocytes 24 h following treatment with TTR-siRNA with a GalNAc-cluster at the 3'-end of the first strand and one inverted ribonucleotide as an overhang at the 5'-position of the second strand replacing the two stabilizing phosphorothioate linkages between the first three nucleotides at this end (X0264-267), in comparison to a non-targeting GalNAc-siRNA (Luc), and a positive control (X0107) at indicated concentrations or left untreated (UT).

The experiment was conducted in murine primary hepatocytes. Cells were seeded at a density of 30,000 cells per 96-well and treated with siRNA-conjugates at concentrations ranging from 10 nM to 0.001 nM. 24 h post treatment cells were lysed and RNA was extracted. Transcripts levels of TTR and housekeeping mRNA (PTEN) were quantified by TaqMan analysis. Each bar represents mean±SD of three technical replicates.

Figure 33:
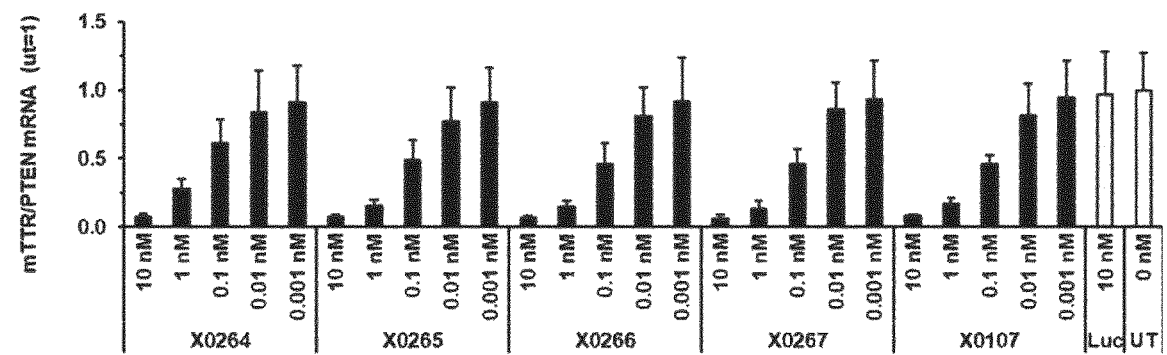
FIG. 33 shows in vitro activity of siRNAs with 5'-5'-linked ribonucleotides at the 5'-end of the second strand.

Data are shown in FIGS. 30 and 33.

Example 24

Additional example compounds were synthesised by the methods described below and methods known to the person skilled in the art. Assembly of the oligonucleotide chain and linker building blocks was performed by solid phase synthesis applying phosphoramidte methodology. GalNAc conjugation was achieved by peptide bond formation of a GalNAc-carboxylic acid building block to the prior assembled and purified oligonucleotide having the necessary number of amino modified linker building blocks attached.

Oligonucleotide synthesis, deprotection and purification followed standard procedures that are known in the art.

Oligonucleotides were synthesized on an AKTA oligopilot synthesizer using standard phosphoramidite chemistry. Commercially available solid support and 2'O-Methyl RNA phosphoramidites, 2'Fluoro, 2'Deoxy RNA phosphoramidites, 2'TBDMS RNA phosphoramidites (all standard protection, ChemGenes, LinkTech) and commercially available long trebler phosphoramidite (Glen research) and 3'-Amino Modifier TFA Amino C-6 Icaa CPG 500 Å (CPG supported GlyC3Am(TFA)) was purchased from ChemGenes. Per-acetylated galactose amine 8 is commercially available. Phosphate generating agent Bis-cyanoethyl-N,N-diisopropyl phosphoramidite was purchased from ChemGenes.

Ancillary reagents were purchased from EMP Biotech. Synthesis was performed using a 0.1 M solution of the phosphoramidite in dry acetonitrile and benzylthiotetrazole (BTT) was used as activator (0.3M in acetonitrile). Coupling time was 15 min. A Cap/OX/Cap or Cap/Thio/Cap cycle was applied (Cap: Ac2O/NMI/Lutidine/Acetonitrile, Oxidizer: 0.1 M I2 in pyridine/H2O). Phosphorothioates were introduced using standard commercially available thiolation reagent (EDITH, Link technologies). DMT cleavage was achieved by treatment with 3% dichloroacetic acid in toluene. Upon completion of the programmed synthesis cycles a diethylamine (DEA) wash was performed. All oligonucleotides were synthesized in DMT-off mode.

GlyC3Am(TFA)-solid support is:

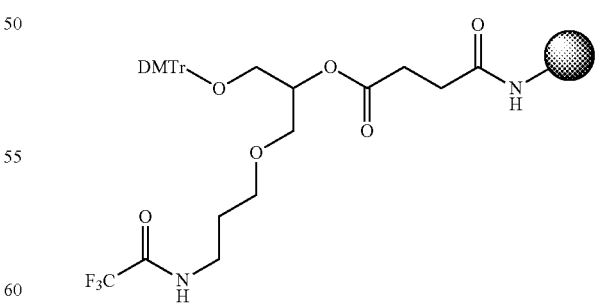

Synthesis of Compounds 2 to 10 and ST13

Compounds 2 to 5 and (S)-DMT-Serinol(TFA)-phosphoramidite 7 were synthesised according to literature published methods (Hoevelmann et al. Chem. Sci., 2016, 7, 128-135).

Scheme 1
Synthesis of (S)-DMT-serinol (TFA) linker synthons

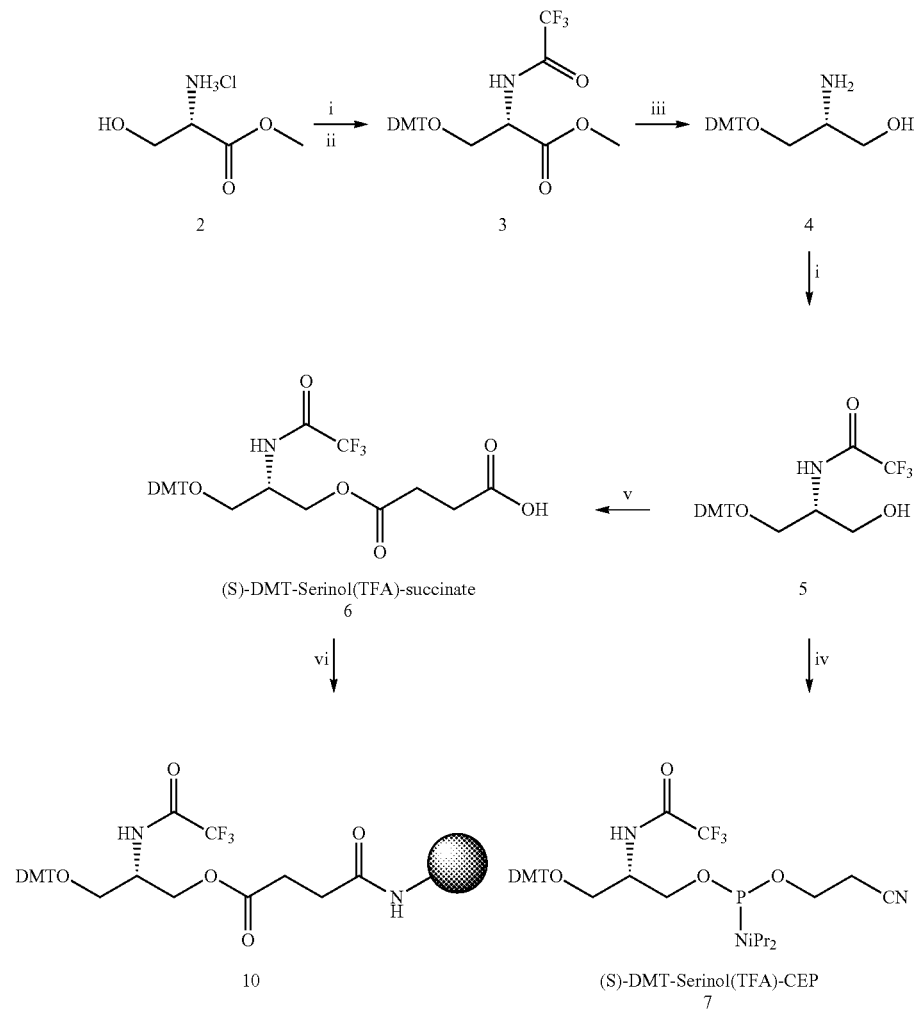

i) ethyl trifluoroacetate, NEt3, MeOH, 0° C., 16h, 5: 90%, ii) DMTCl, pyridine, 0° C., 16h, 64% over two steps, iii) LiBH4, EtOH/THF (1/1, v/v), 0° C., 1h, 76%, iv) 2-cyanoethyl-N,N-diisopropylchloro phosphoramidite, EtNiPr2, CH2Cl2, 56%, v) succinic anhydride, DMAP, pyridine, RT, 16h, 38%, vi) HBTU, DIEA, amino-Icaa CPG (500A), RT, 18h, 29% (26 μmol/g loading).

(S)-4-(3-(bis(4-methoxyphenyl)(phenyl)methoxy)-2-(2,2,2-trifluoroacetamido)propoxy)-4-oxobutanoic acid (6)

To a solution of 5 in pyridine was added succinic anhydride, followed by DMAP. The resulting mixture was stirred at room temperature overnight. All starting material was consumed, as judged by TLC. The reaction was concentrated. The crude material was chromatographed in silica gel using a gradient 0% to 5% methanol in DCM (+1% triethylamine) to afford 1.33 g of 6 (yield=38%). m/z (ESI−): 588.2 (100%), (calcd. for C30H29F3NO8− [M−H]− 588.6). 1H-NMR: (400 MHz, CDCl3) δ [ppm]=7.94 (d, 1H, NH), 7.39-7.36 (m, 2H, CHaryl), 7.29-7.25 (m, 7H, CHaryl), 6.82-6.79 (m, 4H, CHaryl), 4.51-4.47 (m, 1H), 4.31-4.24 (m, 2H), 3.77 (s, 6H, 2×DMTr-OMe), 3.66-3.60 (m, 16H, HNEt3+), 3.26-3.25 (m, 2H), 2.97-2.81 (m, 20H, NEt3), 2.50-2.41 (4H, m), 1.48-1.45 (m, 26H, HNEt3+), 1.24-1.18 (m, 29H, NEt3).

(S)-DMT-Serinol(TFA)-succinate-Icaa-CPG (10)

The (S)-DMT-Serinol(TFA)-succinate (159 mg, 270 umol) and HBTU (113 mg, 299 umol) were dissolved in CH3CN (10 mL). Diisopropylethylamine (DIPEA, 94 μL, 540 umol) was added to the solution, and the mixture was swirled for 2 min followed by addition native amino-Icaa-CPG (500 A, 3 g, amine content: 136 umol/g). The suspension was gently shaken at room temperature on a wrist-action shaker for 16h then filtered, and washed with DCM and EtOH. The solid support was dried under vacuum for 2 h. The unreacted amines on the support were capped by stirring with acetic anhydride/lutidine/N-methylimidazole at room temperature. The washing of the support was repeated as above. The solid was dried under vacuum to yield solid support 10 (3 g, 26 umol/g loading).

Synthesis of GalNAc synthon 9 was performed as described in Nair et al. J. Am. Chem. Soc., 2014, 136 (49), pp 16958-16961.

Scheme 2
Synthesis of GalNAc synthon 9

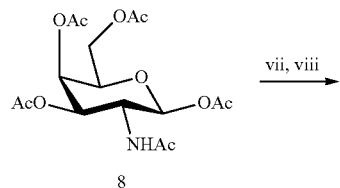

8

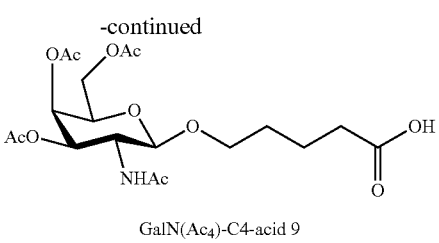

GalN(Ac₄)-C4-acid 9

(vii) TMSOTf, DCM, hexenol, viii) RuCl3, NaIO4, DCM, CH3CN, H2O, 46% over two steps.

Synthesis of ST13(Ac)9 was achieved by following methods as described in Nair et al. J. Am. Chem. Soc., 2014, 136 (49), pp 16958-16961. Final deacetylation to yield ST13 was achieved by treating ST13(Ac)9 with sodium methoxide in methanol.

Scheme 3
Syntheses of ST13 synthon

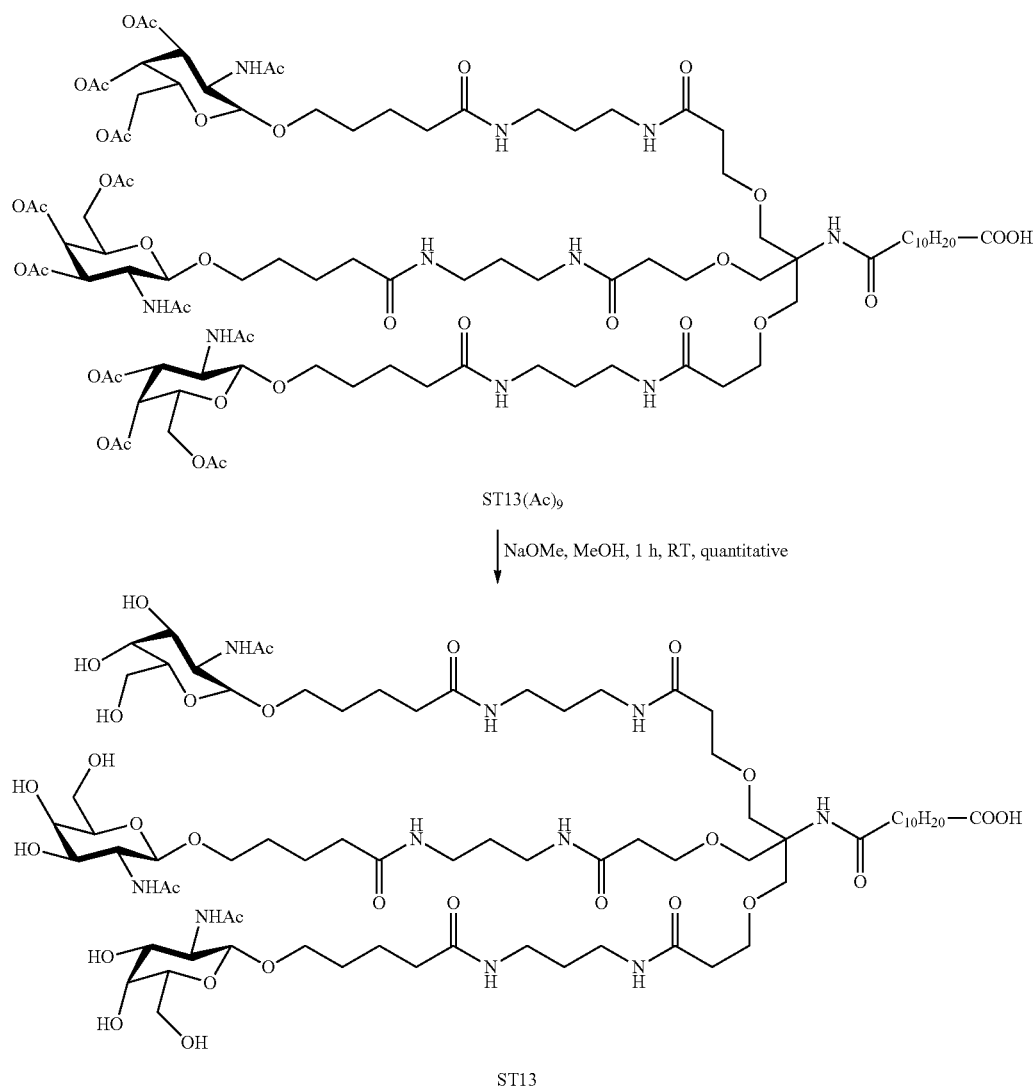

Trimeric GalNAc Synthon (ST13).

ST13(Ac)9 (3150 mg, 1.570 mmol) was dissolved in Methanol (100 ml) and sodium methoxide (5.4M, 227 mg, 1.512 mmol, 280 μL) was added (via syringe) at room temperature. The resulting mixture was stirred at for 1 h. Acetonitrile was added (75 ml) and the reaction mixture was concentrated under reduced pressure. m/z (ESI+): 814.5 (100%), (calcd. for C73H131 N10O302+ [M+2H]2+ 814.5). 1H NMR (400 MHz, DMSO-d6) δ[ppm]=7.91-7.72 (m, 9H, NH), 7.08 (s, 1H, NH), 4.90 (d, 3H), 4.77 (m, 3H), 4.20 (d; 3H), 3.70-3.64 (m, 9H), 3.57-3.40 (br, 30H, incl. res. H2O), 3.26 (m, 6H), 3.03-3.01 (m, 12H), 2.27-2.25 (m, 6H), 2.07-2.03 (m, 10H), 1.89-1.85 (t, 2H), 1.78 (s, 9H), 1.52-1.41 (m, 22H); 1.21 (m, 12H).

Synthesis of Oligonucleotides

Oligonucleotide synthesis of 3'trivalent tree-like GalNAc-cluster conjugated oligonucleotides commenced using commercially available GlyC3Am-solid support as in the example compound 168. Phosphoramidite synthesis coupling cycle consisting of 1) DMT-removal, 2) chain elongation using the required DMT-masked phosphoramidite, 3) capping of non-elongated oligonucleotide chains, followed by oxidation of the P(III) to P(V) either by Iodine or EDITH (if phosphorothioate linkage was desired) and again capping (Cap/Ox/Cap or Cap/Thio/Cap) was repeated until full length of the product was reached. Upon completion of chain elongation, the protective DMT group of the last coupled amidite building block was removed, as in step 1) of the phosphoramidite synthesis cycle.

Oligonucleotide synthesis of multiple 3' mono-GalNAc conjugated oligonucleotides was commenced using (S)-DMT-Serinol(TFA)-succinate-Icaa-CPG (10) as in example compound 87. A second and third (S)-DMT-serinol(TFA) was coupled in the first and second cycle to the serinol (TFA)-CPG in order to make the precursor compound 11 for the example compound 87. Afterwards, phosphoramidite synthesis cycle was applied using 5'-DMT-2'OMe-RNA or 5'-DMT-2'F-DNA phosphoramidites until full length of the product was reached. Upon completion of chain elongation, the protective DMT group of the last coupled amidite building block was removed, as in step 1) of the phosphoramidite synthesis cycle.

Scheme 4
Synthesis of serinol-derived precursor oligonucleotides

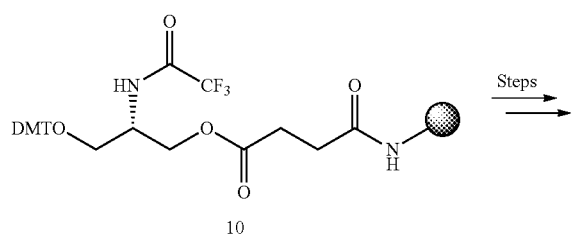

10

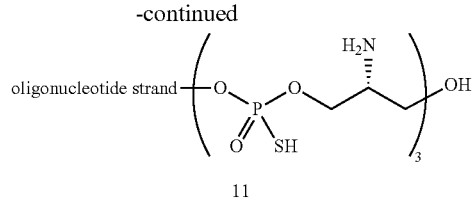

11

Finally, the respective oligonucleotides were off the CPG and set free from additional protective groups by by 40% aq. methylamine treatment. This treatment also liberated the amino function in the Serinol(TFA) and GlyC3Am(TFA) building block. The crude products were then purified each by ion exchange chromatography (Resource Q, 6 mL, GE Healthcare) on an AKTA Pure HPLC System using a sodium chloride gradient. Product containing fractions were pooled, desalted on a size exclusion column (Zetadex, EMP Biotech) and lyophilized to yield the precursor oligonucleotides 1 or 11 for further GalNAc conjugation.

All final single stranded products were analysed by AEX-HPLC to prove their purity. Identity of the respective single stranded products (non-modified, amino-modified precursors or GalNAc conjugated oligonucleotides) was proved by LC-MS analysis.

Conjugation to Single Stranded Oligonucleotides

Conjugated Singles Strands SEQ ID 168, 180, 182, 184 and 186

Conjugation of the GalNac synthon (ST13) was achieved by coupling to the 3'-amino function of the respective oligonucleotide strand (1) using a peptide coupling reagent. Therefore, the respective amino-modified precursor molecule was dissolved in H2O (500 OD/mL) and DMSO (DMSO/H2O, 2/1, v/v) was added, followed by DIPEA (2.5% of total volume). In a separate reaction vessel pre-activation of the trimeric-GalNAc-synthon (ST13) was performed by reacting 2 eq. of the carboxylic acid component with 2 eq. of HBTU in presence of 8 eq. DIPEA in DMSO. After 2 min the pre-activated compound ST13 was added to the solution of the respective amino-modified precursor molecule 1. After 30 min the reaction progress was monitored by LCMS or AEX-HPLC. Upon completion of the conjugation reaction the crude product was precipitated by addition of 10×iPrOH and 0.1×2M NaCl and harvested by centrifugation and decantation. The resulting pellet was dissolved in H2O and finally purified again by anion exchange and size exclusion chromatography and lyophilised.

Scheme 5
Conjugation of ST13 to the 3' amino group

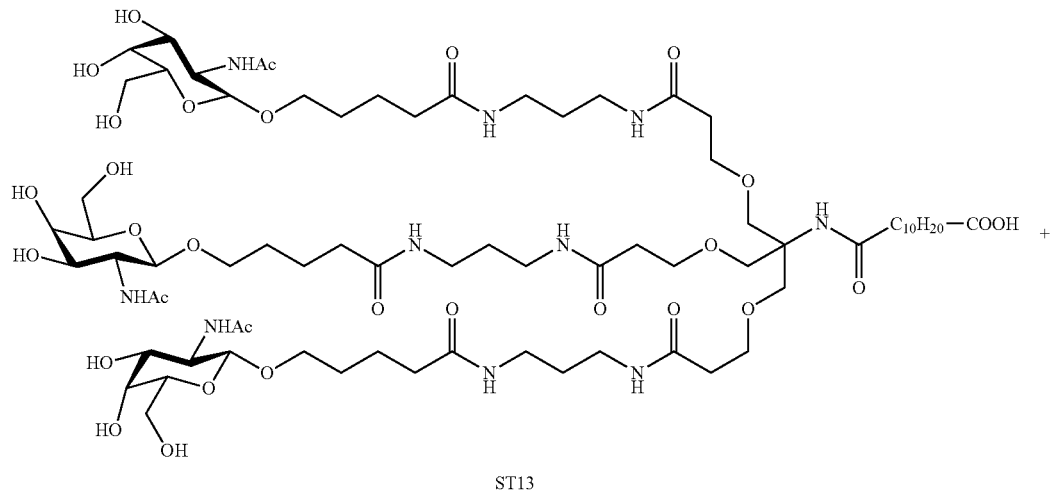

ST13

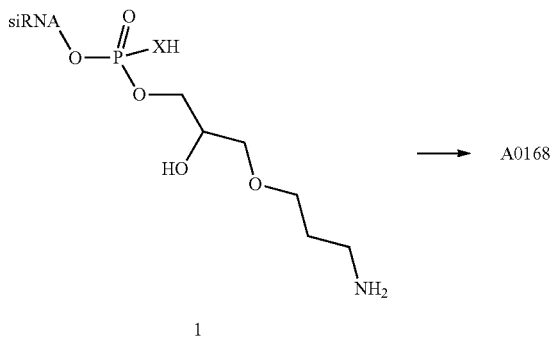

Conjugated Singles Strands 87, 107, 171, 173, 175, 177 and 179

Conjugation of the GalNac synthon (9) was achieved by coupling to the serinol-amino function of the respective oligonucleotide strand 11 using a peptide coupling reagent. Therefore, the respective amino-modified precursor molecule 11 was dissolved in H2O (500 OD/mL) and DMSO (DMSO/H2O, 2/1, v/v) was added, followed by DIPEA (2.5% of total volume). In a separate reaction vessel pre-activation of the GalN(Ac4)-C4-acid (9) was performed by reacting 2 eq. (per amino function in the amino-modified precursor oligonucleotide 11) of the carboxylic acid component with 2 eq. of HBTU in presence of 8 eq. DIPEA in DMSO. After 2 min the pre-activated compound 9 was added to the solution of the respective amino-modified precursor molecule. After 30 min the reaction progress was monitored by LCMS or AEX-HPLC. Upon completion of the conjugation reaction the crude product was precipitated by addition of 10× iPrOH and 0.1×2M NaCl and harvested by centrifugation and decantation. To set free the acetylated hydroxyl groups in the GalNAc moieties the resulting pellet was dissolved in 40% MeNH2 (1 mL per 500 OD) and after 15 min at RT diluted in H2O (1:10) and finally purified again by anion exchange and size exclusion chromatography and lyophilised to yield the final product 12.

Scheme 6
GalNAc conjugation to the 3' amino groups

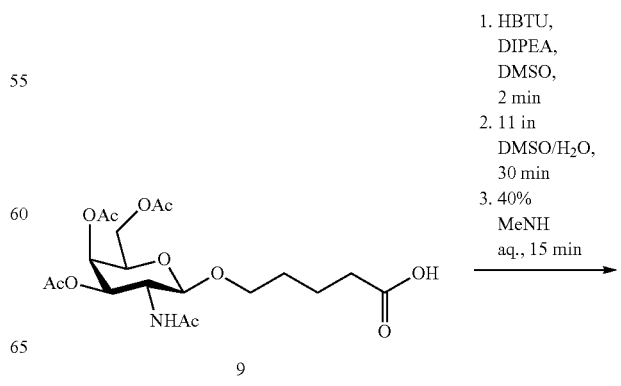

-continued

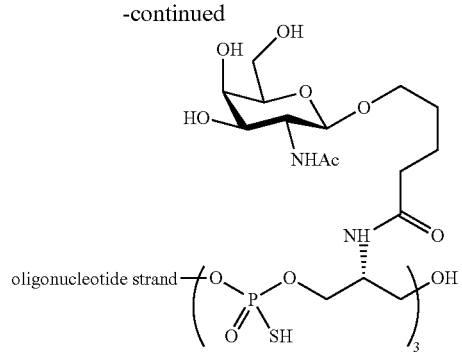

87

Ser(GN) Conjugated singles strands 87, 107, 171, 173, 175, 177 and 179 is a GalNAc-C4 building block attached to serinol derived linker moiety:

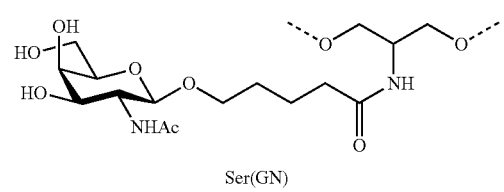

Ser(GN)

wherein the O— is the linkage between the oxygen atom and e.g. H, phosphoroate linkage or phosphorothioate linkage.

Serinol derived linker moieties may be based on serinol in any stereochemistry i.e. derived from L-serine isomer, D-serine isomer, a racemic serine or other combination of isomers. In a preferred aspect of the invention, the serinol-GalNAc moiety (SerGN) has the following stereochemistry:

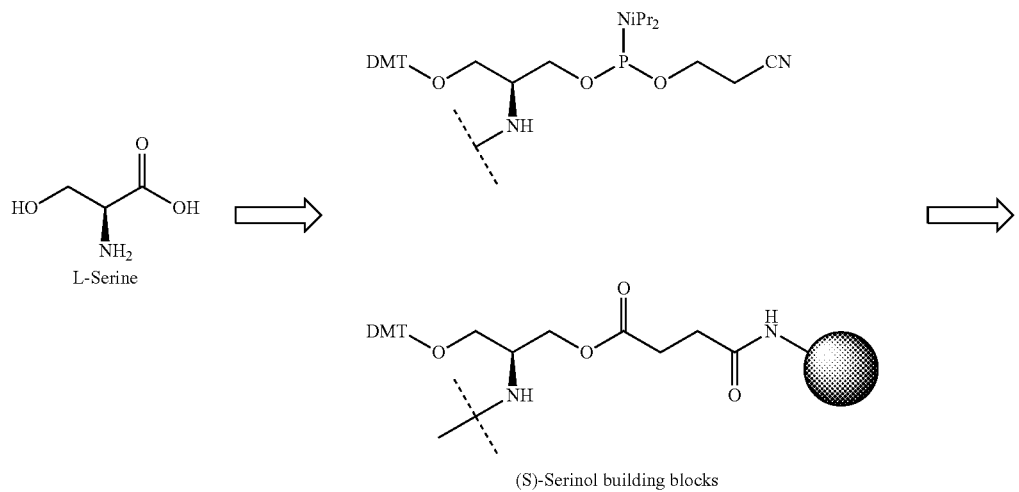

(S)-Serinol building blocks

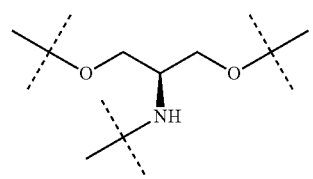

Serinol derived linker moieties i.e. is based on an (S)-serinol-amidite or (S)-serinol succinate solid supported building block derived from L-serine isomer.

Double Strand Formation

Individual single strands were dissolved in a concentration of 60 OD/mL in H2O. Both individual oligonucleotide solutions were added together in a reaction vessel. For easier reaction monitoring a titration was performed. The first strand was added in 25% excess over the second strand as determined by UV-absorption at 260 nm. The reaction mixture was heated to 80° C. for 5 min and then slowly cooled to RT. Double strand formation was monitored by ion pairing reverse phase HPLC. From the UV-area of the residual single strand the needed amount of the second strand was calculated and added to the reaction mixture. The reaction was heated to 80° C. again and slowly cooled to RT. This procedure was repeated until less than 10% of residual single strand was detected.

| SEQ ID | Name | Sequence (5'-3') |
|---|---|---|
| 1 | TMPJH01A | mAfAmCfCmAfGmAfAmGfAmAfGmCfAmGfGmUfGmA |
| 2 | TMPJH01B | fUmCfAmCfCmUfGmCfUmUfCmUfUmCfUmGfGmUfU |
| 3 | TMPJH40A | mA(ps)fA(ps)mCfCmAfGmAfAmGfAmAfGmCfAmGfGmU(ps)fG(ps)mA |
| 4 | TMPJH40B | fU(ps)mC(ps)fAmCfCmUfGmCfUmUfCmUfUmCfUmGfG(ps)mU(ps)fU |
| 5 | TMPJH41A | mA(ps)fA(ps)mCfCmAfGmAfAmGfAmAfGmCfAmGfGmU(ps)fG(ps)mA ivA |
| 6 | TMPJH41B | fU(ps)mC(ps)fAmCfCmUfGmCfUmUfCmUfUmCfUmGfG(ps)mU(ps)fU ivA |
| 7 | TMPJH42A | mA(ps)fA(ps)mCfCmAfGmAfAmGfAmAfGmCfAmGfGmU(ps)fG(ps)mA ivU |
| 8 | TMPJH42B | fU(ps)mC(ps)fAmCfCmUfGmCfUmUfCmUfUmCfUmGfG(ps)mU(ps)fU ivU |
| 9 | TMPJH43A | mA(ps)fA(ps)mCfCmAfGmAfAmGfAmAfGmCfAmGfGmU(ps)fG(ps)mA ivC |
| 10 | TMPJH43B | fU(ps)mC(ps)fAmCfCmUfGmCfUmUfCmUfUmCfUmGfG(ps)mU(ps)fU ivC |
| 11 | TMPJH44A | mA(ps)fA(ps)mCfCmAfGmAfAmGfAmAfGmCfAmGfGmU(ps)fG(ps)mA ivG |
| 12 | TMPJH44B | fU(ps)mC(ps)fAmCfCmUfGmCfUmUfCmUfUmCfUmGfG(ps)mU(ps)fU ivG |
| 13 | TMPJH45A | mA(ps)fA(ps)mCfCmAfGmAfAmGfAmAfGmCfAmGfGmUfGmA ivA |
| 14 | TMPJH45B | fU(ps)mC(ps)fAmCfCmUfGmCfUmUfCmUfUmCfUmGfGmUfU ivA |
| 15 | TMPJH46A | mA(ps)fA(ps)mCfCmAfGmAfAmGfAmAfGmCfAmGfGmUfGmA ivU |
| 16 | TMPJH46B | fU(ps)mC(ps)fAmCfCmUfGmCfUmUfCmUfUmCfUmGfGmUfU ivU |
| 17 | TMPJH47A | mA(ps)fA(ps)mCfCmAfGmAfAmGfAmAfGmCfAmGfGmUfGmA ivC |
| 18 | TMPJH47B | fU(ps)mC(ps)fAmCfCmUfGmCfUmUfCmUfUmCfUmGfGmUfU ivC |
| 19 | TMPJH48A | mA(ps)fA(ps)mCfCmAfGmAfAmGfAmAfGmCfAmGfGmUfGmA ivG |
| 20 | TMPJH48B | fU(ps)mC(ps)fAmCfCmUfGmCfUmUfCmUfUmCfUmGfGmUfU ivG |
| 21 | TMP82A | mA(ps)fA(ps)mCfCmAfGmAfAmGfAmAfGmCfAmGfGmUfGmA(ps)ivA |
| 22 | TMP82B | fU(ps)mC(ps)fAmCfCmUfGmCfUmUfCmUfUmCfUmGfGmUfU(ps)ivA |
| 23 | TMP83A | mA(ps)fA(ps)mCfCmAfGmAfAmGfAmAfGmCfAmGfGmUfGmA(ps)ivG |
| 24 | TMP83B | fU(ps)mC(ps)fAmCfCmUfGmCfUmUfCmUfUmCfUmGfGmUfU(ps)ivG |
| 25 | TMP84A | mA(ps)fA(ps)mCfCmAfGmAfAmGfAmAfGmCfAmGfGmUfG ivA |
| 26 | TMP84B | fU(ps)mC(ps)fAmCfCmUfGmCfUmUfCmUfUmCfUmGfGmUfU ivG |
| 27 | TMP85A | mA(ps)fA(ps)mCfCmAfGmAfAmGfAmAfGmCfAmGfGmUfG ivU |
| 28 | TMP85B | fU(ps)mC(ps)fAmCfCmUfGmCfUmUfCmUfUmCfUmGfGmUfU ivG |
| 29 | TMP86A | mA(ps)fA(ps)mCfCmAfGmAfAmGfAmAfGmCfAmGfGmUfG ivC |
| 30 | TMP86B | fU(ps)mC(ps)fAmCfCmUfGmCfUmUfCmUfUmCfUmGfGmUfU ivG |
| 31 | TMP87A | mA(ps)fA(ps)mCfCmAfGmAfAmGfAmAfGmCfAmGfGmUfG ivG |
| 32 | TMP87B | fU(ps)mC(ps)fAmCfCmUfGmCfUmUfCmUfUmCfUmGfGmUfU ivG |
| 33 | TMP88A | mA(ps)fA(ps)mCfCmAfGmAfAmGfAmAfGmCfAmGfGmUfGmA ivG |

-continued

| SEQ ID | Name | Sequence (5'-3') |
|---|---|---|
| 34 | TMP88B | fU(ps)mC(ps)fAmCfCmUfGmCfUmUfCmUfUmCfUmGfGmU ivA |
| 35 | TMP89A | mA(ps)fA(ps)mCfCmAfGmAfAmGfAmAfGmCfAmGfGmUfGmA ivG |
| 36 | TMP89B | fU(ps)mC(ps)fAmCfCmUfGmCfUmUfCmUfUmCfUmGfGmU ivU |
| 37 | TMP90A | mA(ps)fA(ps)mCfCmAfGmAfAmGfAmAfGmCfAmGfGmUfGmA ivG |
| 38 | TMP90B | fU(ps)mC(ps)fAmCfCmUfGmCfUmUfCmUfUmCfUmGfGmU ivC |
| 39 | TMP91A | mA(ps)fA(ps)mCfCmAfGmAfAmGfAmAfGmCfAmGfGmUfGmA ivG |
| 40 | TMP91B | fU(ps)mC(ps)fAmCfCmUfGmCfUmUfCmUfUmCfUmGfGmU ivG |
| 41 | STS12009L4A | mA(ps)fA(ps)mCfCmAfGmAfAmGfAmAfGmCfAmGfGmU(ps)fG(ps)mA |
| 42 | STS12009L4B | [ST23(ps)]3 ST41(ps) fUmCfAmCfCmUfGmCfUmUfCmUfUmCfUmGfG(ps)mU(ps)fU |
| 43 | STS12009V10L4A | mA(ps)fA(ps)mCfCmAfGmAfAmGfAmAfGmCfAmGfGmUfGmA ivA |
| 44 | STS12009V10L4B | [ST23(ps)]3 ST41(ps) fUmCfAmCfCmUfGmCfUmUfCmUfUmCfUmGfGmUfU ivA |
| 45 | STS12009V11L4A | mA(ps)fA(ps)mCfCmAfGmAfAmGfAmAfGmCfAmGfGmUfGmA ivG |
| 46 | STS12009V11L4B | [ST23(ps)]3 ST41(ps) fUmCfAmCfCmUfGmCfUmUfCmUfUmCfUmGfGmUfU ivG |
| 47 | STS12009V29L4A | mA(ps)fA(ps)mCfCmAfGmAfAmGfAmAfGmCfAmGfGmU(ps)fG(ps)mA ivA |
| 48 | STS12009V29L4B | [ST23(ps)]3 ST41(ps) fUmCfAmCfCmUfGmCfUmUfCmUfUmCfUmGfG(ps)mU(ps)fU ivA |
| 49 | STS12009V30L4A | mA(ps)fA(ps)mCfCmAfGmAfAmGfAmAfGmCfAmGfGmU(ps)fG(ps)mA ivG |
| 50 | STS12009V30L4B | [ST23(ps)]3 ST41(ps) fUmCfAmCfCmUfGmCfUmUfCmUfUmCfUmGfG(ps)mU(ps)fU ivG |
| 51 | ALD01A | mA(ps)fA(ps)mUfGmUfUmUfUmCfCmUfGmCfUmGfAmC(ps)fG(ps)mG |
| 52 | ALD01B | fC(ps)mC(ps)fGmUfCmAfGmCfAmGfGmAfAmAfAmCfA(ps)mU(ps)fU |
| 53 | ALD02A | mA(ps)fA(ps)mUfGmUfUmUfUmCfCmUfGmCfUmGfAmCfGmG ivA |
| 54 | ALD02B | fC(ps)mC(ps)fGmUfCmAfGmCfAmGfGmAfAmAfAmCfAmUfU ivA |
| 55 | ALD03A | mA(ps)fA(ps)mUfGmUfUmUfUmCfCmUfGmCfUmGfAmCfGmG ivU |
| 56 | ALD03B | fC(ps)mC(ps)fGmUfCmAfGmCfAmGfGmAfAmAfAmCfAmUfU ivU |
| 57 | ALD04A | mA(ps)fA(ps)mUfGmUfUmUfUmCfCmUfGmCfUmGfAmCfGmG ivC |
| 58 | ALD04B | fC(ps)mC(ps)fGmUfCmAfGmCfAmGfGmAfAmAfAmCfAmUfU ivC |
| 59 | ALD05A | mA(ps)fA(ps)mUfGmUfUmUfUmCfCmUfGmCfUmGfAmCfGmG ivG |
| 60 | ALD05B | fC(ps)mC(ps)fGmUfCmAfGmCfAmGfGmAfAmAfAmCfAmUfU ivG |
| 61 | ALD06A | mA(ps)fA(ps)mUfGmUfUmUfUmCfCmUfGmCfUmGfAmCfG ivA |
| 62 | ALD06B | fC(ps)mC(ps)fGmUfCmAfGmCfAmGfGmAfAmAfAmCfAmU ivA |
| 63 | ALD07A | mA(ps)fA(ps)mUfGmUfUmUfUmCfCmUfGmCfUmGfAmCfG ivU |
| 64 | ALD07B | fC(ps)mC(ps)fGmUfCmAfGmCfAmGfGmAfAmAfAmCfAmU ivU |
| 65 | ALD08A | mA(ps)fA(ps)mUfGmUfUmUfUmCfCmUfGmCfUmGfAmCfG ivC |
| 66 | ALD08B | fC(ps)mC(ps)fGmUfCmAfGmCfAmGfGmAfAmAfAmCfAmU ivC |
| 67 | ALD09A | mA(ps)fA(ps)mUfGmUfUmUfUmCfCmUfGmCfUmGfAmCfG ivG |

-continued

| SEQ ID | Name | Sequence (5'-3') |
|---|---|---|
| 68 | ALD09B | fC(ps)mC(ps)fGmUfCmAfGmCfAmGfGmAfAmAfAmCfAmU ivG |
| 69 | STS22002L6A | mA(ps)fA(ps)mUfGmUfUmUfUmCfCmUfGmCfUmGfAmC(ps)fG(ps)mG |
| 70 | STS22002L6B | [ST23(ps)]3 ST43(ps) fCmCfGmUfCmAfGmCfAmGfGmAfAmAfAmCfA(ps)mU(ps)fU |
| 71 | STS22002V1L6A | mA(ps)fA(ps)mUfGmUfUmUfUmCfCmUfGmCfUmGfAmC(ps)fG(ps)mG |
| 72 | STS22002V1L6B | [ST23(ps)]3 ST43(ps) fCmCfGmUfCmAfGmCfAmGfGmAfAmAfAmCfAmU ivA |
| 73 | STS22002V2L6A | mA(ps)fA(ps)mUfGmUfUmUfUmCfCmUfGmCfUmGfAmC(ps)fG(ps)mG |
| 74 | STS22002V2L6B | [ST23(ps)]3 ST43(ps) fCmCfGmUfCmAfGmCfAmGfGmAfAmAfAmCfAmU ivG |
| 75 | STS22002V3L6A | mA(ps)fA(ps)mUfGmUfUmUfUmCfCmUfGmCfUmGfAmCfGmG ivA |
| 76 | STS22002V3L6B | [ST23(ps)]3 ST43(ps) fCmCfGmUfCmAfGmCfAmGfGmAfAmAfAmCfA(ps)mU(ps)fU |
| 77 | STS22002V4L6A | mA(ps)fA(ps)mUfGmUfUmUfUmCfCmUfGmCfUmGfAmCfGmG ivG |
| 78 | STS22002V4L6B | [ST23(ps)]3 ST43(ps) fCmCfGmUfCmAfGmCfAmGfGmAfAmAfAmCfA(ps)mU(ps)fU |
| 79 | STS22006L6A | mU (ps) fC (ps) mUfUmCfUmUfAmAfAmCfUmGfAmGfUmU (ps) fU (ps) mC |
| 80 | STS22006L6B | [ST23(ps)]3 ST43(ps) fGmAfAmAfCmUfCmAfGmUfUmUfAmAfGmAfA (ps) mG (ps) fA |
| 81 | STS22006V7L6A | mU (ps) fC (ps) mUfUmCfUmUfAmAfAmCfUmGfAmGfUmU (ps) fU (ps) mC |
| 82 | STS22006V7L6B | [ST23(ps)]3 ST43 (ps) fGmAfAmAfCmUfCmAfGmUfUmUfAmAfGmAfAmGfA ivA |
| 83 | STS22006V8L6A | mU (ps) fC (ps) mUfUmCfUmUfAmAfAmCfUmGfAmGfUmU (ps) fU (ps) mC ivA |
| 84 | STS22006V8L6B | [ST23(ps)]3 ST43 (ps) fGmAfAmAfCmUfCmAfGmUfUmUfAmAfGmAfA (ps) mG (ps) fA |
| 85 | STS22006V9L6A | mU (ps) fC (ps) mUfUmCfUmUfAmAfAmCfUmGfAmGfUmUfUmC ivA |
| 86 | STS22006V9L6B | [ST23(ps)]3 ST43(ps) fGmAfAmAfCmUfCmAfGmUfUmUfAmAfGmAfAmGfA ivA |
| 87 | STS22006V10L35A | mU (ps) fC (ps) mUfUmCfUmUfAmAfAmCfUmGfAmGfUmU (ps) fU (ps) mC [(ps)Ser(GN)]3 |
| 88 | STS22006V10L35B | ivA fGmAfAmAfCmUfCmAfGmUfUmUfAmAfGmAfAmGfA ivA |
| 89 | STS22009L6A | mA (ps) fU (ps) mGfUmAfGmCfCmGfAmGfGmAfUmCfUmU (ps) fC (ps) mU |
| 90 | STS22009L6B | [ST23(ps)]3 ST43 (ps) fAmGfAmAfGmAfUmCfCmUfCmGfGmCfUmAfC (ps) mA (ps) fU |
| 91 | STS22009V3L6A | mA (ps) fU (ps) mGfUmAfGmCfCmGfAmGfGmAfUmCfUmU (ps) fC (ps) mU |
| 92 | STS22009V3L6B | [ST23(ps)]3 ST43 (ps) fAmGfAmAfGmAfUmCfCmUfCmGfGmCfUmAfCmAfU ivA |
| 93 | STS22009V4L6A | mA (ps) fU (ps) mGfUmAfGmCfCmGfAmGfGmAfUmCfUmUfCmU ivA |
| 94 | STS22009V4L6B | [ST23(ps)]3 ST43 (ps) fAmGfAmAfGmAfUmCfCmUfCmGfGmCfUmAfC (ps) mA (ps) fU |
| 95 | STS22009V5L6A | mA (ps) fU (ps) mGfUmAfGmCfCmGfAmGfGmAfUmCfUmUfCmU ivA |
| 96 | STS22009V5L6B | [ST23(ps)]3 ST43 (ps) fAmGfAmAfGmAfUmCfCmUfCmGfGmCfUmAfCmAfU ivA |
| 97 | STS22009V6L6A | mA (ps) fU (ps) mGfUmAfGmCfCmGfAmGfGmAfUmCfUmU (ps) fC (ps) mU[(ps)Ser(GN)]3 |
| 98 | STS22009V6L6B | ivA fAmGfAmAfGmAfUmCfCmUfCmGfGmCfUmAfCmAfU ivA |
| 99 | STS16001L1A | mU (ps) fU (ps) mAfUmAfGmAfGmCfAmAfGmAfAmCfAmCfUmG (ps) fU (ps) mU |
| 100 | STS16001L1B | [ST23(ps)]3 ltrb(ps) fAmAfCmAfGmUfGmUfUmCfUmUfGmCfUmCfUmAfU (ps) mA (ps) fA |
| 101 | STS16001V11L1A | mU (ps) fU (ps) mAfUmAfGmAfGmCfAmAfGmAfAmCfAmCfUmG (ps) fU (ps) mU |
| 102 | STS16001V11L1B | [ST23(ps)]3 ltrb(ps) fAmAfCmAfGmUfGmUfUmCfUmUfGmCfUmCfUmAfUmAfA ivA |

-continued

| SEQ ID | Name | Sequence (5'-3') |
|---|---|---|
| 103 | STS16001V12L1A | mU (ps) fU (ps) mAfUmAfGmAfGmCfAmAfGmAfAmCfAmCfUmGfUmU ivA |
| 104 | STS16001V12L1B | [ST23(ps)]3 ltrb(ps) fAmAfCmAfGmUfGmUfUmCfUmUfGmCfUmCfUmAfU (ps) mA (ps) fA |
| 105 | STS16001V13L1A | mU (ps) fU (ps) mAfUmAfGmAfGmCfAmAfGmAfAmCfAmCfUmGfUmU ivA |
| 106 | STS16001V13L1B | [ST23(ps)]3 ltrb(ps) fAmAfCmAfGmUfGmUfUmCfUmUfGmCfUmCfUmAfUmAfA ivA |
| 107 | STS16001V14L35A | mU (ps) fU (ps) mAfUmAfGmAfGmCfAmAfGmAfAmCfAmCfUmG (ps) fU (ps) mU[(ps)Ser(GN)]3 |
| 108 | STS16001V14L35B | ivA fAmAfCmAfGmUfGmUfUmCfUmUfGmCfUmCfUmAfUmAfA ivA |
| 109 | STS22002L6A | mA (ps) fA (ps) mUfGmUfUmUfUmCfCmUfGmCfUmGfAmC (ps) fG (ps) mG |
| 110 | STS22002L6B | [ST23(ps)]3 ST43 (ps) fCmCfGmUfCmAfGmCfAmGfGmAfAmAfAmCfA (ps) mU (ps) fU |
| 111 | STS22002V8L6A | mA (ps) fA (ps) mUfGmUfUmUfUmCfCmUfGmCfUmGfAmCfG ivA |
| 112 | STS22002V8L6B | [ST23(ps)]3 ST43 (ps) fCmCfGmUfCmAfGmCfAmGfGmAfAmAfAmCfA (ps) mU (ps) fU |
| 113 | STS22002V9L6A | mA (ps) fA (ps) mUfGmUfUmUfUmCfCmUfGmCfUmGfAmCfG ivA |
| 114 | STS22002V9L6B | [ST23(ps)]3 ST43 (ps) fCmCfGmUfCmAfGmCfAmGfGmAfAmAfAmCfAmU ivA |
| 115 | STS22002V10L6A | mA (ps) fA (ps) mUfGmUfUmUfUmCfCmUfGmCfUmGfAmCfGmG ivA |
| 116 | STS22002V10L6B | [ST23(ps)]3 ST43 fCmCfGmUfCmAfGmCfAmGfGmAfAmAfAmCfAmU ivA |
| 117 | STS22006V1L6A | mU (ps) fC (ps) mUfUmCfUmUfAmAfAmCfUmGfAmGfUmU (ps) fU (ps) mC |
| 118 | STS22006V1L6B | [ST23(ps)]3 ST43(ps) fGmAfAmAfCmUfCmAfGmUfUmUfAmAfGmAfAmG ivA |
| 119 | STS22009V1L6A | mA (ps) fU (ps) mGfUmAfGmCfCmGfAmGfGmAfUmCfUmU (ps) fC (ps) mU |
| 120 | STS22009V1L6B | [ST23(ps)]3 ST43(ps) mAmGmAmAmGmAfUfCfCmUmCmGmGmCmUmAmCmA ivA |
| 121 | STS22009V2L6A | mA (ps) fU (ps) mGmUmAmGmCmCmGmAmGmGmAfUmCmUmU (ps) mC (ps) mU |
| 122 | STS22009V2L6B | [ST23(ps)]3 ST43(ps) mAmGmAmAmGmAfUfCfCmUmCmGmGmCmUmAmCmA ivA |
| 123 | TMPJH01A | AACCAGAAGAAGCAGGUGA |
| 124 | TMPJH01B | UCACCUGCUUCUUCUGGUU |
| 125 | TMPJH41A | AACCAGAAGAAGCAGGUGAA |
| 126 | TMPJH41B | UCACCUGCUUCUUCUGGUUA |
| 127 | TMPJH42A | AACCAGAAGAAGCAGGUGAU |
| 128 | TMPJH42B | UCACCUGCUUCUUCUGGUUU |
| 129 | TMPJH43A | AACCAGAAGAAGCAGGUGAC |
| 130 | TMPJH43B | UCACCUGCUUCUUCUGGUUC |
| 131 | TMPJH44A | AACCAGAAGAAGCAGGUGAG |
| 132 | TMPJH44B | UCACCUGCUUCUUCUGGUUG |
| 133 | TMP85A | AACCAGAAGAAGCAGGUGU |

| SEQ ID | Name | Sequence (5'-3') |
|---|---|---|
| 134 | TMP86A | AACCAGAAGAAGCAGGUGC |
| 135 | TMP87A | AACCAGAAGAAGCAGGUGG |
| 136 | TMP88B | UCACCUGCUUCUUCUGGUA |
| 137 | TMP90B | UCACCUGCUUCUUCUGGUC |
| 138 | TMP91B | UCACCUGCUUCUUCUGGUG |
| 139 | ALD01A | AAUGUUUUCCUGCUGACGG |
| 140 | ALD01B | CCGUCAGCAGGAAAACAUU |
| 141 | ALD02A | AAUGUUUUCCUGCUGACGGA |
| 142 | ALD02B | CCGUCAGCAGGAAAACAUUA |
| 143 | ALD03A | AAUGUUUUCCUGCUGACGGU |
| 144 | ALD03B | CCGUCAGCAGGAAAACAUUU |
| 145 | ALD04A | AAUGUUUUCCUGCUGACGGC |
| 146 | ALD04B | CCGUCAGCAGGAAAACAUUC |
| 147 | ALD05A | AAUGUUUUCCUGCUGACGGG |
| 148 | ALD05B | CCGUCAGCAGGAAAACAUUG |
| 149 | ALD06A | AAUGUUUUCCUGCUGACGA |
| 150 | ALD06B | CCGUCAGCAGGAAAACAUA |
| 151 | ALD07A | AAUGUUUUCCUGCUGACGU |
| 152 | ALD08A | AAUGUUUUCCUGCUGACGC |
| 153 | ALD08B | CCGUCAGCAGGAAAACAUC |
| 154 | ALD09B | CCGUCAGCAGGAAAACAUG |
| 155 | STS22006L6A | UCUUCUUAAACUGAGUUUC |
| 156 | STS22006L6B | GAAACUCAGUUUAAGAAGA |
| 157 | STS22009L6A | AUGUAGCCGAGGAUCUUCU |
| 158 | STS22009L6B | AGAAGAUCCUCGGCUACAU |
| 159 | STS16001L1A | UUAUAGAGCAAGAACACUGUU |
| 160 | STS16001L1B | AACAGUGUUCUUGCUCUAUAA |
| 161 | STS22002L6A | AAUGUUUUCCUGCUGACGG |
| 162 | STS22002L6B | CCGUCAGCAGGAAAACAUU |
| 163 | STS22002V8L6A | AAUGUUUUCCUGCUGACGA |
| 164 | STS22002V9L6B | CCGUCAGCAGGAAAACAUA |
| 165 | STS22009V1L6B | AGAAGAUCCUCGGCUACAA |
| 166 | STS18001L4A | mU(ps)fC(ps)mGfAmAfGmUfAmUfUmCfCmGfCmGfUmA(ps)fC(ps)mG |
| 167 | STS18001L4B | [ST23(ps)]3 ST41(ps)fCmGfUmAfCmGfCmGfUmGmAfAmUfAmCfUmC(ps)mG(ps)fA |
| 168 | STS16001V4L11A | mU(ps)fU(ps)mAfUmAfGmAfGmCfAmAfGmAfAmCfAmCfUmG(ps)fU(ps)mU(ps)GlyC3Am(GaINAc) |
| 169 | STS16001V4L11B | fA(ps)mA(ps)fCmAfGmUfGmUfUmCfUmUfGmCfUmCfUmAfU(ps)mA(ps)fA |
| 170 | STS16001L22A | mU(ps)fU(ps)mAfUmAfGmAfGmCfAmAfGmAfAmCfAmCfUmG(ps)fU(ps)mU |

| SEQ ID | Name | Sequence (5'-3') |
|---|---|---|
| 171 | STS16001L22B | Ser(GN)(ps)Ser(GN)(ps)Ser(GN)(ps)fAmAfCmAfGmUfGmUfUmCfUmUfGmCfUmCfUmAfU(ps)mA(ps)fA |
| 172 | STS16001V7L22A | (po)ivAfUmAfUmAfGmAfGmCfAmAfGmAfAmCfAmCfUmG(ps)fU(ps)mU |
| 173 | STS16001V7L22B | Ser(GN)(ps)Ser(GN)(ps)Ser(GN)(ps)fAmAfCmAfGmUfGmUfUmCfUmUfGmCfUmCfUmAfU(ps)mA(ps)fA |
| 174 | STS16001V8L22A | (po)ivGfUmAfUmAfGmAfGmCfAmAfGmAfAmCfAmCfUmG(ps)fU(ps)mU |
| 175 | STS16001V8L22B | Ser(GN)(ps)Ser(GN)(ps)Ser(GN)(ps)fAmAfCmAfGmUfGmUfUmCfUmUfGmCfUmCfUmAfU(ps)mA(ps)fA |
| 176 | STS16001V9L22A | (po)ivUfUmAfUmAfGmAfGmCfAmAfGmAfAmCfAmCfUmG(ps)fU(ps)mU |
| 177 | STS16001V9L22B | Ser(GN)(ps)Ser(GN)(ps)Ser(GN)(ps)fAmAfCmAfGmUfGmUfUmCfUmUfGmCfUmCfUmAfU(ps)mA(ps)fA |
| 178 | STS16001V10L22A | (po)ivCfUmAfUmAfGmAfGmCfAmAfGmAfAmCfAmCfUmG(ps)fU(ps)mU |
| 179 | STS16001V10L22B | Ser(GN)(ps)Ser(GN)(ps)Ser(GN)(ps)fAmAfCmAfGmUfGmUfUmCfUmUfGmCfUmCfUmAfU(ps)mA(ps)fA |
| 180 | STS16001V6L11A | mU(ps)fU(ps)mAfUmAfGmAfGmCfAmAfGmAfAmCfAmCfUmG(ps)fU(ps)mU(ps)GlyC3Am(GalNAc) |
| 181 | STS16001V6L11B | ivAfAmAfCmAfGmUfGmUfUmCfUmUfGmCfUmCfUmAfU(ps)mA(ps)fA |
| 182 | STS16001V7L11A | mU(ps)fU(ps)mAfUmAfGmAfGmCfAmAfGmAfAmCfAmCfUmG(ps)fU(ps)mU(ps)GlyC3Am(GalNAc) |
| 183 | STS16001V7L11B | ivGfAmAfCmAfGmUfGmUfUmCfUmUfGmCfUmCfUmAfU(ps)mA(ps)fA |
| 184 | STS16001V8L11A | mU(ps)fU(ps)mAfUmAfGmAfGmCfAmAfGmAfAmCfAmCfUmG(ps)fU(ps)mU(ps)GlyC3Am(GalNAc) |
| 185 | STS16001V8L11B | ivUfAmAfCmAfGmUfGmUfUmCfUmUfGmCfUmCfUmAfU(ps)mA(ps)fA |
| 186 | STS16001V9L11A | mU(ps)fU(ps)mAfUmAfGmAfGmCfAmAfGmAfAmCfAmCfUmG(ps)fU(ps)mU(ps)GlyC3Am(GalNAc) |
| 187 | STS16001V9L11B | ivCfAmAfCmAfGmUfGmUfUmCfUmUfGmCfUmCfUmAfU(ps)mA(ps)fA |
| 188 | STS18001L4A | UCGAAGUAUUCCGCGUACG |
| 189 | STS18001L4B | CGUACGCGGAAUACUUCGA |
| 190 | STS16001V4L11A | UUAUAGAGCAAGAACACUGUU |
| 191 | STS16001V7L22A | AUAUAGAGCAAGAACACUGUU |
| 192 | STS16001V8L22A | GUAUAGAGCAAGAACACUGUU |
| 193 | STS16001V10L22A | CUAUAGAGCAAGAACACUGUU |
| 194 | STS16001V4L11B | AACAGUGUUCUUGCUCUAUAA |
| 195 | STS16001V6L11B | AAACAGUGUUCUUGCUCUAUAA |
| 196 | STS16001V7L11B | GAACAGUGUUCUUGCUCUAUAA |
| 197 | STS16001V8L11B | UAACAGUGUUCUUGCUCUAUAA |
| 198 | STS16001V9L11B | CAACAGUGUUCUUGCUCUAUAA |

Key
mA, mU, mC, mG—2'-OMe RNA
fA, fU, fC, fG—2'-F RNA
ivA, ivU, ivC, ivG—inverted RNA (3'-3' from SEQ ID NO 1-122; 5'-5' from SEQ ID NO 166-187) (po)ivA, (po)ivU, (po)ivC, (po)ivG: 5-5-linked inverted ribonucleotide with 3-phosphate
(ps)—phosphorothioate The sequences listed above may be disclosed with a linker or ligand, such as GalNAC or (ps) or (ps2) linkages for example. These form an optional, but preferred, part of the sequence of the sequence listing.

The following abbreviations may be used:
| | |
|---|---|
| ivN | Inverted nucleotide, either 3'-3' or 5'-5' |
| (ps2) | Phosphorodithioate |
| vinylphosphonate | Vinyl-(E)-phosphonate |
| FAM | 6-Carboxyfluorescein |
| TAMRA | 5-Carboxytetramethylrhodamine |
| BHQ1 | Black Hole Quencher 1 |
| (ps) | Phosphorothioate |
GN
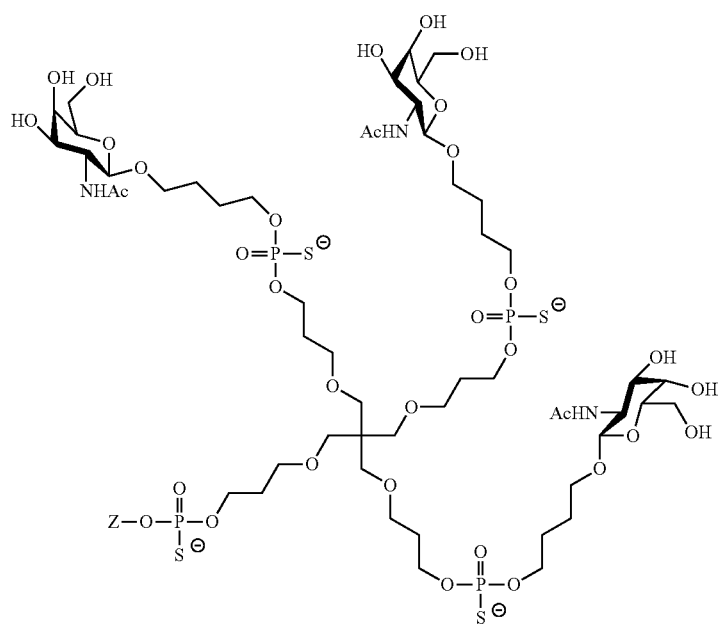
GN2
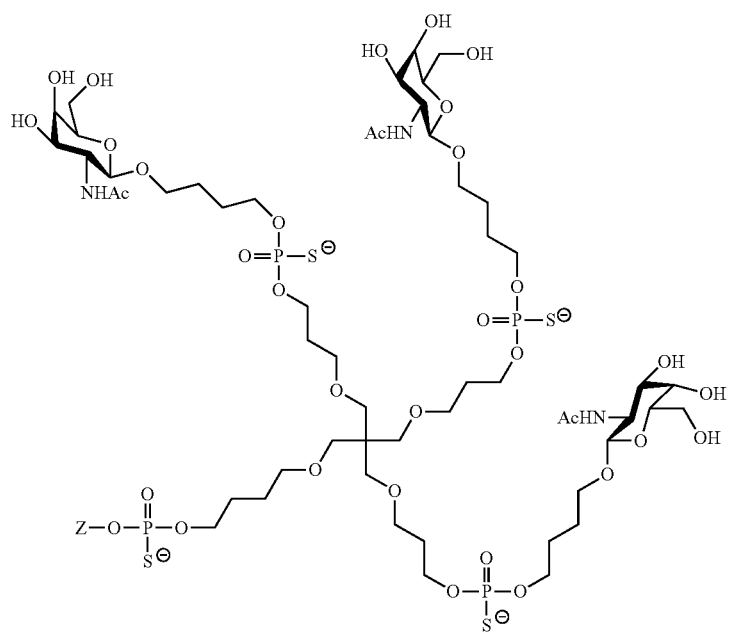

-continued
GN3
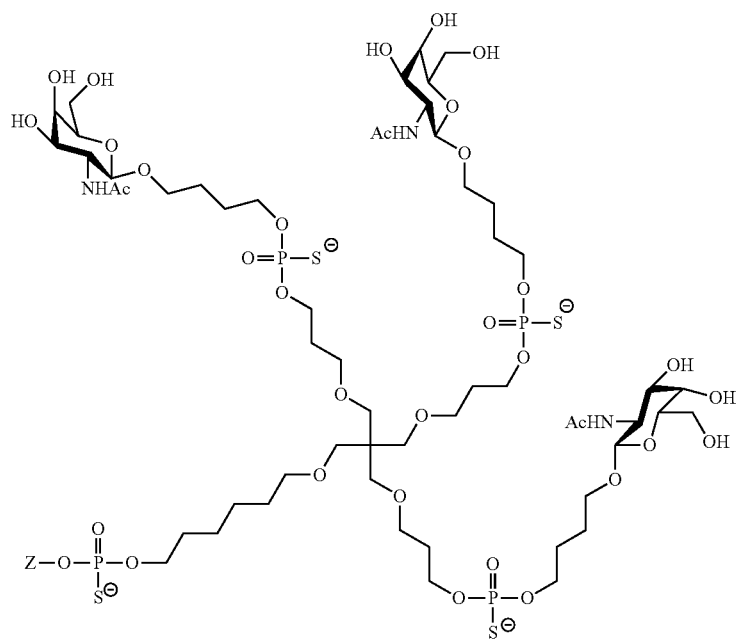
GNo    Same as GN2 but with phosphodiesters instead of phosphorothioates
ST23
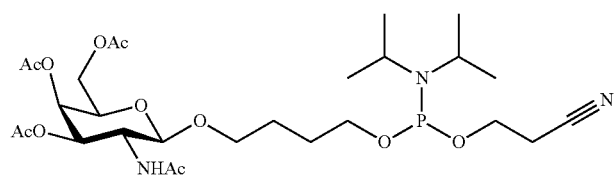
ST41/C4XLT
ST43/C6XLT
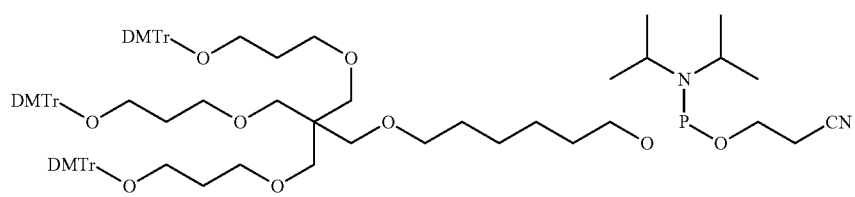
Long trebler/ltrb/STKS
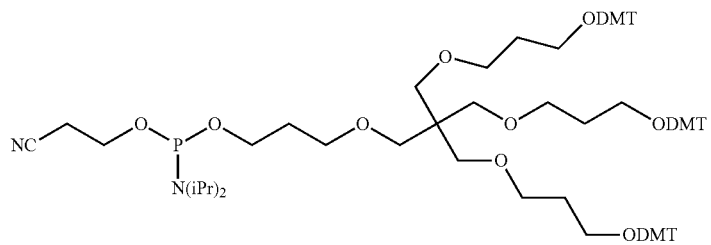
Ser(GN)
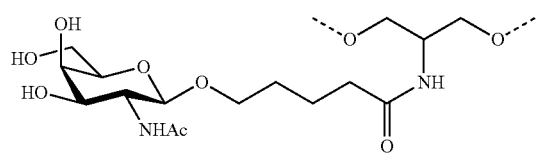

| | |
|---|---|
| GlyC3Am(GalNAc) | 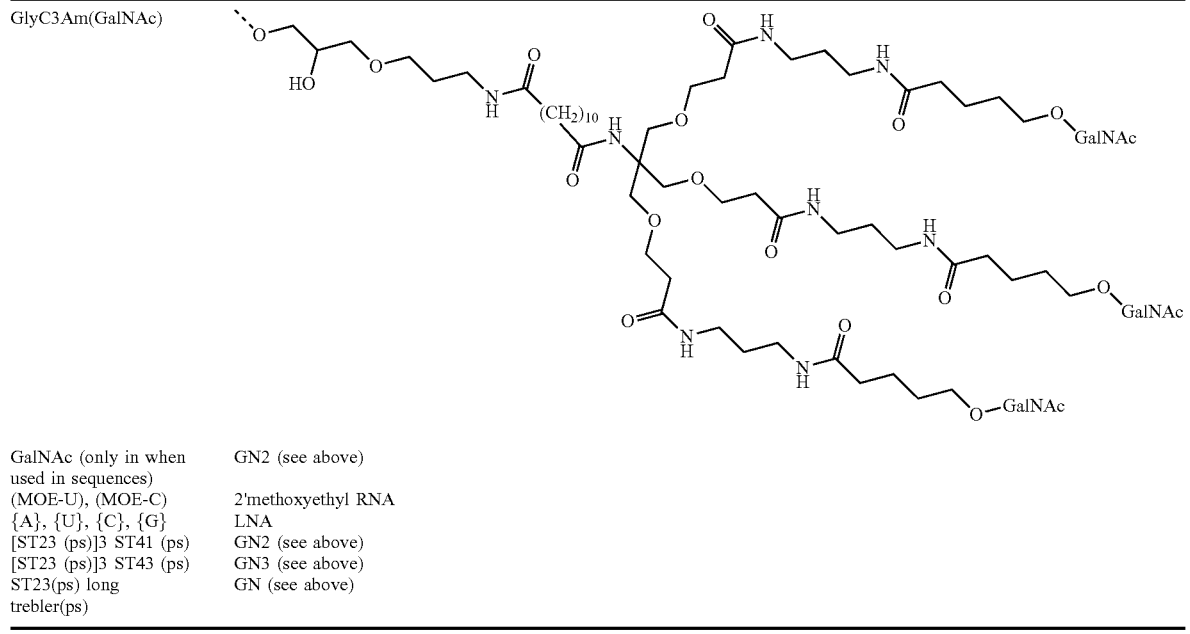 |
| GalNAc (only in when used in sequences) | GN2 (see above) |
| (MOE-U), (MOE-C) | 2'methoxyethyl RNA |
| {A}, {U}, {C}, {G} | LNA |
| [ST23 (ps)]3 ST41 (ps) | GN2 (see above) |
| [ST23 (ps)]3 ST43 (ps) | GN3 (see above) |
| ST23(ps) long trebler(ps) | GN (see above) |

STATEMENTS OF INVENTION

The statements reflect preferred features of the invention, and may each independently be combined with any aspect of the disclosure herein.

1. A nucleic acid for inhibiting expression of a target gene in a cell, comprising at least one duplex region that comprises at least a portion of a first strand and at least a portion of a second strand that is at least partially complementary to the first strand, wherein said first strand is at least partially complementary to at least a portion of RNA transcribed from said target gene to be inhibited and wherein the terminal nucleotide at the 3' end of at least one of the first strand and the second strand is an inverted nucleotide and is attached to the adjacent nucleotide via the 3' carbon of the terminal nucleotide and the 3' carbon of the adjacent nucleotide and/or the terminal nucleotide at the 5' end of at least one of the first strand and the second strand is an inverted nucleotide and is attached to the adjacent nucleotide via the 5' carbon of the terminal nucleotide and the 5' carbon of the adjacent nucleotide.

2. A nucleic acid according to statement 1, wherein the 3' and/or 5' inverted nucleotide of the first and/or second strand is attached to the adjacent nucleotide via a phosphate group by way of a phosphodiester linkage.

3. A nucleic acid according to statement 1, wherein the 3' and/or 5' inverted nucleotide of the first and/or second strand is attached to the adjacent nucleotide via a phosphorothioate group.

4. A nucleic acid according to statement 1, wherein 3' and/or 5' inverted nucleotide of the first and/or second strand is attached to the adjacent nucleotide via a phosphorodithioate group.

5. A nucleic acid according to any of statements 1 to 6, wherein the 3' and/or 5' inverted nucleotide of the first and/or second strand forms an overhang.

6. A nucleic acid according to any of statements 1 to 5, wherein the 3' and/or 5' inverted nucleotide of the first and/or second strand forms a blunt end.

7. A nucleic acid according to any of statements 1 to 6, wherein the first strand and the second strand are separate strands.

8. A nucleic acid according to any of statements 1 to 6, comprising a single strand that comprises the first strand and the second strand.

9. A nucleic acid according to any of statements 1 to 8, wherein said first strand and/or said second strand are each from 17-35 nucleotides in length.

10. A nucleic acid of any of statements 1 to 9, wherein the at least one duplex region consists of 19-25 nucleotide base pairs.

11. A nucleic acid of any preceding statement, which
  a) is blunt ended at both ends; or
  b) has an overhang at one end and a blunt end at the other; or
  c) has an overhang at both ends optionally a nucleic acid having an overhang at the 3' end of the first strand and which has a blunt end at the 3' of the second strand, optionally wherein the nucleic acid has an inverted nucleotide such as ivA on the 3' end of the second strand 3'-end at a blunt end.

12. A nucleic acid according to any preceding statement, wherein one or more nucleotides on the first and/or second strand are modified, to form modified nucleotides.

13. A nucleic acid of statement 12, wherein one or more of the odd numbered nucleotides of the first strand are modified.

14. A nucleic acid according to statement 13, wherein one or more of the even numbered nucleotides of the first strand are modified by at least a second modification, wherein the at least second modification is different from the modification of statement 9.

15. A nucleic acid of statement 14, wherein at least one of the one or more modified even numbered nucleotides is adjacent to at least one of the one or more modified odd numbered nucleotides.

16. A nucleic acid of any one of statements 13 to 15, wherein a plurality of odd numbered nucleotides are modified.

17. A nucleic acid of any one of statements 14 to 16, wherein a plurality of even numbered nucleotides are modified by a second modification.

18. A nucleic acid of any of statements 12 to 17, wherein the first strand comprises adjacent nucleotides that are modified by a common modification.

19. A nucleic acid of any of statements 13 to 18, wherein the first strand comprises adjacent nucleotides that are modified by a second modification that is different to the modification of statement 9.

20. A nucleic acid of any of statements 13 to 19, wherein one or more of the odd numbered nucleotides of the second strand are modified by a modification that is different to the modification of statement 9.

21. A nucleic acid according to any of statements 13 to 19, wherein one or more of the even numbered nucleotides of the second strand are modified by the modification of statement 9.

22. A nucleic acid of statement 20 or 21, wherein at least one of the one or more modified even numbered nucleotides of the second strand is adjacent to the one or more modified odd numbered nucleotides.

23. A nucleic acid of any of statements 20 to 22, wherein a plurality of odd numbered nucleotides of the second strand are modified by a common modification.

24. A nucleic acid of any of statements 20 to 23, wherein a plurality of even numbered nucleotides are modified by a modification according to statement 9.

25. A nucleic acid of any of statements 20 to 24, wherein a plurality of odd numbered nucleotides are modified by a second modification, wherein the second modification is different from the modification of statement 9.

26. A nucleic acid of any of statements 20 to 25, wherein the second strand comprises adjacent nucleotides that are modified by a common modification.

27. A nucleic acid of any of statements 20 to 26, wherein the second strand comprises adjacent nucleotides that are modified by a second modification that is different from the modification of statement 9.

28. A nucleic acid according to any one of statements 12 to 27, wherein each of the odd numbered nucleotides in the first strand and each of the even numbered nucleotides in the second strand are modified with a common modification.

29. A nucleic acid of any one of statements 13 to 28, wherein each of the even numbered nucleotides are modified in the first strand with a second modification and each of the odd numbered nucleotides are modified in the second strand with a second modification.

30. A nucleic acid according to any one of statements 20 to 29, wherein the modified nucleotides of the first strand are shifted by at least one nucleotide relative to the unmodified or differently modified nucleotides of the second strand.

31. A nucleic acid of any one of statements 1 to 30, wherein the first strand comprises a sequence selected from the group consisting of SEQ ID NO:s 1, 3, 5 and 7.

32. A nucleic acid of any one of statements 1 to 30, wherein the second strand comprises a sequence selected from the group consisting to SEQ ID NO:s 2, 4, 6 and 8.

33. A nucleic acid according to any one of statements 8 to 32, wherein the modification and/or modifications are each and individually selected from the group consisting of 3-terminal deoxy-thymine, 2'-O-methyl, a 2'-deoxy-modification, a 2'-amino-modification, a 2'-alkyl-modification, a morpholino modification, a phosphoramidate modification, 5'-phosphorothioate group modification, a 5' phosphate or 5' phosphate mimic modification and a cholesteryl derivative or a dodecanoic acid bisdecylamide group modification.

34. A nucleic acid according to any one of statements 8 to 33, wherein the modification is any one of a locked nucleotide, an abasic nucleotide or a non-natural base comprising nucleotide.

35. A nucleic acid according to any one of statements 8 to 34, wherein at least one modification is 2'-O-methyl.

36. A nucleic acid according to any one of statements 8 to 35, wherein at least one modification is 2'-F.

37. A nucleic acid according to any one of statements 1 to 36, wherein the inverted nucleotide at the 3' end of at least one of the first strand and the second strand and/or the inverted nucleotide at the 5' end of at least one of the first strand and the second strand is a purine, such as an adenine 38. A nucleic acid according to any one of statements 1 to 37, further comprising a ligand.

39. A nucleic acid according to any one of statements 1 to 38, comprising a phosphorothioate linkage between the terminal one, two or three 3' nucleotides and/or 5' nucleotides of the first and/or the second strand.

40. A nucleic acid according to any one of statements 1 to 39, comprising two phosphorothioate linkage between each of the three terminal 3' and between each of the three terminal 5' nucleotides on the first strand, and two phosphorothioate linkages between the three terminal nucleotides of the 3' end of the second strand.

41. A nucleic acid for inhibiting expression of a target gene in a cell, comprising at least one duplex region that comprises at least a portion of a first strand and at least a portion of a second strand that is at least partially complementary to the first strand, wherein said first strand is at least partially complementary to at least a portion of RNA transcribed from said target gene to be inhibited and wherein the terminal nucleotide at the 3' end of at least one of the first strand and the second strand is an inverted nucleotide and is attached to the adjacent nucleotide via the 3' carbon of the terminal nucleotide and the 3' carbon of the adjacent nucleotide and/or the terminal nucleotide at the 5' end of at least one of the first strand and the second strand is an inverted nucleotide and is attached to the adjacent nucleotide via the 5' carbon of the terminal nucleotide and the 5' carbon of the adjacent nucleotide, and wherein the nucleic acid molecule is directly or indirectly conjugated to a ligand via a linker.

42. A nucleic acid according to any of statements 38 to 41, wherein the ligand comprises one or more GalNac ligands and derivatives thereof, such as comprising a GalNAc moiety at the second strand 5'-end.

43. A nucleic acid according to any of statements 38 to 42, wherein the ligand is directly or indirectly conjugated to a nucleic acid as defined in any preceding statements by a bivalent or trivalent branched linker.

44. A nucleic acid of statement 41, wherein the nucleotides are modified as defined in any preceding statements.

45. A nucleic acid of any preceding statement, wherein the ligand comprises the formula I:

$$[S-X^1-P-X^2]_3\text{-}A\text{-}X^3- \quad (I)$$

wherein:
S represents a saccharide, wherein the saccharide is N-acetyl galactosamine;
$X^1$ represents $C_3$-$C_6$ alkylene or $(-CH_2-CH_2-O)_m(-CH_2)_2-$ wherein m is 1, 2, or 3;
P is a phosphate or modified phosphate (preferably a thiophosphate);
$X^2$ is alkylene or an alkylene ether of the formula $(-CH_2)_n-O-CH_2-$ where n=1-6;

A is a branching unit;
X³ represents a bridging unit;
wherein a nucleic acid according to the present invention is conjugated to X³ via a phosphate or modified phosphate (preferably a thiophosphate).
46. A conjugated nucleic acid having one of the following structures:
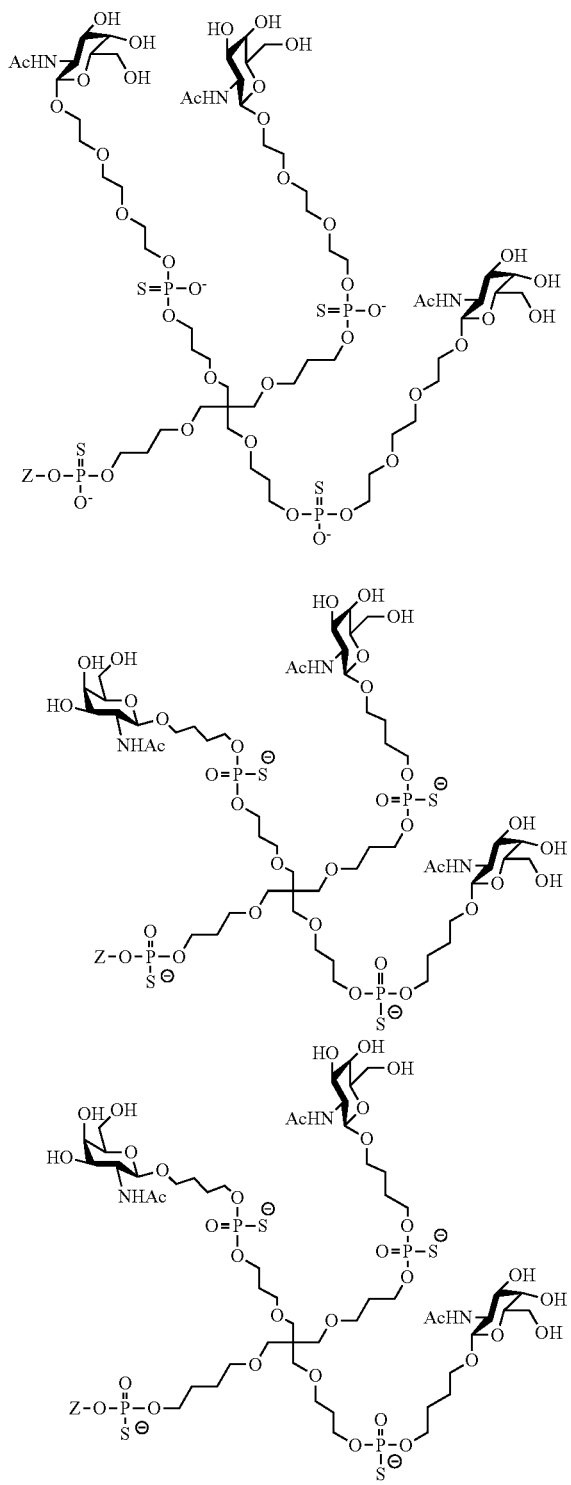
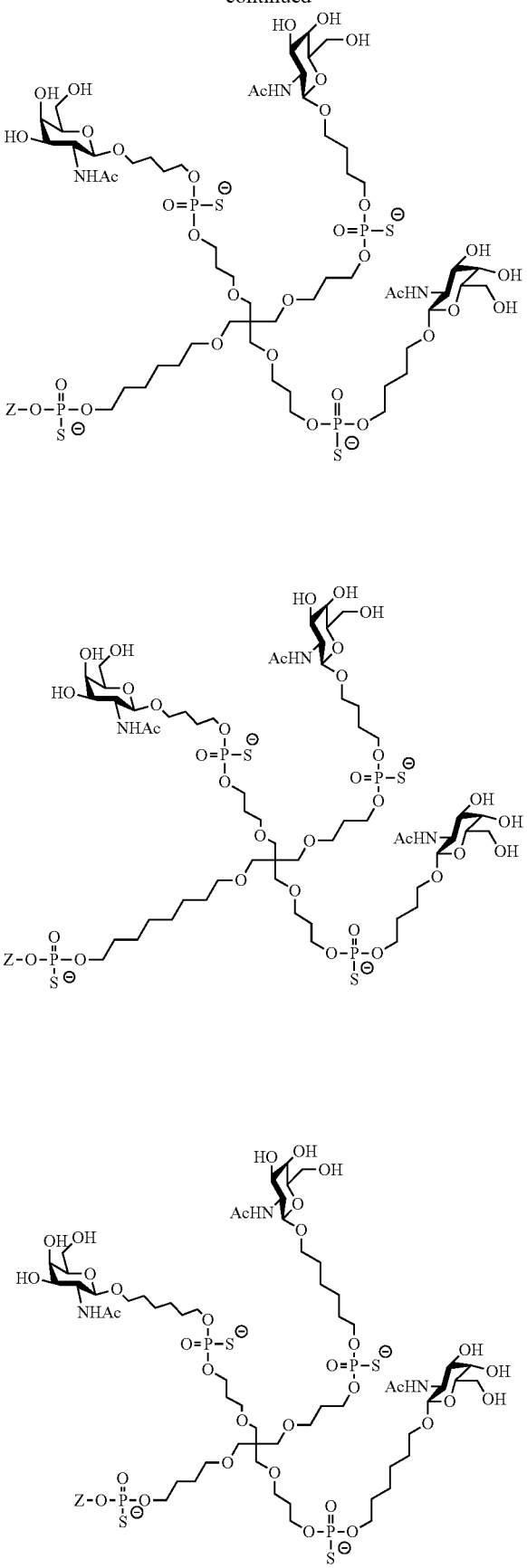

93
-continued

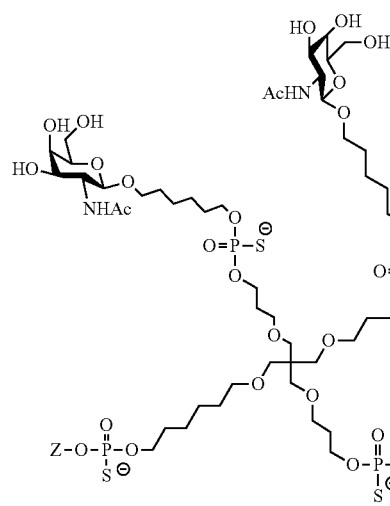

94
-continued

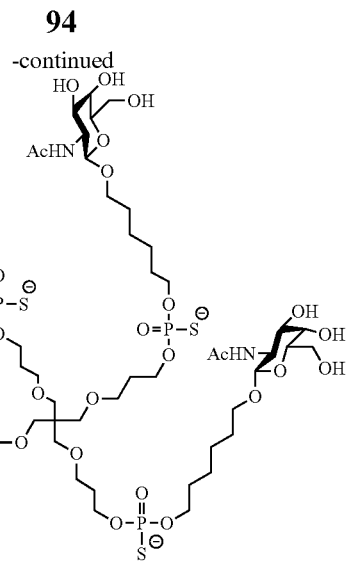

wherein Z is a nucleic acid according to any of statements 1 to 40.

47. A nucleic acid of any preceding statement, wherein the ligand comprises:

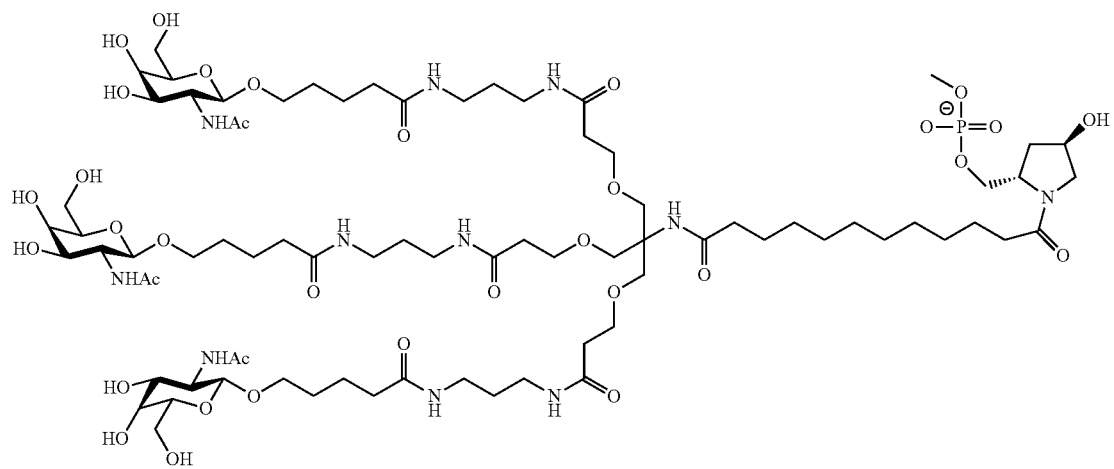

48. A composition comprising a nucleic acid or conjugated nucleic acid as defined in any preceding statement and a formulation comprising:
   i) a cationic lipid, or a pharmaceutically acceptable salt thereof;
   ii) a steroid;
   iii) a phosphatidylethanolamine phospholipid;
   iv) a PEGylated lipid.

49. A composition according to statement 48, wherein in the formulation the content of the cationic lipid component is from about 55 mol % to about 65 mol % of the overall lipid content of the lipid formulation, preferably about 59 mol % of the overall lipid content of the lipid formulation.

50. A composition as disclosed in statement 48, wherein the formulation comprises;
A cationic lipid having the structure;

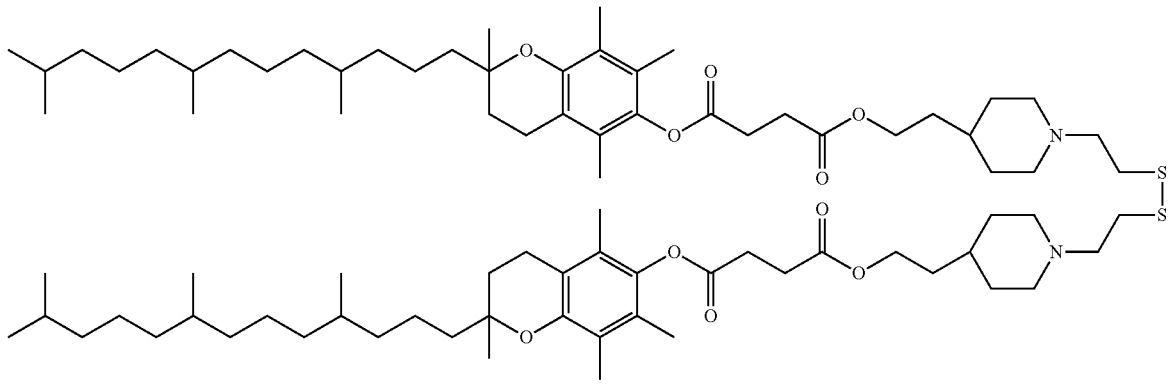 [SMILES: Cc1c(C)c2c(c(C)c1OC(=O)CCC(=O)OCCC1CCN(CCSSCCN3CCC(CCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2]

the steroid has the structure;

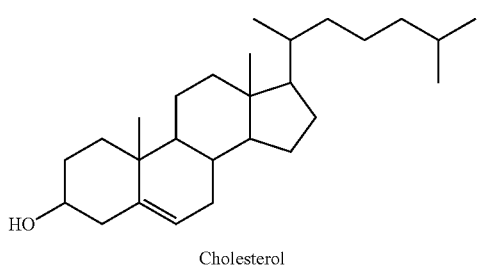 [SMILES: CC(C)CCCC(C)C1CCC2C3CC=C4CC(O)CCC4(C)C3CCC12C]
Cholesterol the phosphatidylethanolamine phospholipid has the structure;

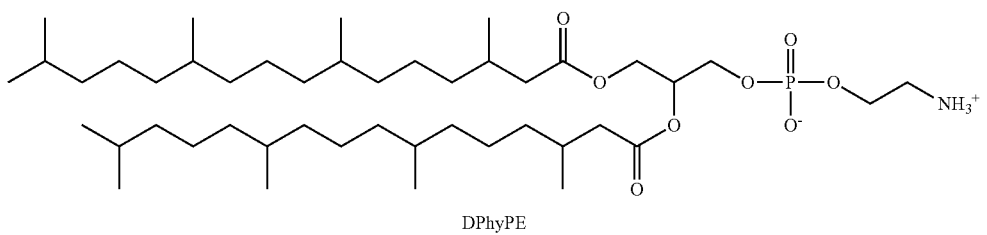 [SMILES: CC(C)CCCC(C)CCCC(C)CCCC(C)CC(=O)OCC(COP(=O)([O-])OCC[NH3+])OC(=O)CC(C)CCCC(C)CCCC(C)CCCC(C)C]
DPhyPE and the PEGylated lipid has the structure;

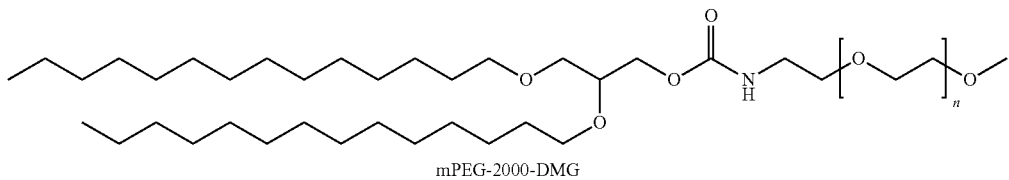
mPEG-2000-DMG

51. A composition comprising a nucleic acid or conjugated nucleic acid of any of statements 1 to 47 and a physiologically acceptable excipient.

52. A nucleic acid or conjugated nucleic acid according to any of statements 1 to 47 for use in the treatment of a disease or disorder.

53. Use of a nucleic acid or conjugated nucleic acid according to any of statements 1 to 47 in the manufacture of a medicament for treating a disease or disorder.

54. A method of treating a disease or disorder comprising administration of a composition comprising a nucleic acid or conjugated nucleic acid according to any of statements 1 to 47 to an individual in need of treatment.

55. The method of statement 54, wherein the nucleic acid or conjugated nucleic acid is administered to the subject subcutaneously or intravenously.

56. A process of making a nucleic acid or conjugated nucleic acid of any of statements 1 to 47.

57 A nucleic acid, method, use or composition according to any preceding statement, or any disclosure herein, wherein there is no terminal phosphorothioate in the nucleic acid.

58 A nucleic acid, method, use or composition according to any preceding statement, or any disclosure herein, wherein the terminal nucleotide is located at the 3' end of at least one of the first strand and the second strand, or both.

59 A nucleic acid, method, use or composition according to any preceding statement, or any disclosure herein, wherein the ligand does not contain a phosphorothioate, such as a nucleic acid according conjugated to a Galnac moiety which does not contain phosphorothioates.

The invention claimed is:

1. A nucleic acid for inhibiting expression of a target gene in a cell, said nucleic acid comprising at least one duplex region that comprises at least a portion of a first strand and at least a portion of a second strand that is at least partially complementary to the first strand, wherein said first strand is at least partially complementary to at least a portion of RNA transcribed from said target gene to be inhibited and wherein the terminal nucleotide at the 3' end of at least one of the first strand and the second strand is an inverted nucleotide and is attached to the adjacent nucleotide via the 3' carbon of the terminal nucleotide and the 3' carbon of the adjacent nucleotide and/or the terminal nucleotide at the 5' end of at least one of the first strand and the second strand is an inverted nucleotide and is attached to the adjacent nucleotide via the 5' carbon of the terminal nucleotide and the 5' carbon of the adjacent nucleotide, wherein the inverted nucleotide is an inverted ribonucleotide comprising a sugar moiety that does not have a chemical modification.

2. The nucleic acid according to claim 1, which a) is blunt ended at both ends; or
b) has an overhang at one end and a blunt end at the other; or
c) has an overhang at both ends.

3. The nucleic acid according to claim 1, wherein one or more nucleotides on the first and/or second strand are modified, to form modified nucleotides.

4. The nucleic acid according to claim 3, wherein at least one modification is 2'-O-methyl or 2'-F.

5. The nucleic acid according to claim 1, wherein the inverted nucleotide at the 3' end of at least one of the first strand and the second strand and/or the inverted nucleotide at the 5' end of at least one of the first strand and the second strand is a purine.

6. The nucleic acid according to claim 1, further comprising a ligand.

7. A nucleic acid for inhibiting expression of a target gene in a cell, said nucleic acid comprising at least one duplex region that comprises at least a portion of a first strand and at least a portion of a second strand that is at least partially complementary to the first strand, wherein said first strand is at least partially complementary to at least a portion of RNA transcribed from said target gene to be inhibited and wherein the terminal nucleotide at the 3' end of at least one of the first strand and the second strand is an inverted nucleotide and is attached to the adjacent nucleotide via the 3' carbon of the terminal nucleotide and the 3' carbon of the adjacent nucleotide and/or the terminal nucleotide at the 5' end of at least one of the first strand and the second strand is an inverted nucleotide and is attached to the adjacent nucleotide via the 5' carbon of the terminal nucleotide and the 5' carbon of the adjacent nucleotide, and wherein the nucleic acid molecule is directly or indirectly conjugated to a ligand via a linker, wherein the inverted nucleotide is an inverted ribonucleotide comprising a sugar moiety that does not have a chemical modification.

8. The nucleic acid according to claim 7, wherein the ligand comprises one or more GalNac ligands or derivatives thereof.

9. The nucleic acid of claim 8, wherein one or more nucleotides on the first and/or second strand are modified, to form modified nucleotides.

10. A composition comprising the nucleic acid of claim 1 and a physiologically acceptable excipient.

11. A method of treating a disease or disorder comprising administration of a composition comprising the nucleic acid according to claim 1 to an individual in need of treatment.

12. The nucleic acid according to claim 9, wherein at least one modification is 2'-O-methyl or 2'-F.

13. A composition comprising the nucleic acid of claim 4 and a physiologically acceptable excipient.

14. A method of treating a disease or disorder comprising administration of a composition comprising the nucleic of claim 4 to an individual in need of treatment.

15. A composition comprising the conjugated nucleic acid of claim 7 and a physiologically acceptable excipient.

16. A method of treating a disease or disorder comprising administration of a composition comprising the conjugated nucleic acid of claim 7 to an individual in need of treatment.

17. A composition comprising the conjugated nucleic acid of claim 12 and a physiologically acceptable excipient.

18. A method of treating a disease or disorder comprising administration of a composition comprising the conjugated nucleic acid of claim 12 to an individual in need of treatment.

19. The nucleic acid of claim 2, wherein the nucleic acid has an overhang at the 3' end of the first strand and which has a blunt end at the 3' of the second strand.

20. The nucleic acid of claim 2, wherein the nucleic acid has an inverted nucleotide on the 3' end of the second strand, and wherein the inverted nucleotide on the 3'-end of the second strand forms a blunt end.

* * * * *